(12) United States Patent
Tyson

(10) Patent No.: US 9,102,728 B2
(45) Date of Patent: Aug. 11, 2015

(54) PD-1 ANTIBODIES

(75) Inventor: Kerry Louise Tyson, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 1188 days.

(21) Appl. No.: 13/045,718

(22) Filed: Mar. 11, 2011

(65) Prior Publication Data

US 2011/0229461 A1 Sep. 22, 2011

Related U.S. Application Data

(60) Provisional application No. 61/312,702, filed on Mar. 11, 2010.

(51) Int. Cl.
*C07K 16/28* (2006.01)

(52) U.S. Cl.
CPC ......... *C07K 16/2818* (2013.01); *C07K 2316/95* (2013.01); *C07K 2317/24* (2013.01); *C07K 2317/56* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,585,089 A | 12/1996 | Queen et al. | |
| 5,629,204 A | 5/1997 | Honjo et al. | |
| 5,667,425 A | 9/1997 | Pineau et al. | |
| 5,698,520 A | 12/1997 | Honjo et al. | |
| 6,808,710 B1 | 10/2004 | Wood et al. | |
| 7,029,674 B2 | 4/2006 | Carreno et al. | |
| 7,101,550 B2 | 9/2006 | Wood et al. | |
| 7,105,328 B2 | 9/2006 | Wood et al. | |
| 7,432,059 B2 | 10/2008 | Freeman et al. | |
| 7,595,048 B2 | 9/2009 | Honjo et al. | |
| 7,635,757 B2 | 12/2009 | Freeman et al. | |
| 7,638,492 B2 | 12/2009 | Wood et al. | |
| 7,700,301 B2 | 4/2010 | Wood et al. | |
| 7,709,214 B2 | 5/2010 | Freeman et al. | |
| 7,722,868 B2 | 5/2010 | Freeman et al. | |
| 7,851,598 B2 | 12/2010 | Davis | |
| 2004/0033497 A1 | 2/2004 | Alarcon-Riquelme et al. | |
| 2007/0122378 A1 | 5/2007 | Freeman et al. | |
| 2007/0202100 A1* | 8/2007 | Wood et al. ............... | 424/143.1 |
| 2009/0028857 A1 | 1/2009 | Li et al. | |
| 2009/0217401 A1 | 8/2009 | Korman et al. | |
| 2010/0035973 A1 | 2/2010 | Walker | |
| 2010/0040614 A1 | 2/2010 | Ahmed et al. | |
| 2010/0151492 A1 | 6/2010 | Ahmed et al. | |
| 2010/0266617 A1 | 10/2010 | Carven et al. | |
| 2011/0008369 A1 | 1/2011 | Finnefrock et al. | |
| 2011/0171215 A1 | 7/2011 | Davis et al. | |
| 2011/0177088 A1 | 7/2011 | Olive et al. | |
| 2011/0271358 A1 | 11/2011 | Freeman et al. | |
| 2012/0269806 A1 | 10/2012 | Sykes | |

FOREIGN PATENT DOCUMENTS

| | | |
|---|---|---|
| CN | 1753912 A | 3/2006 |
| EP | 0392745 B1 | 11/1994 |
| EP | 0948544 B1 | 5/2003 |
| EP | 1090037 B1 | 11/2004 |
| WO | WO86/01533 A1 | 3/1986 |
| WO | WO89/00195 A1 | 1/1989 |
| WO | WO89/01476 A1 | 2/1989 |
| WO | WO91/09967 A1 | 7/1991 |
| WO | WO92/02551 A1 | 2/1992 |
| WO | WO92/22583 A2 | 12/1992 |
| WO | WO93/06231 A1 | 4/1993 |
| WO | WO98/20734 A1 | 5/1998 |
| WO | WO98/25971 A1 | 6/1998 |
| WO | WO03/031581 A2 | 4/2003 |
| WO | WO03/048208 A2 | 6/2003 |
| WO | WO2004/051268 A1 | 6/2004 |
| WO | WO2004/056875 A1 | 7/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO2005/113605 A1 | 12/2005 |
| WO | WO2005/117984 A2 | 12/2005 |
| WO | WO2007/060406 A1 | 5/2007 |
| WO | WO2008/038024 A1 | 4/2008 |
| WO | WO2008/156712 A1 | 12/2008 |
| WO | WO2009/040562 A1 | 4/2009 |
| WO | WO2010/029434 A1 | 3/2010 |
| WO | WO2010/029435 A1 | 3/2010 |
| WO | WO 2010029434 A1 * | 3/2010 |
| WO | WO 2010029435 A1 * | 3/2010 |
| WO | WO2010/035012 A1 | 4/2010 |

OTHER PUBLICATIONS

Mariuzza et al. (Annu. Rev. Biophys. Biophys. Chem., 16: 139-159, 1987).*
Gussow et al (Methods in Enzymology, 203: 99-121, 1991).*
Winkler et al (J. Imm., 265:4505-4514, 2000).*
Rudikoff et al (Proc. Natl. Acad. Sci. USA 1982 vol. 79: p. 1979-1983).*

(Continued)

*Primary Examiner* — Brad Duffy
(74) *Attorney, Agent, or Firm* — Saul Ewing LLP

(57) ABSTRACT

A humanised agonistic antibody which binds human PD-1 comprising a heavy chain and a light chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the variable domain of the light chain comprises the sequence given in SEQ ID NO:4 for CDR-L1, the sequence given in SEQ ID NO:5 for CDR-L2 and the sequence given in SEQ ID NO:7 for CDR-L3. The invention also extends to therapeutic uses of the antibody molecules, compositions and methods for producing said antibody molecules.

23 Claims, 55 Drawing Sheets

(56) References Cited

OTHER PUBLICATIONS

MacCallum et al. (J. Mol. Biol. Oct. 11, 1996; 262 (5): 732-745).*
Holm et al. (Mol. Immunol. Feb. 2007; 44 (6): 1075-1084).*
Cellular and Molecular Immunology (Eds. Abass et al.; 1991; W.B. Saunders: Philadelphia; p. 54).*
Finlay et al (JMB, 388:541-558, 2008).*
Adair, J.R., et al., "Therapeutic Antibodies", Drug Design Reviews—Online, vol. 2, No. 3, pp. 209-217, 2005.
Agata, Y., et al., "Expression of the PD-1 antigen on the surface of stimulated mouse T and B lymphocytes", Int Immunol, vol. 8, pp. 765-772, 1996.
Altschul, S.F., et al., "Basic local alignment search tool", J. Mol. Biol., vol. 215, No. 3, pp. 403-410, 1990.
Altschul, S.F., et al., "Gapped BLAST and PSI-BLAST: a new generation of protein database search programs", Nucleic Acids Res., vol. 25, pp. 3389-3402, 1997.
Angal, S., et al., "A single amino acid substitution abolishes the heterogeneity of chimeric mouse/human (IgG4) antibody", Molecular Immunology, vol. 30, No. 1, pp. 105-108, 1993.
Babcook, J., et al., A Novel Strategy for generating Monoclonal Antibodies from Single, Isolated Lymphocytes Producing Antibodies of Defined Specificities, Proc. Natl. Acad. Sci. USA, vol. 93, No. 15, pp. 7843-7848, 1996.
Butte, M., et al., "Programmed Death-1 Ligand 1 interacts specifically with B7-1 Costimulatory Molecule to inhibit T cell responses", Immunity, vol. 27, No. 1, pp. 111-122, 2007.
Chapman, A., "PEGylated antibodies and antibody fragments for improved therapy: a review", Advanced Drug Delivery Reviews, vol. 54, No. 4, pp. 531-545, 2002.
Chemnitz, J.M., et al., "SHP-1 and SHP-2 associate with immunoreceptor tyrosine-based switch motif of programmed death 1 upon primary human T cell stimulation, but only receptor ligation prevents T cell activation", J Immunol, vol. 173, pp. 945-954, 2004.
Chothia, C. and Lesk, A.M., "Canonical Structures for the Hypervariable Regions of Immunoglobulins", J. Mol. Biol., vol. 196, pp. 901-917, 1987.
Cole, S.P.C., et al., "The EBV-hybridoma technique and its application to human lung cancer", Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y., 1985.
Crameri, A., et al., "DNA shuffling of a family of genes from diverse species accelerates directed evolution", Nature, vol. 391, pp. 288-291, 1998.
Ding, H., et al., "Delivering PD-1 inhibitory signal concomitant with blocking ICOS co-stimulation suppresses lupus-like syndrome in autoimmune BXSB mice", Clinical Immunology, vol. 118, Nos. 2-3, pp. 258-267, 2006.
Dubowchik, G.M., et al., "Receptor-mediated and enzyme-dependent targeting of cytotoxic anticancer drugs", Pharmacology & Therapeutics, vol. 83, No. 2, pp. 67-123, 1999.
Evans, E.J., et al., "Crystal structure of a soluble CD28-Fab complex", Nat Immunol., vol. 6, No. 3, pp. 271-279, 2005.
Francisco, L.M., et al., "PD-L1 regulates the development, maintenance, and function of induced regulatory T cells", J Exp Med, vol. 206, No. 13, pp. 3015-3029, 2009.
Freeman, G., et al., "Engagement of the PD-1 Immunoinhibitory Receptor by a Novel B7 Family Member Leads to Negative Regulation of Lymphocyte Activation", J. Exp Med, vol. 192, No. 7, p. 1027-1034, 2000.
Gish, W., and States, D.M., "Identification of protein coding regions by data base similarity search", Nature Genet., vol. 3, No. 3, pp. 266-272, 1993.
Harris, J.M., and Zalipsky, S., eds., "Poly(ethyleneglycol) Chemistry and Biological Applications", American Chemical Society, Washington DC, 1997.
Harris, R.J., Processing of C-Terminal Lysine and Arginine Residues of Proteins Isolated from mammalian Cell Culture, Journal of Chromatography A, vol. 705, No. 1, pp. 129-134, 1995.
Hellstrom, K.E., et al., "Antibodies for Drug Delivery", Controlled Drug Delivery, $2^{nd}$ Ed., Robinson, et al., eds., pp. 623-653, 1987.
Hieter, P.A., et al., "Evolution of human immunoglobulin kappa J region genes", J. Biol. Chem., vol. 257, No. 3, pp. 1516-1522, 1982.
Hirata, S., et al., "Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand", The Journal of Immunology, vol. 174, pp. 1888-1897, 2005.
Holliger P., et al., Engineered antibody fragments and the rise of single domains, Nature Biotech., vol. 23, No. 9, pp. 1126-1136, 2005.
Ishida, Y., et al., "Induced expression of PD-1, a novel member of the immunoglobulin gene superfamily, upon programmed cell death", EMBO Journal, vol. 11, No. 11, pp. 3887-3895, 1992.
Kashmiri, S.V.S., et al., "SDR Grafting—A New Approach to Antibody Humanization", Methods, vol. 36, pp. 25-34, 2005.
Keir, M.E. et al., "Programmed Death-1 (PD-1): PD-Ligand 1 Interactions Inhibit TCR-Mediated Positive Selection of Thymocytes," Journal of Immunol., vol. 175, pp. 7372-7379 (2005).
Keir, M.E., et al., PD-1 and Its Ligands in Tolerance and Immunity, Annual Review of Immunology, vol. 26, pp. 677-704, 2008.
Kohler, C., et al., "Continuous cultures of fused cells secreting antibody of predefined specificity", Nature, vol. 256, pp. 495-497 1975.
Kozbor, D., et al., "The production of monoclonal antibodies from human lymphocytes", Immunology Today, vol. 4, No. 3, pp. 72-79, 1983.
Kroner, A., et al., "A PD-1 polymorphism is associated with disease progression in multiple sclerosis", Annals of Neurology, vol. 58, pp. 50-57, 2005.
Latchman, Y., et al., "PD-L2 is a second ligand for PD-1 and Inhibits T cell activation", Immunol, vol. 2, No. 3, pp. 261-268, 2001.
Low, N.M., et al., "Mimicking somatic hypermutation: affinity maturation of antibodies displayed on bacteriophage using a bacterial mutator strain", J. Mol. Biol., vol. 260, pp. 359-368, 1996.
Madden, T.L., et al., "Network BLAST Server Applications", Meth. Enzymol., vol. 266, pp. 131-141, 1996.
Marks, et al., "By-passing Immunization Human: Building High Affinity Human Antibodies by Chain Shuffling", Bio/Technology, vol. 10, pp. 779-783, 1992.
Nishimura, H., et al., "Development of Lupus-like Autoimmune Diseases by Disruption of the PD-1 Gene Encoding an ITIM Motif-Carrying Immunoreceptor", Immunity, vol. 11, pp. 141-151, 1999.
Nishimura, H., et al., "Autoimmune Dilated Cardiomyopathy in PD-1 Receptor-Deficient Mice", Science, vol. 291, No. 5502, pp. 319-322, 2001.
Okazaki, T., et al., "PD-1 and PD-1 ligands: from discovery to clinical application", International Immunology, vol. 19, No. 7, pp. 813-824, 2007.
Patten, P.A., et al., "Applications of DNA shuffling to pharmaceuticals and vaccines", Current Opinion in Biotechnology, vol. 8, No. 6, pp. 724-733, 1997.
Prokunina, L., et al., "A regulatory polymorphism in PDCD1 is associated with susceptibility to systemic lupus erythematosus in humans", Nat Genet, vol. 32, No. 4, pp. 666-669, 2002.
Prokunina, L., et al., "Association of the PD-1.3A Allele of the PDCDI Gene in Patients with Rheumatoid Arthritis Negative for Rheumatoid Factor and the Shared Epitope", Arthritis & Rheumatism, vol. 50, No. 6, pp. 1770-1773, 2004.
Ravetch, J.V., et al., "Structure of the human immunoglobulin mu locus: characterization of embryonic and rearranged J and D genes", Cell, vol. 27, No. 3, Pt 2, pp. 583-591, 1981.
Riechmann, et al., "Reshaping human antibodies for therapy", Nature, vol. 332, pp. 323-324, 1988.
Riley, J.L., "PD-1 signaling in primary T cells", Immunological Reviews, vol. 229, No. 1, pp. 114-125, 2009.
Seko, Y. et al, "Roles of Programmed death-1 (PD-1)/PD-1 ligands pathway in the development of murine acute myocarditis caused by coxsackievirus B3," Cardiovascular Research, vol. 75, pp. 158-167 (2007).

(56) References Cited

OTHER PUBLICATIONS

Thompson, J., et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity", J. Mol. Biol., vol. 256, pp. 77-88, 1996.

Thorpe, P.E., et al., "The Preparation and Cytotoxic Properties of Antibody-Toxin Conjugates", Immunol. Rev., vol. 62, pp. 119-158, 1982.

Vaughan, et al., "Human antibodies by design", Nature Biotechnology, vol. 16, No. 6, pp. 535-539, 1998.

Verma, R., et al., "Antibody engineering: Comparison of bacterial, yeast, insect and mam Malian expression systems", Journal of Immunological Methods, vol. 216, Nos. 1-2, pp. 165-181, 1998.

Wang, J., et al., "Establishment of NOD-Pdcd 1-/- mice as an efficient animal model of type I diabetes", Proc Natl Acad Sci USA, vol. 102, No. 33, pp. 11823-11828, 2005.

Wang, L. et al., "Programmed cell death 1 (PD-1) and its ligand PD-L1 are required for allograft tolerance," Eur. J. Immunol., vol. 37, pp. 2983-2990 (2007).

Yang, W.P., et al., "CDR Walking Mutagenesis for the Affinity Maturation of a Potent Human Anti-HIV-1 Antibody into the Picomolar Range", J. Mol. Biol., vol. 254, No. 3, pp. 392-403, 1995.

Zhang, J., and Madden, T.L., "PowerBlast: A Network Application for Automated Analysis of Large Genomic Sequences", Genome Res., vol. 7, pp. 649-656, 1997.

International Search Report dated May 26, 2011 for PCT/EP2011/053597.

* cited by examiner

Figure 1

(a) Light Chain variable region of antibody 949 (SEQ ID NO:8)
ENVLTQSPAIMSASPGEKVTMTC<u>RASSSVISSYLH</u>WYQQKSGASPKLWIY<u>STSNLAS</u>G
VPDRFSGSGSGTSYSLTISSVEAEDAATYYC<u>QQYNGYPLT</u>FGAGTKLEIK (b) Heavy chain variable region of antibody 949 (SEQ ID NO:9)
QVQLQQSGAELVKPGASVKMSCKAF<u>GYTFTTYPIE</u>WMKQNHGKSLEWIG<u>NFHPYND
DTKYNEKFKG</u>KAKLTVEKSSTTVYLELSRLTSDDSAVYYCAR<u>ENYGSHGGFVY</u>WGQ
GTLVTVS (c)
CDRH1:  GYTFTTYPIE (SEQ ID NO:1)
CDRH2:  NFHPYNDDTKYNEKFKG (SEQ ID NO:2)
CDRH3:  ENYGSHGGFVY (SEQ ID NO:3)
CDRL1:  RASSSVISSYLH (SEQ ID NO:4)
CDRL2:  STSNLAS (SEQ ID NO:5)
CDRL3:  QQYNGYPLT (SEQ ID NO:6)

Figure 2

(a) Modified CDRL3  QQYNSYPLT  (SEQ ID NO:7)

(b) 949 VK1 gL1 V-region  (SEQ ID NO:10)
ENVLTQSPFS LSASVGDRVT ITCRASSSVI SSYLHWYQQK PAKAPKLWIY
STSNLASGVP DRFSGSGSGT SYTLTISSLQ PEDFATYYCQ QYNGYPLTFG
GGTKVEIK (c) 949 VK1 gL1 V-region  (SEQ ID NO:11)
gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct ctggatctac
tccacctcca acttggcatc tggcgtgcct gatagatttt ctgggagcgg
ttccgggaca agctataccc tgacgattag ttccctgcaa ccggaggact
tcgccaccta ttactgtcag cagtacaacg gctacccact gacattcggc
ggagggacta aagtcgaaat caag (d) 949 VK1 gL1 V-region with signal sequence underlined and italicised (SEQ ID NO:12)
*MSVPTQVLGL LLLWLTDARC* ENVLTQSPFS LSASVGDRVT ITCRASSSVI
SSYLHWYQQK PAKAPKLWIY STSNLASGVP DRFSGSGSGT SYTLTISSLQ
PEDFATYYCQ QYNGYPLTFG GGTKVEIK (e) 949 VK1 gL1 V-region with signal sequence underlined and italicised (SEQ ID NO:13)
*atgagtgtgc caactcaggt tctcggattg ctgcttctgt ggcttactga*
*tgcccgctgc* gagaatgtgc tgacacagag ccccttttca ctgtctgcat
ctgtgggaga ccgggtcaca ataacctgca gggctagctc aagcgtgatc
agctcatacc tgcactggta tcagcaaaag cccgccaaag ctcctaagct
ctggatctac tccacctcca acttggcatc tggcgtgcct gatagatttt
ctgggagcgg ttccgggaca agctataccc tgacgattag ttccctgcaa
ccggaggact tcgccaccta ttactgtcag cagtacaacg gctacccact
gacattcggc ggagggacta aagtcgaaat caag (f) 949 VK1 gL1 light chain (V + constant) (SEQ ID NO:14)
ENVLTQSPFS LSASVGDRVT ITCRASSSVI SSYLHWYQQK PAKAPKLWIY
STSNLASGVP DRFSGSGSGT SYTLTISSLQ PEDFATYYCQ QYNGYPLTFG
GGTKVEIKRT VAAPSVFIFP PSDEQLKSGT ASVVCLLNNF YPREAKVQWK
VDNALQSGNS QESVTEQDSK DSTYSLSSTL TLSKADYEKH KVYACEVTHQ
GLSSPVTKSF NRGEC

Figure 3

(a) 949 VK1 gL1 light chain (V + constant) (SEQ ID NO:15)

```
gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct ctggatctac
tccacctcca acttggcatc tggcgtgcct gatagatttt ctgggagcgg
ttccgggaca agctataccc tgacgattag ttccctgcaa ccggaggact
tcgccaccta ttactgtcag cagtacaacg gctacccact gacattcggc
ggagggacta aagtcgaaat caagcgtacg gtagcggccc catctgtctt
catcttcccg ccatctgatg agcagttgaa atctggaact gcctctgttg
tgtgcctgct gaataacttc tatcccagag aggccaaagt acagtggaag
gtggataacg ccctccaatc gggtaactcc caggagagtg tcacagagca
ggacagcaag gacagcacct acagcctcag cagcaccctg acgctgagca
agcagacta cgagaaacac aaagtctacg cctgcgaagt cacccatcag
ggcctgagct cgcccgtcac aaagagcttc aacaggggag agtgt
```

(b) 949 VK1 gL1 light chain with signal sequence underlined and italicised (SEQ ID NO:16)

*MSVPTQVLGL LLLWLTDARC* ENVLTQSPFS LSASVGDRVT ITCRASSSVI
SSYLHWYQQK PAKAPKLWIY STSNLASGVP DRFSGSGSGT SYTLTISSLQ
PEDFATYYCQ QYNGYPLTFG GGTKVEIKRT VAAPSVFIFP PSDEQLKSGT
ASVVCLLNNF YPREAKVQWK VDNALQSGNS QESVTEQDSK DSTYSLSSTL
TLSKADYEKH KVYACEVTHQ GLSSPVTKSF NRGEC (c) 949 VK1 gL1 light chain with signal sequence underlined and italicised (SEQ ID NO:17)

```
atgagtgtgc caactcaggt tctcggattg ctgcttctgt ggcttactga
tgcccgctgc gagaatgtgc tgacacagag ccccttttca ctgtctgcat
ctgtgggaga ccgggtcaca ataacctgca gggctagctc aagcgtgatc
agctcatacc tgcactggta tcagcaaaag cccgccaaag ctcctaagct
ctggatctac tccacctcca acttggcatc tggcgtgcct gatagatttt
ctgggagcgg ttccgggaca agctataccc tgacgattag ttccctgcaa
ccggaggact tcgccaccta ttactgtcag cagtacaacg gctacccact
gacattcggc ggagggacta aagtcgaaat caagcgtacg gtagcggccc
catctgtctt catcttcccg ccatctgatg agcagttgaa atctggaact
gcctctgttg tgtgcctgct gaataacttc tatcccagag aggccaaagt
acagtggaag gtggataacg ccctccaatc gggtaactcc caggagagtg
tcacagagca ggacagcaag gacagcacct acagcctcag cagcaccctg
acgctgagca agcagacta cgagaaacac aaagtctacg cctgcgaagt
cacccatcag ggcctgagct cgcccgtcac aaagagcttc aacaggggag agtgt
```

Figure 3 continued

(d) 949 VK1 gL9 V-region (SEQ ID NO:18)

```
ENVLTQSPFS LSASVGDRVT ITCRASSSVI SSYLHWYQQK PAKAPKLFIY
STSNLASGVP SRFSGSGSGT DYTLTISSLQ PEDFATYYCQ QYNGYPLTFG
GGTKVEIK
```

Figure 4

(a) 949 VK1 gL9 V-region (SEQ ID NO:19)

```
gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct cttcatctac
tccacctcca acttggcatc tggcgtgcct agcagatttt ctgggagcgg
ttccgggaca gactataccc tgacgattag ttccctgcaa ccggaggact
tcgccaccta ttactgtcag cagtacaacg gctacccact gacattcggc
ggagggacta aagtcgaaat caag
```

(b) 949 VK1 gL11 V-region (SEQ ID NO:20)

```
ENVLTQSPFS LSASVGDRVT ITCRASSSVI SSYLHWYQQK PAKAPKLWIY
STSNLASGVP DRFSGSGSGT SYTLTISSLQ PEDFATYYCQ QYNSYPLTFG
GGTKVEIK
```

(c) 949 VK1 gL11 V-region (SEQ ID NO:21)

```
gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct ctggatctac
tccacctcca acttggcatc tggcgtgcct gatagatttt ctgggagcgg
ttccgggaca agctataccc tgacgattag ttccctgcaa ccggaggact
tcgccaccta ttactgtcag cagtacaact cctacccact gacattcggc
ggagggacta aagtcgaaat caag
```

(d) 949 VK1 gL12 V-region (SEQ ID NO:22)

```
ENVMTQSPFS LSASVGDRVT ITCRASSSVI SSYLHWYQQK PAKAPKLFIY
STSNLASGVP SRFSGSGSGT DYTLTISSLQ PEDFATYYCQ QYNGYPLTFG
GGTKVEIK
```

(e) 949 VK1 gL12 V-region (SEQ ID NO:23)

```
gagaatgtga tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct cttcatctac
tccacctcca acttggcatc tggcgtgcct agcagatttt ctgggagcgg
ttccgggaca gactataccc tgacgattag ttccctgcaa ccggaggact
tcgccaccta ttactgtcag cagtacaacg gctacccact gacattcggc
ggagggacta aagtcgaaat caag
```

Figure 4 continued

(f) 949 VK1 gL14 V-region (SEQ ID NO:24)

ENVMTQSPFS LSASVGDRVT ITCRASSSVI SSYLHWYQQK PAKAPKLFIY
STSNLASGVP SRFSGSGSGT DYTLTISSLQ PEDFATYYCQ QYNSYPLTFG
GGTKVEIK

Figure 5

(a) 949 VK1 gL14 V-region (SEQ ID NO:25)

gagaatgtga tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct cttcatctac
tccacctcca acttggcatc tggcgtgcct agcagatttt ctgggagcgg
ttccgggaca gactataccc tgacgattag ttccctgcaa ccggaggact
tcgccaccta ttactgtcag cagtacaact cctacccact gacattcggc
ggagggacta aagtcgaaat caag (b) 949 VK3 gL1 V-region (SEQ ID NO:26)

ENVLTQSPGT LSLSPGERAT LSCRASSSVI SSYLHWYQQK PGQAPRLWIY
STSNLASGVP DRFSGSGSGT SYTLTISRLE PEDFATYYCQ QYNGYPLTFG
GGTKVEIK (c) 949 VK3 gL1 V-region (SEQ ID NO:27)

gaaaacgtcc tgacacaatc tccgggtaca ctgtcactga gccctggaga
gagagctacc ttgagctgcc gagcctcaag tagcgtgatt agctcctacc
tgcactggta tcagcaaaag cctgggcaag caccaaggct gtggatctat
agcacctcca atctggcctc tggtgtgcct gacagattct ctggctctgg
gtctggaacc tcctacaccc tgactatatc acgcctggag ccagaggact
tcgccacata ctactgccag cagtacaacg gctatcccct gacctttggc
ggagggacta aggtggaaat caaa (d) 949 VK3 gL11 V-region (SEQ ID NO:28)

ENVLTQSPGT LSLSPGERAT LSCRASSSVI SSYLHWYQQK PGQAPRLWIY
STSNLASGVP DRFSGSGSGT SYTLTISRLE PEDFATYYCQ QYNSYPLTFG
GGTKVEIK

Figure 5 continued

(e) 949 VK3 gL11 V-region (SEQ ID NO:29)

```
gaaaacgtcc tgacacaatc tccgggtaca ctgtcactga gccctggaga
gagagctacc ttgagctgcc gagcctcaag tagcgtgatt agctcctacc
tgcactggta tcagcaaaag cctgggcaag caccaaggct gtggatctat
agcacctcca atctggcctc tggtgtgcct gacagattct ctggctctgg
gtctggaacc tcctacaccc tgactatatc acgcctggag ccagaggact
tcgccacata ctactgccag cagtacaact cctatcccct gacctttggc
ggagggacta aggtggaaat caaa
```

(f) 949gH1a V-region (SEQ ID NO:30)

```
EVQLVQSGAE VKKPGASVKV SCKAFGYTFT TYPIEWMRQA HGQGLEWIGN
FHPYNDDTKY NEKFKGRVTM TVDKSTTTVY MELSSLRSED TAVYYCAREN
YGSHGGFVYW GQGTLVTVS
```

Figure 6

(a) 949gH1a V-region (SEQ ID NO:31)

```
gaagtgcaac tggtgcagtc tggagctgaa gtgaagaaac ctggtgctag
cgtcaaagtg tcctgcaaag ccttcggcta taccttcacc acgtacccaa
ttgagtggat gaggcaggca cacggacaag gattggagtg gatcggcaac
tttcacccct acaacgacga cacgaagtac aacgagaagt tcaagggtcg
cgtgacaatg accgtcgata agagcacgac cactgtttat atggagctga
gctcactgag atccgaagat actgccgtct actattgtgc ccgagagaat
tacggatcac acggggatt  tgtttactgg ggacaaggca cactggttac cgtctcg
```

(b) 949gH1a V-region with signal sequence underlined and italicised (SEQ ID NO:32)

*MEWSWVFLFF LSVTTGVHSE* VQLVQSGAEV KKPGASVKVS CKAFGYTFTT
YPIEWMRQAH GQGLEWIGNF HPYNDDTKYN EKFKGRVTMT VDKSTTTVYM
ELSSLRSEDT AVYYCARENY GSHGGFVYWG QGTLVTVS

(c) 949gH1a V-region with signal sequence underlined and italicised (SEQ ID NO:33)

```
atggaatgga gctgggtctt tctcttcttc ctgtccgtga caactggtgt
gcactctgaa gtgcaactgg tgcagtctgg agctgaagtg aagaaacctg
gtgctagcgt caaagtgtcc tgcaaagcct tcggctatac cttcaccacg
tacccaattg agtggatgag gcaggcacac ggacaaggat tggagtggat
cggcaacttt caccoctaca cgacgacac  gaagtacaac gagaagttca
agggtcgcgt gacaatgacc gtcgataaga gcacgaccac tgtttatatg
gagctgagct cactgagatc cgaagatact gccgtctact attgtgcccg
agagaattac ggatcacacg ggggatttgt ttactgggga caaggcacac
tggttaccgt ctcg
```

(d) 949gH1a heavy chain (V + constant – hu IgG4P) (SEQ ID NO:34)

EVQLVQSGAE VKKPGASVKV SCKAFGYTFT TYPIEWMRQA HGQGLEWIGN
FHPYNDDTKY NEKFKGRVTM TVDKSTTTVY MELSSLRSED TAVYYCAREN
YGSHGGFVYW GQGTLVTVSS ASTKGPSVFP LAPCSRSTSE STAALGCLVK
DYFPEPVTVS WNSGALTSGV HTFPAVLQSS GLYSLSSVVT VPSSSLGTKT
YTCNVDHKPS NTKVDKRVES KYGPPCPPCP APEFLGGPSV FLFPPKPKDT
LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLGK

Figure 7

(a) 949gH1a heavy chain (V + constant – hu IgG4P, exons underlined) (SEQ ID NO:35)

```
gaagtgcaac tggtgcagtc tggagctgaa gtgaagaaac ctggtgctag
cgtcaaagtg tcctgcaaag ccttcggcta taccttcacc acgtacccaa
ttgagtggat gaggcaggca cacggacaag gattggagtg gatcggcaac
tttcacccct acaacgacga cacgaagtac aacgagaagt tcaagggtcg
cgtgacaatg accgtcgata agagcacgac cactgtttat atggagctga
gctcactgag atccgaagat actgccgtct actattgtgc ccgagagaat
tacggatcac acggggggatt tgtttactgg ggacaaggca cactggttac
cgtctcgagc gcttctacaa agggcccatc cgtcttcccc ctggcgccct
gctccaggag cacctccgag agcacagccg ccctgggctg cctggtcaag
gactacttcc ccgaaccggt gacggtgtcg tggaactcag gcgccctgac
cagcggcgtg cacaccttcc cggctgtcct acagtcctca ggactctact
ccctcagcag cgtggtgacc gtgcctcca gcagcttggg cacgaagacc
tacacctgca acgtagatca caagcccagc aacaccaagg tggacaagag
agttggtgag aggccagcac agggagggag ggtgtctgct ggaagccagg
ctcagccctc ctgcctggac gcaccccggc tgtgcagccc cagcccaggg
cagcaaggca tgccccatct gtctcctcac ccggaggcct ctgaccaccc
cactcatgcc cagggagagg gtcttctgga ttttccacc aggctccggg
cagccacagg ctggatgccc ctaccccagg ccctgcgcat acaggggcag
gtgctgcgct cagacctgcc aagagccata tccgggagga ccctgcccct
gacctaagcc caccccaaag gccaaactct ccactcctc agctcagaca
ccttctctcc tcccagatct gagtaactcc caatcttctc tctgcagagt
ccaaatatgg tccccatgc ccaccatgcc caggtaagcc aacccaggcc
tcgccctcca gctcaaggcg ggacaggtgc cctagagtag cctgcatcca
gggacaggcc ccagccgggt gctgacgcat ccacctccat ctcttcctca
gcacctgagt tcctgggggg accatcagtc ttcctgttcc ccccaaaacc
caaggacact ctcatgatct cccggacccc tgaggtcacg tgcgtggtgg
tggacgtgag ccaggaagac cccgaggtcc agttcaactg gtacgtggat
ggcgtggagg tgcataatgc caagacaaag ccgcgggagg agcagttcaa
cagcacgtac cgtgtggtca gcgtcctcac cgtcctgcac caggactggc
tgaacggcaa ggagtacaag tgcaaggtct ccaacaaagg cctcccgtcc
tccatcgaga aaaccatctc aaagccaaa ggtgggaccc acggggtgcg
agggccacat ggacagaggt cagctcggcc caccctctgc cctgggagtg
accgctgtgc caacctctgt cctacaggg cagccccgag agccacaggt
gtacaccctg cccccatccc aggaggagat gaccaagaac caggtcagcc
tgacctgcct ggtcaaaggc ttctacccca gcgacatcgc cgtggagtgg
gagagcaatg ggcagccgga gaacaactac aagaccacgc ctcccgtgct
ggactccgac ggctccttct cctctacag caggctaacc gtggacaaga
gcaggtggca ggaggggaat gtcttctcat gctccgtgat gcatgaggct
ctgcacaacc actacacaca gaagagcctc tccctgtctc tgggtaaa
```

Figure 8

(a) 949gH1a heavy chain (V + constant – hu IgG4P) with signal sequence underlined and italicised (SEQ ID NO:36)

```
MEWSWVFLFF LSVTTGVHSE VQLVQSGAEV KKPGASVKVS CKAFGYTFTT
YPIEWMRQAH GQGLEWIGNF HPYNDDTKYN EKFKGRVTMT VDKSTTTVYM
ELSSLRSEDT AVYYCARENY GSHGGFVYWG QGTLVTVSSA STKGPSVFPL
APCSRSTSES TAALGCLVKD YFPEPVTVSW NSGALTSGVH TFPAVLQSSG
LYSLSSVVTV PSSSLGTKTY TCNVDHKPSN TKVDKRVESK YGPPCPPCPA
PEFLGGPSVF LFPPKPKDTL MISRTPEVTC VVVDVSQEDP EVQFNWYVDG
VEVHNAKTKP REEQFNSTYR VVSVLTVLHQ DWLNGKEYKC KVSNKGLPSS
IEKTISKAKG QPREPQVYTL PPSQEEMTKN QVSLTCLVKG FYPSDIAVEW
ESNGQPENNY KTTPPVLDSD GSFFLYSRLT VDKSRWQEGN VFSCSVMHEA
LHNHYTQKSL SLSLGK
```

Figure 9

(a) 949gH1a heavy chain (V + constant – hu IgG4P, exons underlined) with signal sequence underlined and italicised (SEQ ID NO:37)

*<u>atggaatgga gctgggtctt tctcttcttc ctgtccgtga caactggtgt</u>*
*<u>gcactctgaa</u>* <u>gtgcaactgg tgcagtctgg agctgaagtg aagaaacctg</u>
<u>gtgctagcgt caaagtgtcc tgcaaagcct cggctatac cttcaccacg</u>
<u>tacccaattg agtggatgag gcaggcacac ggacaaggat tggagtggat</u>
<u>cggcaactt caccoctaca acgacgacac gaagtacaac gagaagttca</u>
<u>agggtcgcgt gacaatgacc gtcgataaga gcacgaccac tgtttatatg</u>
<u>gagctgagct cactgagatc cgaagatact gccgtctact attgtgcccg</u>
<u>agagaattac ggatcacacg ggggatttgt ttactgggga caaggcacac</u>
<u>tggttaccgt ctcgagcgct tctacaaagg gcccatccgt cttcccctg</u>
<u>gcgcctgct ccaggagcac tccgagagc acagccgccc tgggctgcct</u>
<u>ggtcaaggac tacttcccg aaccggtgac ggtgtcgtgg aactcaggcg</u>
<u>ccctgaccag cggcgtgcac accttccgg ctgtcctaca gtcctcagga</u>
<u>ctctactccc tcagcagcgt ggtgaccgtg ccctccagca gcttgggcac</u>
<u>gaagacctac acctgcaacg tagatcacaa gcccagcaac accaaggtgg</u>
<u>acaagagagt tggtgagagg ccagcacagg gagggagggt gtctgctgga</u>
<u>agccaggctc agccctcctg cctggacgca ccccggctgt gcagccccag</u>
<u>cccagggcag caaggcatgc cccatctgtc tcctcacccg gaggcctctg</u>
<u>accacccac tcatgcccag ggagagggtc ttctggattt ttccaccagg</u>
<u>ctccgggcag ccacaggctg gatgcccta ccccaggccc tgcgcataca</u>
<u>ggggcaggtg ctgcgctcag acctgccaag agccatatcc gggaggaccc</u>
<u>tgccctgac ctaagccac cccaaaggcc aaactctcca ctccctcagc</u>
<u>tcagacacct tctctcctcc cagatctgag taactcccaa tcttctctct</u>

Figure 9 continued

```
gcagagtcca aatatggtcc cccatgccca ccatgcccag gtaagccaac
ccaggcctcg ccctccagct caaggcggga caggtgccct agagtagcct
gcatccaggg acaggcccca gccggtgct gacgcatcca cctccatctc
ttcctcagca cctgagttcc tgggggacc atcagtcttc ctgttccccc
caaaacccaa ggacactctc atgatctccc ggacccctga ggtcacgtgc
gtggtggtgg acgtgagcca ggaagacccc gaggtccagt tcaactggta
cgtggatggc gtggaggtgc ataatgccaa gacaaagccg cgggaggagc
agttcaacag cacgtaccgt gtggtcagcg tcctcaccgt cctgcaccag
gactggctga acggcaagga gtacaagtgc aaggtctcca acaaaggcct
cccgtcctcc atcgagaaaa ccatctccaa agccaaaggt gggacccacg
gggtgcgagg ccacatgga cagaggtcag ctcggcccac cctctgccct
gggagtgacc gctgtgccaa cctctgtccc tacagggcag ccccgagagc
cacaggtgta caccctgccc ccatcccagg aggagatgac caagaaccag
gtcagcctga cctgcctggt caaaggcttc tacccagcg acatcgccgt
ggagtgggag agcaatgggc agccggagaa caactacaag accacgcctc
ccgtgctgga ctccgacggc tccttcttcc tctacagcag gctaaccgtg
gacaagagca ggtggcagga ggggaatgtc ttctcatgct ccgtgatgca
tgaggctctg cacaaccact acacacagaa gagcctctcc ctgtctctgg gtaaa
```

Figure 10
(a) 949gH8a V-region (SEQ ID NO:38)

EVQLVQSGAE VKKPGASVKV SCKAFGYTFT TYPIEWMRQA HGQGLEWIGN
FHPYNDDTKY NEKFKGRVTM TRDTSTSTVY MELSSLRSED TAVYYCAREN
YGSHGGFVYW GQGTLVTVS (b) 949gH8a V-region (SEQ ID NO:39)

gaagtgcaac tggtgcagtc tggagctgaa gtgaagaaac ctggtgctag
cgtcaaagtg tcctgcaaag ccttcggcta taccttcacc acgtacccaa
ttgagtggat gaggcaggca cacggacaag gattggagtg gatcggcaac
tttcacccct acaacgacga cacgaagtac aacgagaagt tcaagggtcg
cgtgacaatg accagggata ccagcacgag cactgtttat atggagctga
gctcactgag atccgaagat actgccgtct actattgtgc ccgagagaat
tacggatcac acgggggatt tgtttactgg ggacaaggca cactggttac cgtctcg (c) 949gH20a V-region (SEQ ID NO:40)

EVQLVQSGAE VKKPGASVKV SCKAFGYTFT TYPIEWVRQA PGQGLEWMGN
FHPYNDDTKY NEKFKGRVTM TRDTSTSTVY MELSSLRSED TAVYYCAREN
YGSHGGFVYW GQGTLVTVS (d) 949gH20a V-region (SEQ ID NO:41)

gaagtgcaac tggtgcagtc tggagctgaa gtgaagaaac ctggtgctag
cgtcaaagtg tcctgcaaag ccttcggcta taccttcacc acgtacccaa
ttgagtgggt gaggcaggca cccggacaag gattggagtg gatgggcaac
tttcacccct acaacgacga cacgaagtac aacgagaagt tcaagggtcg
cgtgacaatg accagggata ccagcacgag cactgtttat atggagctga
gctcactgag atccgaagat actgccgtct actattgtgc ccgagagaat
tacggatcac acgggggatt tgtttactgg ggacaaggca cactggttac cgtctcg (e) 949gH1b V-region (SEQ ID NO:42)

EVQLVQSGAE VKKPGSSVKV SCKAFGYTFT TYPIEWMRQA HGQGLEWIGN
FHPYNDDTKY NEKFKGRVTI TVDKSTTTVY MELSSLRSED TAVYYCAREN
YGSHGGFVYW GQGTLVTVS

Figure 10 continued
(f) 949gH1b V-region (SEQ ID NO:43)

```
gaagtgcagc ttgtgcaaag cggcgctgag gtcaaaaagc ccggatcaag
cgtgaaagtc tcatgcaaag ccttcggcta caccttcaca acgtacccta
tcgagtggat gaggcaggct catggccaag gactggaatg gattgggaac
ttccacccat acaacgacga caccaagtac aacgagaagt tcaaggggcg
cgttactata accgtggaca agagcactac caccgtgtac atggagctga
gcagtctgag aagcgaggat acagccgtgt actattgtgc acgggagaat
tatggctctc acggcggatt tgtgtactgg ggccaaggaa cactggttac tgtctcg
```

Figure 11
(a) 949gH8b V-region (SEQ ID NO:44)
EVQLVQSGAE VKKPGSSVKV SCKAFGYTFT TYPIEWMRQA HGQGLEWIGN
FHPYNDDTKY NEKFKGRVTI TADKSTSTAY MELSSLRSED TAVYYCAREN
YGSHGGFVYW GQGTLVTVS (b) 949gH8b V-region (SEQ ID NO:45)
gaagtgcagc ttgtgcaaag cggcgctgag gtcaaaaagc ccggatcaag
cgtgaaagtc tcatgcaaag ccttcggcta caccttcaca acgtaccta
tcgagtggat gaggcaggct catggccaag gactggaatg gattgggaac
ttccacccat acaacgacga caccaagtac aacgagaagt tcaaggggcg
cgttactata accgccgaca agagcactag caccgcctac atggagctga
gcagtctgag aagcgaggat acagccgtgt actattgtgc acgggagaat
tatggctctc acggcggatt tgtgtactgg ggccaaggaa cactggttac tgtctcg (c) 949gH20b V-region (SEQ ID NO:46)
EVQLVQSGAE VKKPGSSVKV SCKASGYTFT TYPIEWVRQA PGQGLEWMGN
FHPYNDDTKY NEKFKGRVTI TADKSTSTAY MELSSLRSED TAVYYCAREN
YGSHGGFVYW GQGTLVTVS (d) 949gH20b V-region (SEQ ID NO:47)
gaagtgcagc ttgtgcaaag cggcgctgag gtcaaaaagc ccggatcaag
cgtgaaagtc tcatgcaaag ccagcggcta caccttcaca acgtaccta
tcgagtgggt gaggcaggct cccggccaag gactggaatg gatggggaac
ttccacccat acaacgacga caccaagtac aacgagaagt tcaaggggcg
cgttactata accgccgaca agagcactag caccgcctac atggagctga
gcagtctgag aagcgaggat acagccgtgt actattgtgc acgggagaat
tatggctctc acggcggatt tgtgtactgg ggccaaggaa cactggttac tgtctcg (e) Human VK1 2-1-(1) L23 JK4 acceptor framework (SEQ ID NO:48)
AIRMTQSPFS LSASVGDRVT ITCWASQGIS SYLAWYQQKP AKAPKLFIYY
ASSLQSGVPS RFSGSGSGTD YTLTISSLQP EDFATYYCQQ YYSTPLTFGG GTKVEIK (f) Human VK1 2-1-(1) L23 JK4 acceptor framework (SEQ ID NO:49)
gccatccgga tgacccagtc tccattctcc ctgtctgcat ctgtaggaga
cagagtcacc atcacttgct gggccagtca gggcattagc agttatttag
cctggtatca gcaaaaacca gcaaagccc taagctctt catctattat
gcatccagtt tgcaaagtgg ggtcccatca aggttcagcg gcagtggatc
tgggacggat tacactctca ccatcagcag cctgcagcct gaagattttg
caacttatta ctgtcaacag tattatagta cccctctcac tttcggcgga
gggaccaagg tggagatcaa a

Figure 12

(a) Human VK3 6-1-(1) A27 JK4 acceptor framework (SEQ ID NO:50)

EIVLTQSPGT LSLSPGERAT LSCRASQSVS SSYLAWYQQK PGQAPRLLIY
GASSRATGIP DRFSGSGSGT DFTLTISRLE PEDFAVYYCQ QYGSSPLTFG
GGTKVEIK

(b) Human VK3 6-1-(1) A27 JK4 acceptor framework (SEQ ID NO:51)

gaaattgtgt tgacgcagtc tccaggcacc ctgtctttgt ctccagggga
aagagccacc ctctcctgca gggccagtca gagtgttagc agcagctact
tagcctggta ccagcagaaa cctggccagg ctcccaggct cctcatctat
ggtgcatcca gcagggccac tggcatccca gacaggttca gtggcagtgg
gtctgggaca gacttcactc tcaccatcag cagactggag cctgaagatt
ttgcagtgta ttactgtcag cagtatggta gctcacctct cactttcggc
ggagggacca aggtggagat caaa

(c) Human VH1 1-3 1-46 JH4 acceptor framework (SEQ ID NO:52)

QVQLVQSGAE VKKPGASVKV SCKASGYTFT SYYMHWVRQA PGQGLEWMGI
INPSGGSTSY AQKFQGRVTM TRDTSTSTVY MELSSLRSED TAVYYCARYF
DYWGQGTLVT VS

(d) Human VH1 1-3 1-46 JH4 acceptor framework (SEQ ID NO:53)

caggtgcagc tggtgcagtc tggggctgag gtgaagaagc ctggggcctc
agtgaaggtt tcctgcaagg catctggata caccttcacc agctactata
tgcactgggt gcgacaggcc cctggacaag gcttgagtg gatgggaata
atcaaccctā gtggtggtag cacaagctac gcacagaagt tccagggcag
agtcaccatg accagggaca cgtccacgag cacagtctac atggagctga
gcagcctgag atctgaggac acggccgtgt attactgtgc gagatacttt
gactactggg gccagggaac cctggtcacc gtctcc

Figure 12 continued (e) Human VH1 1-2 1-e JH4 acceptor framework (SEQ ID NO:54)

```
QVQLVQSGAE VKKPGSSVKV SCKASGGTFS SYAISWVRQA PGQGLEWMGG
IIPIFGTANY AQKFQGRVTI TADKSTSTAY MELSSLRSED TAVYYCARYF
DYWGQGTLVT VS
```

(f) Human VH1 1-2 1-e JH4 acceptor framework (SEQ ID NO:55)

```
caggtgcagc tggtgcagtc tggggctgag gtgaagaagc ctgggtcctc
ggtgaaggtc tcctgcaagg cttctggagg caccttcagc agctatgcta
tcagctgggt gcgacaggcc cctggacaag ggcttgagtg gatgggaggg
atcatcccta tctttggtac agcaaactac gcacagaagt tccagggcag
agtcacgatt accgcggaca atccacgag cacagcctac atggagctga
gcagcctgag atctgaggac acggccgtgt attactgtgc gagatacttt
gactactggg gccagggaac cctggtcacc gtctcc
```

Figure 17

VK1 LIGHT CHAIN Graft 949

```
                1   5    10   15   20   25   30 a  35   40   45   50   55   60   65   70   75   80   85   90   95   100  105
Light 949       ENVLTQSPAIMSASPGEKVTMTCRASSSVISSYLHWYQQKSGASPKLWIYSTSNLASGVPDRFSGSGSGTSYSLTISSVEAEDAATYYCQQYNGYPLTFGAGTKLEIK
VK1 2-1-(1) L23 AIRMTQSPFSLSASVGDRVTITCWASQGISS-YLAWYQQKPAKAPKLFIYYASSLQSGVPSRFSGSGSGTDYTLTISSLQPEDFATYYCQQYYSTPLTFGGGTKVEIK
949 VK1 gL1     ENVLTQSPFSLSASVGDRVTITCRASSSVISSYLHWYQQKPAKAPKLFIYSTSNLASGVPSRFSGSGSGTDYTLTISSLQPEDFATYYCQQYNGYPLTFGGGTKVEIK
949 VK1 gL9     ENVLTQSPFSLSASVGDRVTITCRASSSVISSYLHWYQQKPAKAPKLFIYSTSNLASGVPSRFSGSGSGTDYTLTISSLQPEDFATYYCQQYNGYPLTFGGGTKVEIK
949 VK1 gL11    ENVLTQSPFSLSASVGDRVTITCRASSSVISSYLHWYQQKPAKAPKLFIYSTSNLASGVPSRFSGSGSGTDYTLTISSLQPEDFATYYCQQYNSYPLTFGGGTKVEIK
949 VK1 gL12    ENVMTQSPFSLSASVGDRVTITCRASSSVISSYLHWYQQKPAKAPKLFIYSTSNLASGVPSRFSGSGSGTDYTLTISSLQPEDFATYYCQQYNGYPLTFGGGTKVEIK
949 VK1 gL14    ENVMTQSPFSLSASVGDRVTITCRASSSVISSYLHWYQQKPAKAPKLFIYSTSNLASGVPSRFSGSGSGTDYTLTISSLQPEDFATYYCQQYNSYPLTFGGGTKVEIK
```

VK3 LIGHT CHAIN Graft 949

```
                1   5    10   15   20   25   30 a  35   40   45   50   55   60   65   70   75   80   85   90   95   100  105
Light 949       ENVLTQSPAIMSASPGEKVTMTCRASSSVISSYLHWYQQKSGASPKLWIYSTSNLASGVPDRFSGSGSGTSYSLTISSVEAEDAATYYCQQYNGYPLTFGAGTKLEIK
VK3 6-1-(1) A27 EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGGGTKVEIK
949 VK3 gL1     ENVLTQSPGTLSLSPGERATLSCRASSSVISSYLHWYQQKPGQAPRLWIYSTSNLASGVPDRFSGSGSGTSYTLTISRLEPEDFATYYCQQYNGYPLTFGGGTKVEIK
949 VK3 gL11    ENVLTQSPGTLSLSPGERATLSCRASSSVISSYLHWYQQKPGQAPRLWIYSTSNLASGVPDRFSGSGSGTSYTLTISRLEPEDFATYYCQQYNSYPLTFGGGTKVEIK
```

Figure 18

HEAVY CHAIN Graft 949

```
             1   5    10   15   20   25   30   35   40   a 45  50  a 55   60   65   70   75   80 abc 85   90   95  100   105  110
Heavy 949    QVQLQQSGAELVKPGASVKMSCKAFGYTFTTYPIEWMKQNHGKSLEWIGNFHPYNDDTKYNEKFKGKAKLTVEKSSTTVYLELSRLTSDDSAVYYCARENYGSHGGFVYWGQGTLVTVS
VH1 1-3 1-46 QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR------YFDYWGQGTLVTVS 949gH1a      EVQLVQSGAEVKKPGASVKVSCKAFGYTFTTYPIEWMRQAHGQGLEWIGNFHPYNDDTKYNEKFKGRVTMTVDKSTTTVYMELSSLRSEDTAVYYCARENYGSHGGFVYWGQGTLVTVS
949gH8a      EVQLVQSGAEVKKPGASVKVSCKAFGYTFTTYPIEWMRQAHGQGLEWIGNFHPYNDDTKYNEKFKGRVTMTRDTSTSTVYMELSSLRSEDTAVYYCARENYGSHGGFVYWGQGTLVTVS
949gH20a     EVQLVQSGAEVKKPGASVKVSCKAFGYTFTTYPIEWVRQAPGQGLEWMGNFHPYNDDTKYNEKFKGRVTMTRDTSTSTVYMELSSLRSEDTAVYYCARENYGSHGGFVYWGQGTLVTVS 1   5    10   15   20   25   30   35   40   a 45  50  a 55   60   65   70   75   80 abc 85   90   95  100   105  110
Heavy 949    QVQLQQSGAELVKPGASVKMSCKAFGYTFTTYPIEWMKQNHGKSLEWIGNFHPYNDDTKYNEKFKGKAKLTVEKSSTTVYLELSRLTSDDSAVYYCARENYGSHGGFVYWGQGTLVTVS
VH1 1-2 1-e  QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAR------YFDYWGQGTLVTVS 949gH1b      EVQLVQSGAEVKKPGSSVKVSCKAFGYTFTTYPIEWMRQAHGQGLEWIGNFHPYNDDTKYNEKFKGRVTITVDKSTTTVYMELSSLRSEDTAVYYCARENYGSHGGFVYWGQGTLVTVS
949gH8b      EVQLVQSGAEVKKPGSSVKVSCKAFGYTFTTYPIEWMRQAHGQGLEWIGNFHPYNDDTKYNEKFKGRVTITADKSTSTAYMELSSLRSEDTAVYYCARENYGSHGGFVYWGQGTLVTVS
949gH20b     EVQLVQSGAEVKKPGSSVKVSCKAFGYTFTTYPIEWVRQAPGQGLEWMGNFHPYNDDTKYNEKFKGRVTITADKSTSTAYMELSSLRSEDTAVYYCARENYGSHGGFVYWGQGTLVTVS
```

Figure 19
(a) 949gH1a heavy chain (V + constant – hu IgG4P delta Lys) (SEQ ID NO:58)

```
EVQLVQSGAE  VKKPGASVKV  SCKAFGYTFT  TYPIEWMRQA  HGQGLEWIGN
FHPYNDDTKY  NEKFKGRVTM  TVDKSTTTVY  MELSSLRSED  TAVYYCAREN
YGSHGGFVYW  GQGTLVTVSS  ASTKGPSVFP  LAPCSRSTSE  STAALGCLVK
DYFPEPVTVS  WNSGALTSGV  HTFPAVLQSS  GLYSLSSVVT  VPSSSLGTKT
YTCNVDHKPS  NTKVDKRVES  KYGPPCPPCP  APEFLGGPSV  FLFPPKPKDT
LMISRTPEVT  CVVVDVSQED  PEVQFNWYVD  GVEVHNAKTK  PREEQFNSTY
RVVSVLTVLH  QDWLNGKEYK  CKVSNKGLPS  SIEKTISKAK  GQPREPQVYT
LPPSQEEMTK  NQVSLTCLVK  GFYPSDIAVE  WESNGQPENN  YKTTPPVLDS
DGSFFLYSRL  TVDKSRWQEG  NVFSCSVMHE  ALHNHYTQKS  LSLSLG
```

Figure 20

(a) 949gH1a heavy chain (V + constant – hu IgG4P delta Lys, exons underlined)

(SEQ ID NO: 59)

```
gaagtgcaac tggtgcagtc tggagctgaa gtgaagaaac ctggtgctag cgtcaaagtg
tcctgcaaag ccttcggcta taccttcacc acgtacccaa ttgagtggat gaggcaggca
cacggacaag gattggagtg gatcggcaac tttcacccct acaacgacga cacgaagtac
aacgagaagt tcaagggtcg cgtgacaatg accgtcgata agagcacgac cactgtttat
atggagctga gctcactgag atccgaagat actgccgtct actattgtgc ccgagagaat
tacggatcac acgggggatt tgtttactgg ggacaaggca cactggttac cgtctcgagc
gcttctacaa agggcccatc cgtcttcccc ctggcgccct gctccaggag cacctccgag
agcacagccg ccctgggctg cctggtcaag gactacttcc ccgaaccggt gacggtgtcg
tggaactcag gcgccctgac cagcggcgtg cacaccttcc cggctgtcct acagtcctca
ggactctact ccctcagcag cgtggtgacc gtgccctcca gcagcttggg cacgaagacc
tacacctgca acgtagatca caagcccagc aacaccaagg tggacaagag agttggtgag
aggccagcac agggagggag ggtgtctgct ggaagccagg ctcagccctc ctgcctggac
gcacccggc tgtgcagccc cagcccaggg cagcaaggca tgccccatct gtctcctcac
ccggaggcct ctgaccaccc cactcatgcc cagggagagg gtcttctgga tttttccacc
aggctccggg cagccacagg ctggatgccc ctaccccagg ccctgcgcat acagggcag
gtgctgcgct cagacctgcc aagagccata tccgggagga ccctgcccct gacctaagcc
cacccaaag gccaaactct ccactccctc agctcagaca ccttctctcc tcccagatct
gagtaactcc caatcttctc tctgcagagt ccaaatatgg tcccccatgc ccaccatgcc
caggtaagcc aacccaggcc tcgccctcca gctcaaggcg ggacaggtgc cctagagtag
cctgcatcca gggacaggcc ccagccgggt gctgacgcat ccacctccat ctcttcctca
gcacctgagt tcctggggg accatcagtc ttcctgttcc ccccaaaacc caaggacact
ctcatgatct cccggacccc tgaggtcacg tgcgtggtgg tggacgtgag ccaggaagac
cccgaggtcc agttcaactg gtacgtggat ggcgtggagg tgcataatgc caagacaaag
ccgcgggagg agcagttcaa cagcacgtac cgtgtggtca gcgtcctcac cgtcctgcac
caggactggc tgaacggcaa ggagtacaag tgcaaggtct ccaacaaagg cctcccgtcc
tccatcgaga aaccatctc caaagccaaa ggtgggaccc acggggtgcg agggccacat
ggacagaggt cagctcggcc caccctctgc cctgggagtg accgctgtgc caacctctgt
ccctacaggg cagccccgag agccacaggt gtacaccctg cccccatccc aggaggagat
gaccaagaac caggtcagcc tgacctgcct ggtcaaaggc ttctacccca gcgacatcgc
cgtggagtgg gagagcaatg ggcagccgga gaacaactac aagaccacgc ctcccgtgct
ggactccgac ggctccttct tcctctacag caggctaacc gtggacaaga gcaggtggca
ggaggggaat gtcttctcat gctccgtgat gcatgaggct ctgcacaacc actacacaca
gaagagcctc tccctgtctc tgggt
```

Figure 21
(a) 949gH1a heavy chain (V + constant – hu IgG4P delta Lys) with signal sequence underlined and italicised (SEQ ID NO: 60)

*MEWSWVFLFF LSVTTGVHSE* VQLVQSGAEV KKPGASVKVS CKAFGYTFTT
YPIEWMRQAH GQGLEWIGNF HPYNDDTKYN EKFKGRVTMT VDKSTTTVYM
ELSSLRSEDT AVYYCARENY GSHGGFVYWG QGTLVTVSSA STKGPSVFPL
APCSRSTSES TAALGCLVKD YFPEPVTVSW NSGALTSGVH TFPAVLQSSG
LYSLSSVVTV PSSSLGTKTY TCNVDHKPSN TKVDKRVESK YGPPCPPCPA
PEFLGGPSVF LFPPKPKDTL MISRTPEVTC VVVDVSQEDP EVQFNWYVDG
VEVHNAKTKP REEQFNSTYR VVSVLTVLHQ DWLNGKEYKC KVSNKGLPSS
IEKTISKAKG QPREPQVYTL PPSQEEMTKN QVSLTCLVKG FYPSDIAVEW
ESNGQPENNY KTTPPVLDSD GSFFLYSRLT VDKSRWQEGN VFSCSVMHEA
LHNHYTQKSL SLSLG

FIGURE 22

(a) 949gH1a heavy chain (V + constant – hu IgG4P delta Lys, exons underlined) with signal sequence underlined and italicised (SEQ ID NO: 61)

```
atggaatgga gctgggtctt tctcttcttc ctgtccgtga caactggtgt gcactctgaa
gtgcaactgg tgcagtctgg agctgaagtg aagaaacctg gtgctagcgt caaagtgtcc
tgcaaagcct tcggctatac cttcaccacg tacccaattg agtggatgag gcaggcacac
ggacaaggat tggagtggat cggcaacttt caccoctaca acgacgacac gaagtacaac
gagaagttca aggtcgcgt gacaatgacc gtcgataaga gcacgaccac tgtttatatg
gagctgagct cactgagatc cgaagatact gccgtctact attgtgcccg agagaattac
ggatcacacg ggggatttgt ttactgggga caaggcacac tggttaccgt ctcgagcgct
tctacaaagg gcccatccgt cttccccctg gcgcctgct ccaggagcac ctccgagagc
acagccgccc tgggctgcct ggtcaaggac tacttcccg aaccggtgac ggtgtcgtgg
aactcaggcg ccctgaccag cggcgtgcac accttcccgg ctgtcctaca gtcctcagga
ctctactccc tcagcagcgt ggtgaccgtg ccctccagca gcttgggcac gaagacctac
acctgcaacg tagatcacaa gcccagcaac accaaggtgg acaagagagt tggtgagagg
ccagcacagg gagggagggt gtctgctgga agccaggctc agccctcctg cctggacgca
cccggctgt gcagccccag cccaggcag caaggcatgc ccatctgtc tcctcacccg
gaggcctctg accacccac tcatgccag ggagagggtc ttctggattt ttccaccagg
ctccgggcag ccacaggctg atgcccta ccccaggccc tgcgcataca ggggcaggtg
ctgcgctcag acctgccaag agccatatcc gggaggaccc tgccctgac ctaagcccac
cccaaaggcc aaactctcca ctccctcagc tcagacacct tctctcctcc cagatctgag
taactcccaa tcttctctct gcagagtcca aatatggtcc ccatgccca ccatgccag
gtaagccaac ccaggcctcg ccctccagct caaggcggga caggtgccct agagtagcct
gcatccaggg acaggcccca gccgggtgct gacgcatcca cctccatctc ttcctcagca
cctgagttcc tgggggggacc atcagtcttc ctgttccccc caaaacccaa ggacactctc
atgatctccc ggacccctga ggtcacgtgc gtggtggtgg acgtgagcca ggaagacccc
gaggtccagt tcaactggta cgtggatggc gtggaggtgc ataatgccaa gacaaagccg
cgggaggagc agttcaacag cacgtaccgt gtggtcagcg tcctcaccgt cctgcaccag
gactggctga acggcaagga gtacaagtgc aaggtctcca caaaggcct cccgtcctcc
atcgagaaaa ccatctccaa agccaaggt gggacccacg gggtgcgagg gccacatgga
cagaggtcag ctcggcccac cctctgccct gggagtgacc gctgtgccaa cctctgtccc
tacagggcag ccccgagagc acaggtgta caccctgccc catcccagg aggagatgac
caagaaccag gtcagcctga cctgcctggt caaaggcttc tacccagcg acatcgccgt
ggagtgggag agcaatgggc agccggagaa caactacaag accacgcctc ccgtgctgga
ctccgacggc tccttcttcc tctacagcag gctaaccgtg gacaagagca ggtggcagga
ggggaatgtc ttctcatgct ccgtgatgca tgaggctctg cacaaccact acacacagaa
gagcctctcc ctgtctctgg gt
```

Figure 23
(a) 949gH1a heavy chain (V + constant – hu IgG1 delta Lys) (SEQ ID NO: 62)

```
EVQLVQSGAE VKKPGASVKV SCKAFGYTFT TYPIEWMRQA HGQGLEWIGN
FHPYNDDTKY NEKFKGRVTM TVDKSTTTVY MELSSLRSED TAVYYCAREN
YGSHGGFVYW GQGTLVTVSS ASTKGPSVFP LAPSSKSTSG GTAALGCLVK
DYFPEPVTVS WNSGALTSGV HTFPAVLQSS GLYSLSSVVT VPSSSLGTQT
YICNVNHKPS NTKVDKKVEP KSCDKTHTCP PCPAPELLGG PSVFLFPPKP
KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ
VYTLPPSRDE LTKNQVSLTC LVKGFYPSDI AVEWESNGQP ENNYKTTPPV
LDSDGSFFLY SKLTVDKSRW QQGNVFSCSV MHEALHNHYT QKSLSLSPG
```

FIGURE 24

(a) 949gH1a heavy chain (V + constant – hu IgG1 delta Lys, exons underlined) (SEQ ID NO: 63)

```
gaagtgcaac tggtgcagtc tggagctgaa gtgaagaaac ctggtgctag cgtcaaagtg
tcctgcaaag ccttcggcta taccttcacc acgtacccaa ttgagtggat gaggcaggca
cacggacaag gattggagtg gatcggcaac tttcacccct acaacgacga cacgaagtac
aacgagaagt tcaagggtcg cgtgacaatg accgtcgata agagcacgac cactgtttat
atggagctga gctcactgag atccgaagat actgccgtct actattgtgc ccgagagaat
tacggatcac acgggggatt tgtttactgg ggacaaggca cactggttac cgtctcgagc
gcttctacaa agggcccatc ggtcttcccc ctggcaccct cctccaagag cacctctggg
ggcacagcgg ccctgggctg cctggtcaag gactacttcc ccgaaccggt gacggtgtcg
tggaactcag gcgccctgac cagcggcgtg cacaccttcc cggctgtcct acagtcctca
ggactctact ccctcagcag cgtggtgacc gtgccctcca gcagcttggg cacccagacc
tacatctgca acgtgaatca caagcccagc aacaccaagg tggacaagaa agttggtgag
aggccagcac agggagggag ggtgtctgct ggaagccagg ctcagcgctc tgcctggac
gcatcccggc tatgcagccc cagtccaggg cagcaaggca ggccccgtct gcctcttcac
ccggaggcct ctgcccgccc cactcatgct cagggagagg gtcttctggc tttttcccca
ggctctgggc aggcacaggc taggtgcccc taacccaggc cctgcacaca aagggcagg
tgctgggctc agacctgcca agagccatat ccgggaggac cctgccctg acctaagccc
accccaaagg ccaaactctc cactccctca gctcggacac cttctctcct cccagatctg
agtaactccc aatcttctct ctgcagagcc caaatcttgt gacaaaactc acacatgccc
accgtgccca ggtaagccag cccaggcctc gccctccagc tcaaggcggg acaggtgccc
tagagtagcc tgcatccagg gacaggcccc agccgggtgc tgacacgtcc acctccatct
cttcctcagc acctgaactc ctgggggggac cgtcagtctt cctcttcccc ccaaaaccca
aggacaccct catgatctcc cggacccctg aggtcacatg cgtggtggtg gacgtgagcc
acgaagaccc tgaggtcaag ttcaactggt acgtggacgg cgtggaggtg cataatgcca
agacaaagcc gcgggaggag cagtacaaca gcacgtaccg tgtggtcagc gtcctcaccg
tcctgcacca ggactggctg aatggcaagg agtacaagtg caaggtctcc aacaaagccc
tcccagcccc catcgagaaa accatctcca aagccaaagg tgggacccgt ggggtgcgag
ggccacatgg acagaggccg gctcggccca ccctctgccc tgagagtgac cgctgtacca
acctctgtcc ctacaggca gccccgagaa ccacaggtgt acaccctgcc cccatcccgg
gatgagctga ccaagaacca ggtcagcctg acctgcctgg tcaaaggctt ctatcccagc
gacatcgccg tggagtggga gagcaatggg cagccggaga acaactacaa gaccacgcct
cccgtgctgg actccgacgg ctccttcttc ctctacagca agctcaccgt ggacaagagc
aggtggcagc aggggaacgt cttctcatgc tccgtgatgc atgaggctct gcacaaccac
tacacgcaga agagcctctc cctgtctccg
ggt
```

Figure 25

(a) 949gH1a heavy chain (V + constant – hu IgG1 delta Lys with signal sequence underlined and italicised (SEQ ID NO:64)

*MEWSWVFLFF LSVTTGVHS*E VQLVQSGAEV KKPGASVKVS CKAFGYTFTT
YPIEWMRQAH GQGLEWIGNF HPYNDDTKYN EKFKGRVTMT VDKSTTTVYM
ELSSLRSEDT AVYYCARENY GSHGGFVYWG QGTLVTVSSA STKGPSVFPL
APSSKSTSGG TAALGCLVKD YFPEPVTVSW NSGALTSGVH TFPAVLQSSG
LYSLSSVVTV PSSSLGTQTY ICNVNHKPSN TKVDKKVEPK SCDKTHTCPP
CPAPELLGGP SVFLFPPKPK DTLMISRTPE VTCVVVDVSH EDPEVKFNWY
VDGVEVHNAK TKPREEQYNS TYRVVSVLTV LHQDWLNGKE YKCKVSNKAL
PAPIEKTISK AKGQPREPQV YTLPPSRDEL TKNQVSLTCL VKGFYPSDIA
VEWESNGQPE NNYKTTPPVL DSDGSFFLYS KLTVDKSRWQ QGNVFSCSVM
HEALHNHYTQ KSLSLSPG

Figure 26
(a) 949gH1a heavy chain (V + constant – hu IgG1 delta Lys exons underlined) with signal sequence underlined and italicised (SEQ ID NO: 65)

*atggaatgga gctgggtctt tctcttcttc ctgtccgtga caactggtgt gcactctgaa*
gtgcaactgg tgcagtctgg agctgaagtg aagaaacctg gtgctagcgt caaagtgtcc
tgcaaagcct tcggctatac cttcaccacg tacccaattg agtggatgag gcaggcacac
ggacaaggat tggagtggat cggcaacttt caccctaca acgacgacac gaagtacaac
gagaagttca agggtcgcgt gacaatgacc gtcgataaga gcacgaccac tgtttatatg
gagctgagct cactgagatc cgaagatact gccgtctact attgtgcccg agagaattac
ggatcacacg ggggatttgt ttactgggga caaggcacac tggttaccgt ctcgagcgct
tctacaaagg gcccatcggt cttccccctg gcacctcct ccaagagcac ctctggggc
acagcggccc tgggctgcct ggtcaaggac tacttccccg aaccggtgac ggtgtcgtgg
aactcaggcg ccctgaccag cggcgtgcac accttccgg ctgtcctaca gtcctcagga
ctctactccc tcagcagcgt ggtgaccgtg ccctccagca gcttgggcac ccagacctac
atctgcaacg tgaatcacaa gcccagcaac accaaggtgg acaagaaagt tggtgagagg
ccagcacagg gagggagggt gtctgctgga agccaggctc agcgctcctg cctggacgca
tcccggctat gcagcccag tccagggcag caaggcaggc ccgtctgcc tcttcacccg
gaggcctctg cccgccccac tcatgctcag ggagagggtc ttctggcttt ttccccaggc
tctgggcagg cacaggctag gtgcccctaa cccaggccct gcacacaaag gggcaggtgc
tgggctcaga cctgccaaga gccatatccg ggaggaccct gcccctgacc taagcccacc
ccaaaggcca aactctccac tccctcagct cggacacctt ctctcctccc agatctgagt
aactcccaat cttctctctg cagagcccaa atcttgtgac aaaactcaca catgcccacc
gtgcccaggt aagccagccc aggcctcgcc ctccagctca aggcgggaca ggtgccctag
agtagcctgc atccagggac aggccccagc cgggtgctga cacgtccacc tccatctctt
cctcagcacc tgaactcctg gggggaccgt cagtcttcct cttccccca aacccaagg
acacctcat gatctcccgg acccctgagg tcacatgcgt ggtggtggac gtgagccacg
aagaccctga ggtcaagttc aactggtacg tggacggcgt ggaggtgcat aatgccaaga
caaagccgcg ggaggagcag tacaacagca cgtaccgtgt ggtcagcgtc ctcaccgtcc
tgcaccagga ctggctgaat ggcaaggagt acaagtgcaa ggtctccaac aaagccctcc
cagcccccat cgagaaaacc atctccaaag ccaaaggtgg gacccgtggg gtgcgagggc
cacatggaca gaggccggct cggcccaccc tctgccctga gagtgaccgc tgtaccaacc
tctgtcccta cagggcagcc ccgagaacca caggtgtaca ccctgccccc atcccgggat
gagctgacca agaaccaggt cagcctgacc tgcctggtca aaggcttcta tcccagcgac
atcgccgtgg agtgggagag caatgggcag ccggagaaca actacaagac cacgcctccc
gtgctggact ccgacggctc cttcttcctc tacagcaagc tcaccgtgga caagagcagg
tggcagcagg ggaacgtctt ctcatgctcc gtgatgcatg aggctctgca caaccactac
acgcagaaga gcctctccct gtctccgggt

Figure 27

(a) 949 VK1 gL15 V-region (SEQ ID NO: 66)

ENVLTQSPFS LSASVGDRVT ITCRASSSVI SSYLHWYQQK PAKAPKLFIY
STSNLASGVP SRFSGSGSGT DYTLTISSLQ PEDFATYYCQ QYNSYPLTFG
GGTKVEIK (b) 949 VK1 gL15 V-region (SEQ ID NO: 67)

gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct cttcatctac
tccacctcca acttggcatc tggcgtgcct agcagatttt ctgggagcgg
ttccgggaca gactataccc tgacgattag ttccctgcaa ccggaggact
tcgccaccta ttactgtcag cagtacaact cctacccact gacattcggc
ggagggacta aagtcgaaat caag (c) 949 VK1 gL15 V-region with signal sequence underlined and italicised (SEQ ID NO: 68)

*MSVPTQVLGL LLLWLTDARC* ENVLTQSPFS LSASVGDRVT ITCRASSSVI
SSYLHWYQQK PAKAPKLFIY STSNLASGVP SRFSGSGSGT DYTLTISSLQ
PEDFATYYCQ QYNSYPLTFG GGTKVEIK

Figure 28

(a) 949 VK1 gL15 V-region with signal sequence underlined and italicised (SEQ ID NO: 69)

*atgagtgtgc caactcaggt tctcggattg ctgcttctgt ggcttactga*
*tgc*ccgctgc gagaatgtgc tgacacagag ccccttttca ctgtctgcat
ctgtgggaga ccgggtcaca ataacctgca gggctagctc aagcgtgatc
agctcatacc tgcactggta tcagcaaaag cccgccaaag ctcctaagct
cttcatctac tccacctcca acttggcatc tggcgtgcct agcagatttt
ctgggagcgg ttccgggaca gactataccc tgacgattag ttccctgcaa
ccggaggact cgccaccta ttactgtcag cagtacaact cctacccact
gacattcggc ggagggacta aagtcgaaat caag (b) 949 VK1 gL15 light chain (V + constant) (SEQ ID NO: 70)

ENVLTQSPFS LSASVGDRVT ITCRASSSVI SSYLHWYQQK PAKAPKLFIY
STSNLASGVP SRFSGSGSGT DYTLTISSLQ PEDFATYYCQ QYNSYPLTFG
GGTKVEIKRT VAAPSVFIFP PSDEQLKSGT ASVVCLLNNF YPREAKVQWK
VDNALQSGNS QESVTEQDSK DSTYSLSSTL TLSKADYEKH KVYACEVTHQ
GLSSPVTKSF NRGEC

Figure 29

(a) 949 VK1 gL15 light chain (V + constant) (SEQ ID NO: 71)

gagaatgtgc tgacacagag ccccttttca ctgtctgcat ctgtgggaga
ccgggtcaca ataacctgca gggctagctc aagcgtgatc agctcatacc
tgcactggta tcagcaaaag cccgccaaag ctcctaagct cttcatctac
tccacctcca acttggcatc tggcgtgcct agcagatttt ctgggagcgg
ttccgggaca gactataccc tgacgattag ttccctgcaa ccggaggact
tcgccaccta ttactgtcag cagtacaact cctacccact gacattcggc
ggagggacta aagtcgaaat caagcgtacg gtagcggccc catctgtctt
catcttcccg ccatctgatg agcagttgaa atctggaact gcctctgttg
tgtgcctgct gaataacttc tatcccagag aggccaaagt acagtggaag
gtggataacg ccctccaatc gggtaactcc caggagagtg tcacagagca
ggacagcaag gacagcacct acagcctcag cagcaccctg acgctgagca
aagcagacta cgagaaacac aaagtctacg cctgcgaagt cacccatcag
ggcctgagct cgcccgtcac aaagagcttc aacaggggag agtgt (b) 949 VK1 gL15 light chain with signal sequence underlined and italicised (SEQ ID NO: 72)

*MSVPTQVLGL LLLWLTDARC* ENVLTQSPFS LSASVGDRVT ITCRASSSVI
SSYLHWYQQK PAKAPKLFIY STSNLASGVP SRFSGSGSGT DYTLTISSLQ
PEDFATYYCQ QYNSYPLTFG GGTKVEIKRT VAAPSVFIFP PSDEQLKSGT
ASVVCLLNNF YPREAKVQWK VDNALQSGNS QESVTEQDSK DSTYSLSSTL
TLSKADYEKH KVYACEVTHQ GLSSPVTKSF NRGEC

Figure 30

(a) 949 VK1 gL15 light chain with signal sequence underlined and italicised (SEQ ID NO:73)

*atgagtgtgc caactcaggt tctcggattg ctgcttctgt ggcttactga*
*tgc*ccgctgc gagaatgtgc tgacacagag ccccttttca ctgtctgcat
ctgtgggaga ccgggtcaca ataacctgca gggctagctc aagcgtgatc
agctcatacc tgcactggta tcagcaaaag cccgccaaag ctcctaagct
cttcatctac tccacctcca acttggcatc tggcgtgcct agcagatttt
ctgggagcgg ttccgggaca gactataccc tgacgattag ttccctgcaa
ccggaggact cgccaccta ttactgtcag cagtacaact cctacccact
gacattcggc ggagggacta aagtcgaaat caagcgtacg gtagcggccc
catctgtctt catcttcccg ccatctgatg agcagttgaa atctggaact
gcctctgttg tgtgcctgct gaataacttc tatcccagag aggccaaagt
acagtggaag gtggataacg ccctccaatc gggtaactcc caggagagtg
tcacagagca ggacagcaag gacagcacct acagcctcag cagcaccctg
acgctgagca agcagacta cgagaaacac aaagtctacg cctgcgaagt
cacccatcag ggcctgagct cgcccgtcac aaagagcttc aacaggggag agtgt

Figure 31

(a) 949gH20b V-region with signal sequence underlined and italicized (SEQ ID NO:74)

*MEWSWVFLFF LSVTTGVHSE* VQLVQSGAEV KKPGSSVKVS CKASGYTFTT
YPIEWVRQAP GQGLEWMGNF HPYNDDTKYN EKFKGRVTIT ADKSTSTAYM
ELSSLRSEDT AVYYCARENY GSHGGFVYWG QGTLVTVS (b) 949gH20b V-region with signal sequence underlined and italicized (SEQ ID NO: 75)

*atggagtggt cctgggtgtt tctcttcttt ctctccgtca caacgggtgt*
*tcatagc*gaa gtgcagcttg tgcaaagcgg cgctgaggtc aaaaagcccg
gatcaagcgt gaaagtctca tgcaaagcca gcggctacac cttcacaacg
taccctatcg agtgggtgag gcaggctccc ggccaaggac tggaatggat
ggggaacttc cacccataca cgacgacac caagtacaac gagaagttca
aggggcgcgt tactataacc gccgacaaga gcactagcac cgcctacatg
gagctgagca gtctgagaag cgaggataca gccgtgtact attgtgcacg
ggagaattat ggctctcacg gcggatttgt gtactggggc caaggaacac
tggttactgt ctcg (c) 949gH20b heavy chain (V + constant – hu IgG4P delta Lys) (SEQ ID NO:76)

EVQLVQSGAE VKKPGSSVKV SCKASGYTFT TYPIEWVRQA PGQGLEWMGN
FHPYNDDTKY NEKFKGRVTI TADKSTSTAY MELSSLRSED TAVYYCAREN
YGSHGGFVYW GQGTLVTVSS ASTKGPSVFP LAPCSRSTSE STAALGCLVK
DYFPEPVTVS WNSGALTSGV HTFPAVLQSS GLYSLSSVVT VPSSSLGTKT
YTCNVDHKPS NTKVDKRVES KYGPPCPPCP APEFLGGPSV FLFPPKPKDT
LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLG

Figure 32

(a) 949gH20b heavy chain (V + constant – hu IgG4P delta Lys) (SEQ ID NO: 77)

gaagtgcagc ttgtgcaaag cggcgctgag gtcaaaaagc ccggatcaag
cgtgaaagtc tcatgcaaag ccagcggcta caccttcaca acgtaccta
tcgagtgggt gaggcaggct cccggccaag gactggaatg gatggggaac
ttccacccat acaacgacga caccaagtac aacgagaagt caaggggcg
cgttactata ccgccgaca agagcactag caccgcctac atggagctga
gcagtctgag aagcgaggat acagccgtgt actattgtgc acgggagaat
tatggctctc acggcggatt tgtgtactgg ggccaaggaa cactggttac
tgtctcgagc gcttctacaa agggcccatc cgtcttcccc ctggcgcct
gctccaggag cacctccgag agcacagccg ccctgggctg cctggtcaag
gactacttcc ccgaaccggt gacggtgtcg tggaactcag gcgccctgac
cagcggcgtg cacaccttcc cggctgtcct acagtcctca ggactctact
ccctcagcag cgtggtgacc gtgccctcca gcagcttggg cacgaagacc
tacacctgca acgtagatca caagcccagc aacaccaagg tggacaagag
agttggtgag aggccagcac agggagggag ggtgtctgct ggaagccagg
ctcagccctc ctgcctggac gcaccccggc tgtgcagccc cagcccaggg
cagcaaggca tgccccatct gtctcctcac ccggaggcct ctgaccaccc
cactcatgcc cagggagagg gtcttctgga tttttccacc aggctccggg
cagccacagg ctggatgccc ctaccccagg ccctgcgcat acaggggcag
gtgctgcgct cagacctgcc aagagccata tccgggagga ccctgcccct
gacctaagcc caccccaaag gccaaactct ccactccctc agctcagaca
ccttctctcc tcccagatct gagtaactcc caatcttctc tctgcagagt
ccaaatatgg tccccatgc ccaccatgcc caggtaagcc aacccaggcc
tcgccctcca gctcaaggcg ggacaggtgc cctagagtag cctgcatcca
gggacaggcc ccagccgggt gctgacgcat ccacctccat ctcttcctca
gcacctgagt tcctgggggg accatcagtc ttcctgttcc ccccaaaacc
caaggacact ctcatgatct cccggacccc tgaggtcacg tgcgtggtgg
tggacgtgag ccaggaagac cccgaggtcc agttcaactg gtacgtggat
ggcgtggagg tgcataatgc caagacaaag ccgcgggagg agcagttcaa
cagcacgtac cgtgtggtca gcgtcctcac cgtcctgcac caggactggc
tgaacggcaa ggagtacaag tgcaaggtct ccaacaaagg cctcccgtcc
tccatcgaga aaaccatctc caaagccaaa ggtgggaccc acggggtgcg

Figure 32 continued

```
agggccacat ggacagaggt cagctcggcc caccctctgc cctgggagtg
accgctgtgc caacctctgt ccctacaggg cagccccgag agccacaggt
gtacaccctg cccccatccc aggaggagat gaccaagaac caggtcagcc
tgacctgcct ggtcaaaggc ttctacccca gcgacatcgc cgtggagtgg
gagagcaatg ggcagccgga gaacaactac aagaccacgc ctcccgtgct
ggactccgac ggctccttct tcctctacag caggctaacc gtggacaaga
gcaggtggca ggagggaat gtcttctcat gctccgtgat gcatgaggct
ctgcacaacc actacacaca gaagagcctc tccctgtctc tgggt
```

Figure 33

(a) 949gH20b heavy chain (V + constant – hu IgG4P delta Lys) with signal sequence underlined and italicized (SEQ ID NO: 78)

```
MEWSWVFLFF LSVTTGVHSE VQLVQSGAEV KKPGSSVKVS CKASGYTFTT
YPIEWVRQAP GQGLEWMGNF HPYNDDTKYN EKFKGRVTIT ADKSTSTAYM
ELSSLRSEDT AVYYCARENY GSHGGFVYWG QGTLVTVSSA STKGPSVFPL
APCSRSTSES TAALGCLVKD YFPEPVTVSW NSGALTSGVH TFPAVLQSSG
LYSLSSVVTV PSSSLGTKTY TCNVDHKPSN TKVDKRVESK YGPPCPPCPA
PEFLGGPSVF LFPPKPKDTL MISRTPEVTC VVVDVSQEDP EVQFNWYVDG
VEVHNAKTKP REEQFNSTYR VVSVLTVLHQ DWLNGKEYKC KVSNKGLPSS
IEKTISKAKG QPREPQVYTL PPSQEEMTKN QVSLTCLVKG FYPSDIAVEW
ESNGQPENNY KTTPPVLDSD GSFFLYSRLT VDKSRWQEGN VFSCSVMHEA
LHNHYTQKSL SLSLG
```

Figure 34
(a) 949gH20b heavy chain (V + constant – hu IgG4P delta Lys, exons underlined) with signal sequence underlined and italicised (SEQ ID NO: 79)

```
atggagtggt cctgggtgtt tctcttcttt ctctccgtca caacgggtgt
tcatagcgaa gtgcagcttg tgcaaagcgg cgctgaggtc aaaaagcccg
gatcaagcgt gaaagtctca tgcaaagcca gcggctacac cttcacaacg
tacccatcg agtgggtgag gcaggctccc ggccaaggac tggaatggat
ggggaacttc cacccataca acgacgacac caagtacaac gagaagttca
aggggcgcgt tactataacc gccgacaaga gcactagcac cgcctacatg
gagctgagca gtctgagaag cgaggataca gccgtgtact attgtgcacg
ggagaattat ggctctcacg gcggatttgt gtactggggc caaggaacac
tggttactgt ctcgagcgct tctacaaagg gcccatccgt cttcccctg
gcgccctgct ccaggagcac ctccgagagc acagccgccc tgggctgcct
ggtcaaggac tacttccccg aaccggtgac ggtgtcgtgg aactcaggcg
ccctgaccag cggcgtgcac accttcccgg ctgtcctaca gtcctcagga
ctctactccc tcagcagcgt ggtgaccgtg ccctccagca gcttgggcac
gaagacctac acctgcaacg tagatcacaa gcccagcaac accaaggtgg
acaagagagt tggtgagagg ccagcacagg gagggagggt gtctgctgga
agccaggctc agccctcctg cctggacgca cccggctgt gcagccccag
cccagggcag caaggcatgc cccatctgtc cctcacccg gaggcctctg
accaccccac tcatgcccag ggagagggtc ttctggattt ttccaccagg
ctccgggcag ccacaggctg gatgcccta ccccaggccc tgcgcataca
ggggcaggtg ctgcgctcag acctgccaag agccatatcc gggaggaccc
tgcccctgac ctaagcccac cccaaaggcc aaactctcca ctccctcagc
tcagacacct tctctcctcc cagatctgag taactcccaa tcttctctct
gcagagtcca aatatggtcc cccatgccca ccatgcccag gtaagccaac
ccaggcctcg ccctccagct caaggcggga caggtgccct agagtagcct
gcatccaggg acaggcccca gccgggtgct gacgcatcca cctccatctc
ttcctcagca cctgagttcc tggggggacc atcagtcttc ctgttccccc
caaacccaa ggacactctc atgatctccc ggaccctga ggtcacgtgc
gtggtggtgg acgtgagcca ggaagacccc gaggtccagt tcaactggta
cgtggatggc gtggaggtgc ataatgccaa gacaaagccg cgggaggagc
agttcaacag cacgtaccgt gtggtcagcg tcctcaccgt cctgcaccag
```

Figure 34 continued gactggctga acggcaagga gtacaagtgc aaggtctcca acaaaggcct
cccgtcctcc atcgagaaaa ccatctccaa agccaaaggt gggacccacg
gggtgcgagg gccacatgga cagaggtcag ctcggcccac cctctgccct
gggagtgacc gctgtgccaa cctctgtccc tacagggcag ccccgagagc
cacaggtgta caccctgccc ccatcccagg aggagatgac caagaaccag
gtcagcctga cctgcctggt caaaggcttc tacccagcg acatcgccgt
ggagtgggag agcaatgggc agccggagaa caactacaag accacgcctc
ccgtgctgga ctccgacggc tccttcttcc tctacagcag gctaaccgtg
gacaagagca ggtggcagga ggggaatgtc ttctcatgct ccgtgatgca
tgaggctctg cacaaccact acacacagaa gagcctctcc ctgtctctgg
gt

Figure 35
(a) 949gH20b heavy chain (V + constant – hu IgG1 delta Lys) (SEQ ID NO:80)

```
EVQLVQSGAE  VKKPGSSVKV  SCKASGYTFT  TYPIEWVRQA  PGQGLEWMGN
FHPYNDDTKY  NEKFKGRVTI  TADKSTSTAY  MELSSLRSED  TAVYYCAREN
YGSHGGFVYW  GQGTLVTVSSASTKGPSVFP  LAPSSKSTSG  GTAALGCLVK
DYFPEPVTVS  WNSGALTSGV  HTFPAVLQSS  GLYSLSSVVT  VPSSSLGTQT
YICNVNHKPS  NTKVDKKVEP  KSCDKTHTCP  PCPAPELLGG  PSVFLFPPKP
KDTLMISRTP  EVTCVVVDVS  HEDPEVKFNW  YVDGVEVHNA  KTKPREEQYN
STYRVVSVLT  VLHQDWLNGK  EYKCKVSNKA  LPAPIEKTIS  KAKGQPREPQ
VYTLPPSRDE  LTKNQVSLTC  LVKGFYPSDI  AVEWESNGQP  ENNYKTTPPV
LDSDGSFFLY  SKLTVDKSRW  QQGNVFSCSV  MHEALHNHYT  QKSLSLSPG
```

Figure 36
(a) 949gH20b heavy chain (V + constant – hu IgG1 delta Lys, exons underlined) (SEQ ID NO:81)

<u>gaagtgcagc ttgtgcaaag cggcgctgag gtcaaaaagc ccggatcaag</u>
<u>cgtgaaagtc tcatgcaaag ccagcggcta caccttcaca acgtaccta</u>
<u>tcgagtgggt gaggcaggct cccggccaag gactggaatg gatggggaac</u>
<u>ttccacccat acaacgacga caccaagtac aacgagaagt tcaaggggcg</u>
<u>cgttactata accgccgaca agagcactag caccgcctac atggagctga</u>
<u>gcagtctgag aagcgaggat acagccgtgt actattgtgc acgggagaat</u>
<u>tatggctctc acggcggatt tgtgtactgg ggccaaggaa cactggttac</u>
<u>tgtctcgagc</u> gcttctacaa agggcccatc ggtcttcccc ctggcaccct
cctccaagag cacctctggg ggcacagcgg ccctgggctg cctggtcaag
gactacttcc ccgaaccggt gacggtgtcg tggaactcag gcgccctgac
cagcggcgtg cacaccttcc cggctgtcct acagtcctca ggactctact
ccctcagcag cgtggtgacc gtgccctcca gcagcttggg cacccagacc
tacatctgca acgtgaatca caagcccagc aacaccaagg tggacaagaa
agttggtgag aggccagcac agggagggag ggtgtctgct ggaagccagg
ctcagcgctc ctgcctggac gcatcccggc tatgcagccc cagtccaggg
cagcaaggca ggccccgtct gcctcttcac ccggaggcct ctgcccgccc
cactcatgct cagggagagg gtcttctggc tttttcccca ggctctgggc
aggcacaggc taggtgcccc taacccaggc cctgcacaca aaggggcagg
tgctgggctc agacctgcca agagccatat ccgggaggac cctgccctg
acctaagccc accccaaagg ccaaactctc cactccctca gctcggacac
cttctctcct cccagatctg agtaactccc aatcttctct ctgcag<u>agcc</u>
<u>caaatcttgt gacaaaactc acacatgccc accgtgccca</u> ggtaagccag
cccaggcctc gccctccagc tcaaggcggg acaggtgccc tagagtagcc
tgcatccagg gacaggcccc agccgggtgc tgacacgtcc acctccatct
cttcctcagc acctgaactc ctggggggac cgtcagtctt cctcttcccc
ccaaaaccca aggacaccct catgatctcc cggacccctg aggtcacatg
cgtggtggtg gacgtgagcc acgaagaccc tgaggtcaag ttcaactggt
acgtggacgg cgtggaggtg cataatgcca agacaaagcc gcgggaggag
cagtacaaca gcacgtaccg tgtggtcagc gtcctcaccg tcctgcacca

Figure 36 continued

```
ggactggctg aatggcaagg agtacaagtg caaggtctcc aacaaagccc
tcccagcccc catcgagaaa accatctcca agccaaagg tgggacccgt
ggggtgcgag ggccacatgg acagaggccg gctcggccca ccctctgccc
tgagagtgac cgctgtacca acctctgtcc ctacagggca gccccgagaa
ccacaggtgt acaccctgcc cccatcccgg gatgagctga ccaagaacca
ggtcagcctg acctgcctgg tcaaaggctt ctatcccagc gacatcgccg
tggagtggga gagcaatggg cagccggaga acaactacaa gaccacgcct
cccgtgctgg actccgacgg ctccttcttc ctctacagca agctcaccgt
ggacaagagc aggtggcagc aggggaacgt cttctcatgc tccgtgatgc
atgaggctct gcacaaccac tacacgcaga agagcctctc cctgtctccg
ggt
```

Figure 37
(a) 949gH20b heavy chain (V + constant – hu IgG1 delta Lys) with signal sequence underlined and italicized (SEQ ID NO:82)

```
MEWSWVFLFF LSVTTGVHSE VQLVQSGAEV KKPGSSVKVS CKASGYTFTT
YPIEWVRQAP GQGLEWMGNF HPYNDDTKYN EKFKGRVTIT ADKSTSTAYM
ELSSLRSEDT AVYYCARENY GSHGGFVYWG QGTLVTVSSASTKGPSVFPL
APSSKSTSGG TAALGCLVKD YFPEPVTVSW NSGALTSGVH TFPAVLQSSG
LYSLSSVVTV PSSSLGTQTY ICNVNHKPSN TKVDKKVEPK SCDKTHTCPP
CPAPELLGGP SVFLFPPKPK DTLMISRTPE VTCVVVDVSH EDPEVKFNWY
VDGVEVHNAK TKPREEQYNS TYRVVSVLTV LHQDWLNGKE YKCKVSNKAL
PAPIEKTISK AKGQPREPQV YTLPPSRDEL TKNQVSLTCL VKGFYPSDIA
VEWESNGQPE NNYKTTPPVL DSDGSFFLYS KLTVDKSRWQ QGNVFSCSVM
HEALHNHYTQ KSLSLSPG
```

Figure 38
(a) 949gH20b heavy chain (V + constant – hu IgG1 delta Lys, exons underlined) with signal sequence underlined and italicised (SEQ ID NO: 83)

```
atggagtggt cctgggtgtt tctcttcttt ctctccgtca caacgggtgt
tcatagcgaa gtgcagcttg tgcaaagcgg cgctgaggtc aaaaagcccg
gatcaagcgt gaaagtctca tgcaaagcca gcggctacac cttcacaacg
tacccatcg agtgggtgag gcaggctccc ggccaaggac tggaatggat
ggggaacttc acccataca acgacgacac caagtacaac gagaagttca
aggggcgcgt tactataacc gccgacaaga gcactagcac cgcctacatg
gagctgagca gtctgagaag cgaggataca gccgtgtact attgtgcacg
ggagaattat ggctctcacg gcggatttgt gtactggggc caaggaacac
tggttactgt ctcgagcgct tctacaaagg gcccatcggt cttcccctg
gcaccctcct ccaagagcac ctctgggggc acagcggccc tgggctgcct
ggtcaaggac tacttccccg aaccggtgac ggtgtcgtgg aactcaggcg
ccctgaccag cggcgtgcac accttcccgg ctgtcctaca gtcctcagga
ctctactccc tcagcagcgt ggtgaccgtg ccctccagca gcttgggcac
ccagacctac atctgcaacg tgaatcacaa gcccagcaac accaaggtgg
acaagaaagt tggtgagagg ccagcacagg gagggagggt gtctgctgga
agccaggctc agcgctcctg cctggacgca tcccggctat gcagcccag
tccagggcag caaggcaggc cccgtctgcc tcttcacccg gaggcctctg
cccgccccac tcatgctcag ggagagggtc ttctggcttt ttccccaggc
tctgggcagg cacaggctag tgccctaa cccaggccct gcacacaaag
gggcaggtgc tgggctcaga cctgccaaga gccatatccg ggaggaccct
gcccctgacc taagcccacc ccaaaggcca actctccac tccctcagct
cggacacctt ctctcctccc agatctgagt aactcccaat cttctctctg
cagagcccaa atcttgtgac aaaactcaca catgcccacc gtgcccaggt
aagccagccc aggcctcgcc ctccagctca aggcgggaca ggtgccctag
agtagcctgc atccagggac aggccccagc cgggtgctga cacgtccacc
tccatctctt cctcagcacc tgaactcctg ggggaccgt cagtcttcct
cttcccccca aacccaagg acacctcat gatctccgg acccctgagg
tcacatgcgt ggtggtggac gtgagccacg aagaccctga ggtcaagttc
aactggtacg tggacggcgt ggaggtgcat aatgccaaga caaagccgcg
```

Figure 38 continued

```
ggaggagcag tacaacagca cgtaccgtgt ggtcagcgtc ctcaccgtcc
tgcaccagga ctggctgaat ggcaaggagt acaagtgcaa ggtctccaac
aaagccctcc cagcccccat cgagaaaacc atctccaaag ccaaaggtgg
gacccgtggg gtgcgagggc cacatggaca gaggccggct cggcccaccc
tctgccctga gagtgaccgc tgtaccaacc tctgtcccta cagggcagcc
ccgagaacca caggtgtaca ccctgccccc atcccgggat gagctgacca
agaaccaggt cagcctgacc tgcctggtca aaggcttcta tcccagcgac
atcgccgtgg agtgggagag caatgggcag ccggagaaca actacaagac
cacgcctccc gtgctggact ccgacggctc cttcttcctc tacagcaagc
tcaccgtgga caagagcagg tggcagcagg ggaacgtctt ctcatgctcc
gtgatgcatg aggctctgca caaccactac acgcagaaga gcctctccct
gtctccgggt
```

Figure 42
a)
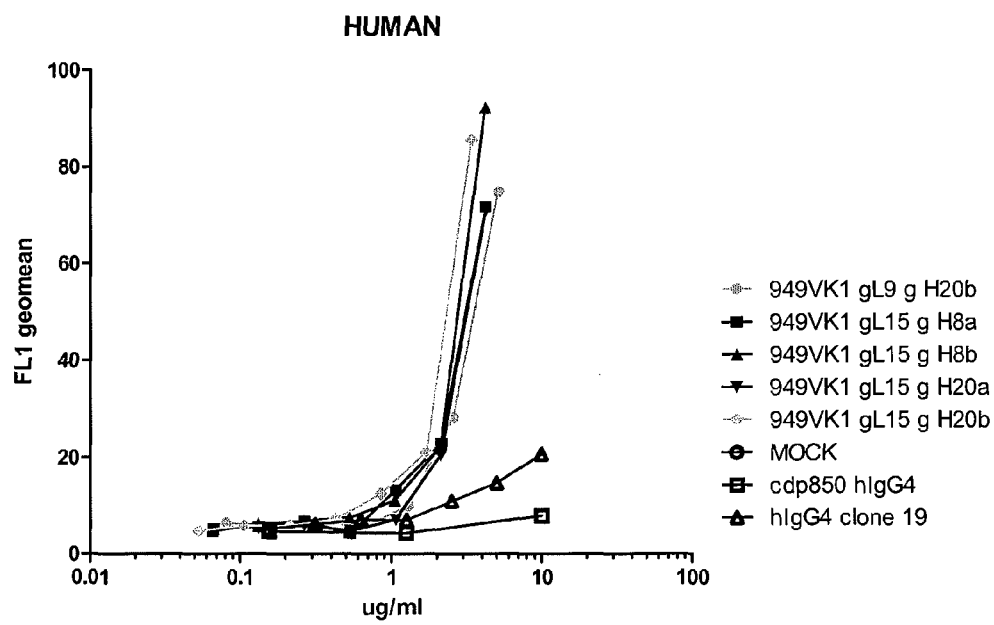
b)
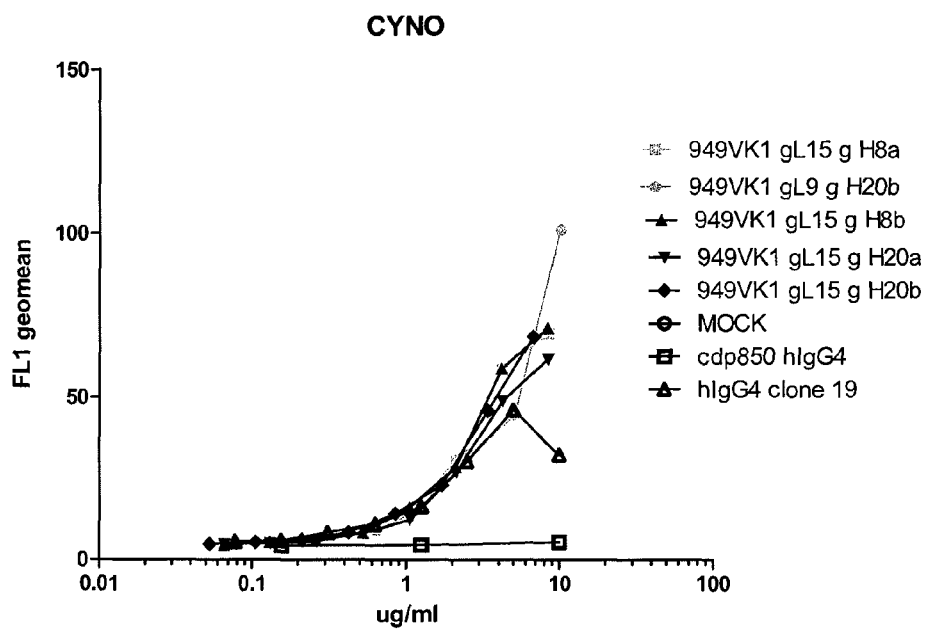

Figure 43

VK1 LIGHT CHAIN Graft 949

```
                   1       5      10      15      20      25      30 a    35      40      45      50      55      60      65      70      75      80      85      90      95     100     105
Light 949          ENVLTQSPAIMSASPGEKVTMTCRASSSVISSYLHWYQQKSGASPKLWIYSTSNLASGVPDRFSGSGSGTSYSLTISSVEAEDAATYYCQQYNGYPLITFGAGTKLEIK
                   ||||   ||||   ||||   ||||   ||||          ||||   ||||   ||||   ||||   ||||   ||||   ||||   ||||   ||||   ||||   ||||   ||||   ||||   ||||   ||||   ||
VK1 2-1-(1) L23    AIRMTQSPSSLSASVGDRVTITCWASQGISS-YLAWYQQKPAKAPKLFIYYASSLQSGVPSRFSGSGSGTDYTLTISSLQPEDFATYYCQQYSTPLITFGQGTKVEIK
                   ||||

949 VK1 gL1        ENVLTQSPSSLSASVGDRVTITCRASSSVISSYLHWYQQKPAKAPKLWIYSTSNLASGVPDRFSGSGSGTDYTLTISSLQPEDFATYYCQQYNGYPLITFGQGTKVEIK
949 VK1 gL9        ENVLTQSPSSLSASVGDRVTITCRASSSVISSYLHWYQQKPAKAPKLWIYSTSNLASGVPDRFSGSGSGTDYTLTISSLQPEDFATYYCQQYNGYPLITFGQGTKVEIK
949 VK1 gL11       ENVLTQSPSSLSASVGDRVTITCRASSSVISSYLHWYQQKPAKAPKLWIYSTSNLASGVPDRFSGSGSGTSYTLTISSLQPEDFATYYCQQYNGYPLITFGQGTKVEIK
949 VK1 gL12       ENVMTQSPSSLSASVGDRVTITCRASSSVISSYLHWYQQKPAKAPKLFIYSTSNLASGVPSRFSGSGSGTDYTLTISSLQPEDFATYYCQQYNSYPLITFGQGTKVEIK
949 VK1 gL14       ENVMTQSPSSLSASVGDRVTITCRASSSVISSYLHWYQQKPAKAPKLFIYSTSNLASGVPSRFSGSGSGTDYTLTISSLQPEDFATYYCQQYNSYPLITFGQGTKVEIK
949 VK1 gL15       ENVLTQSPSSLSASVGDRVTITCRASSSVISSYLHWYQQKPAKAPKLFIYSTSNLASGVPSRFSGSGSGTDYTLTISSLQPEDFATYYCQQYNSYPLITFGQGTKVEIK
```

VK3 LIGHT CHAIN Graft 949

```
                   1       5      10      15      20      25      30 a    35      40      45      50      55      60      65      70      75      80      85      90      95     100     105
Light 949          ENVLTQSPAIMSASPGEKVTMTCRASSSVISSYLHWYQQKSGASPKLWIYSTSNLASGVPDRFSGSGSGTSYSLTISSVEAEDAATYYCQQYNGYPLITFGAGTKLEIK
                   —
VK3 6-1-(1) A27    EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIK 949 VK3 gL1        ENVLTQSPGTLSLSPGERATLSCRASSSVISSYLHWYQQKPGQAPRLWIYSTSNLASGVPDRFSGSGSGTSYTLTISRLEPEDFATYYCQQYNGYPLITFGQGTKVEIK
949 VK3 gL11       ENVLTQSPGTLSLSPGERATLSCRASSSVISSYLHWYQQKPGQAPRLWIYSTSNLASGVPDRFSGSGSGTSYTLTISRLEPEDFATYYCQQYNGYPLITFGQGTKVEIK
```

Legend

949 = Mouse variable light chain sequence
949 VK1 gL = Humanized grafts of 949 variable light chain using VK1 2-1-(1) L23 human germline as the acceptor framework
949 VK3 gL = Humanized grafts of 949 variable light chain using VK3 6-1-(1) A27 human germline as the acceptor framework
CDRs are shown in bold/underlined For 949 VK1 light chain, donor residues are shown in bold/italic and are highlighted: E1, N2, V3, L4, W47, D60 and S70
For 949 VK3 light chain, donor residues are shown in bold/italic and are highlighted: N2, W47, V58, S70, Y71 and T85

PD-1 ANTIBODIES

CROSS-REFERENCE TO RELATED APPLICATIONS

This application claims priority to U.S. Application Ser. No. 61/312,702, filed on Mar. 11, 2010, under 35 U.S.C. §119(e), which is incorporated by reference in its entirety.

FIELD OF THE INVENTION

The present invention relates to antibody molecules having specificity for antigenic determinants of human PD-1 and compositions comprising the same. The present invention also relates to the therapeutic uses of the antibody molecules, compositions and methods for producing said antibody molecules.

BACKGROUND OF THE INVENTION

Programmed Death 1 (PD-1), also known as CD279; gene name PDCD1; accession number NP_005009 is a cell surface receptor with a critical role in regulating the balance between stimulatory and inhibitory signals in the immune system and maintaining peripheral tolerance (Ishida, Y et al. 1992 EMBO J 11 3887; Kier, Mary E et al. 2008 Annu Rev Immunol 26 677-704; Okazaki, Taku et al. 2007 International Immunology 19 813-824). It is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signaling (Kier, Mary E et al. 2008 Annu Rev Immunol 26 677-704; Agata, Y et al 1996 Int Immunol 8 765-72). PD-1 has two known ligands, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2 261). Upon ligand engagement, PD-1 recruits phosphatases such as SHP-1 and SHP-2 to its intracellular tyrosine motifs which subsequently dephosphorylate effector molecules activated by TCR or BCR signaling (Chemnitz, J et al. 2004 J Immunol 173 945-954; Riley, James L 2009 Immunological Reviews 229 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of anergy or unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-$_{XL}$ (Kier, Mary E et al. 2008 Annu Rev Immunol 26 677-704). In addition to these direct effects, recent publications have implicated PD-1 as being involved in the suppression of effector cells by promoting the induction and maintenance of regulatory T cells ($T_{REG}$). For example, PD-L1 expressed on dendritic cells was shown to act in synergy with TGF-β to promote the induction of $CD4^+$ $FoxP3^+$ $T_{REG}$ with enhanced suppressor function (Francisco, Loise M et al. 2009 J Exp Med 206 3015-3029).

The first indication of the importance of PD-1 in peripheral tolerance and inflammatory disease came from the observation that PD-1 knockout (Pdcd1$^{-/-}$) mice develop spontaneous autoimmunity. Fifty percent of Pdcd1$^{-/-}$ mice on a C57BL/6 background develop lupus-like glomerulonephritis and arthritis by 14 months of age and BALB/c-Pdcd1$^{-/-}$ mice develop a fatal dilated cardiomyopathy and production of autoantibodies against cardiac troponin I from 5 weeks onwards (Nishimura, H et al. 1999 Immunity 11 141-151; Nishimura, H et al. 2001 Science 291 319-322). Furthermore, introduction of PD-1 deficiency to the non-obese diabetic (NOD) mouse strain dramatically accelerates the onset and incidence of diabetes resulting in all NOD-Pdcd1$^{-/-}$ mice developing diabetes by 10 weeks of age (Wang, J et al. 2005 Proc Natl Acad Sci USA 102 11823). Additionally, using induced murine models of autoimmunity such as experimental autoimmune encephalomyelitis (EAE), or transplantation/graft-versus-host (GVHD) models, several groups have shown that blocking the PD-1-PD-L interaction exacerbates disease, further confirming the key role of PD-1 in inflammatory diseases. Importantly, evidence suggests that PD-1 has a comparable immune modulatory function in humans as mice, as polymorphisms in human PDCD1 have been associated with a range of autoimmune diseases including systemic lupus erythematosus (SLE), multiple sclerosis (MS), type I diabetes (TID), rheumatoid arthritis (RA) and Grave's disease (Okazaki, Taku et al. 2007 International Immunology 19 813-824; Prokunina, L et al. 2002 Nat Genet 32 666-669; Kroner, A et al. 2005 Ann Neurol 58 50-57; Prokunina, L et al 2004 Arthritis Rheum 50 1770).

Several therapeutic approaches to enhance PD-1 signaling and modulate inflammatory disease have been reported, using murine models of autoimmunity. One such approach tried was to generate artificial dendritic cells which over-express PD-L1. Injection of mice with antigen-loaded PD-L1-dendritic cells before or after induction of EAE by MOG peptide immunisation reduced the inflammation of the spinal cord as well as the clinical severity of the disease (Hirata, S et al. 2005 J Immunol 174 1888-1897). Another approach was to try to cure lupus-like syndrome in BXSB mice by delivering a PD-1 signal using a recombinant adenovirus expressing mouse PD-L1. Injection of this virus partially prevented the development of nephritis as shown by lower frequency of proteinuria, reduced serum anti-dsDNA Ig and better renal pathology (Ding, H et al. 2006 Clin Immunol 118 258). These results suggest that enhancing the PD-1 signal could have therapeutic benefit in human autoimmune disease. An alternative therapeutic approach more appropriate as a human drug treatment would be to use an agonistic monoclonal antibody against human PD-1. Binding of this agonistic antibody would ideally independently transduce inhibitory signals through PD-1 whilst also synergising with ongoing endogenous signals emanating from the natural PD-1-PD1-L interaction. An agonistic anti-PD-1 mAb would be predicted to modulate a range of immune cell types involved in inflammatory disease including T cells, B cells, NK cells and monocytes and would therefore have utility in the treatment of a wide range of human autoimmune or inflammatory disorders.

Whilst a number of antagonistic anti-PD-1 antibodies have been described, to date the only PD-1 agonistic antibodies described in the literature, to the best of the inventors knowledge, still also block the PD-1-PD1L and PD1-PD2L interaction. See for Example, WO2004/056875.

Accordingly there is still a need in the art for improved agonistic anti-PD-1 antibodies suitable for treating patients, in particular those which do not block the PD1-PDL1 or the PD1-PDL2 interaction.

We have now identified high affinity agonistic anti-PD-1 antibodies suitable for use in the treatment or prophylaxis of immune disorders, for example by reducing the T cell response. Non limiting examples of immune disorders that can be treated via the administration of PD-1 specific antibodies to a subject include, but are not limited to, rheumatoid arthritis, multiple sclerosis, inflammatory bowel disease, Crohn's disease, systemic lupus erythematosus, type I diabetes, transplant rejection, graft-versus-host disease, hyperproliferative immune disorders, cancer and infectious diseases.

BRIEF DESCRIPTION OF THE DRAWINGS

FIG. 1 shows amino acid sequences relating to antibody 949 according to the disclosure FIGS. 2-12 shows certain amino acid or DNA sequences relating to an antibody according to the disclosure

FIG. 17 shows an alignment of the light chains for the murine, acceptor frameworks and humanised light chains.

FIG. 18 shows an alignment of the heavy chains for the murine, acceptor frameworks and humanised heavy chains.

FIG. 19 shows an amino acid sequence of a heavy chain of antibody 949 in a huIgG4 format FIG. 20 shows a nucleic acid sequence of a heavy chain of antibody 949 in a huIgG4 format FIG. 21 shows an amino acid sequence of a heavy chain, including the signal sequence, of antibody 949 in a huIgG4 format FIG. 22 shows a nucleic acid sequence of a heavy chain, including the signal sequence, of antibody 949 in a huIgG4 format FIG. 23 shows an amino acid sequence of a heavy chain of antibody 949 in a huIgG1 format FIG. 24 shows a nucleic acid sequence of a heavy chain of antibody 949 in a huIgG1 format FIG. 25 shows an amino acid sequence of a heavy chain, including the signal sequence, of antibody 949 in a huIgG1 format FIG. 26 shows a nucleic acid sequence of a heavy chain, including the signal sequence, of antibody 949 in a huIgG1 format FIGS. 27 to 30 show various amino acid or nucleotide sequences for a variable region wherein CDR3 has been amended to remove a deamidation site.

FIGS. 31 to 38 show various amino acid or nucleotide sequences for a variable region, and variable region plus constant region.

FIGS. 42a) and b) show the cross-reactivity of various antibody constructs with human PD-1 and cyno PD-1

FIG. 43 shows an alignment of the light chains for the murine, acceptor frameworks and humanised light chains

DETAILED DESCRIPTION OF THE INVENTION

Figure 13:
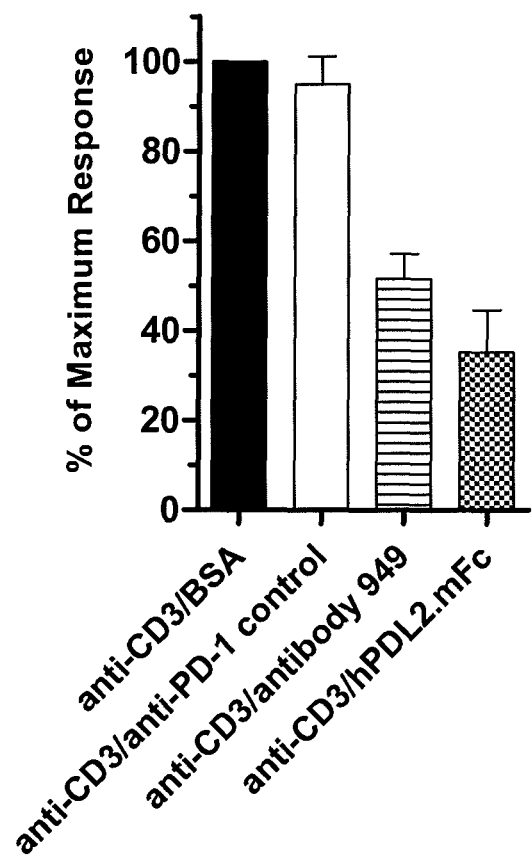
FIG. 13 shows Inhibition of human $CD4^+$ T cell proliferation by antibody 949.

The parental murine antibody hybridoma from which the humanised antibodies are derived is referred to herein as Clone 19. The cloned recombinant antibody derived from Clone 19 is referred to herein as antibody CA051_00949 also referred to herein as 949.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'agonistic antibody' describes an antibody that is capable of stimulating the biological signaling activity of PD-1, leading to phosphatase recruitment to its intracellular domain and hence inactivation of T or B cell receptor signaling and phenotypic characteristics associated with activation.

Antibodies for use in the present invention may be obtained using any suitable method known in the art. The PD-1 polypeptide/protein including fusion proteins, for example PD-1-Fc fusions proteins or cells (recombinantly or naturally) expressing the polypeptide (such as activated T cells) can be used to produce antibodies which specifically recognise PD-1. The PD-1 polypeptide may be the 'mature' polypeptide or a biologically active fragment or derivative thereof. Suitably the PD-1 polypeptide is the mature human polypeptide or the extracellular domain or fragment thereof. The extracellular domain typically comprises amino acids 21-170 of the PD-1 protein (SWISS PROT entry Q15116). PD-1 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The PD-1 polypeptide may in some instances be part of a larger protein such as a fusion protein for example fused to an affinity tag. Antibodies generated against the PD-1 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15): 7843-78481; WO92/02551; WO2004/051268 and International Patent Application number WO2004/106377.

Screening for antibodies can be performed using assays to measure binding to human PD-1 and/or assays to measure the ability to agonise PD1 activity. An example of a binding assay is an ELISA, in particular, using a fusion protein of human PD-1 and human Fc, which is immobilized on plates, and employing a conjungated secondary antibody to detect anti-PD-1 antibody bound to the fusion protein. Examples of suitable agonism and ligand blocking assays are described in the Examples herein.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

The present invention provides agonistic humanised antibodies having specificity for human PD-1.

An agonistic murine anti-PD-1 antibody (Clone 19) was described in PCT/IB2009/06940 (unpublished) and the sequences of the variable regions and CDRs of this antibody are provided in FIG. 1. In particular the CDRs of this antibody are provided in FIG. 1(c), SEQ ID NOs 1-6.

An improved version of the CDRL3 (SEQ ID NO:6) derived from Clone 19 is provided in FIG. 2(a) (SEQ ID NO:7) in which a potential deamidation site has been modified. Accordingly, in one embodiment the present invention provides a humanised agonistic antibody which binds human PD-1 comprising a heavy chain and a light chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the variable domain of the light chain comprises the sequence given in SEQ ID NO:4 for CDR-L1, the sequence given in SEQ ID NO:5 for CDR-L2 and the sequence given in SEQ ID NO:7 for CDR-L3.

As used herein, the term 'humanised antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the Humanised antibody according to the present invention has a variable domain comprising human acceptor framework regions as well as one or more of the CDRs provided in FIG. 1(c) or FIG. 2(a). Thus, provided in one embodiment is an agonistic humanised antibody which binds human PD-1 wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

One such suitable framework region for the heavy chain of the humanised antibody of the present invention is derived from the human sub-group VH1 sequence 1-3 1-46 together with JH4 (SEQ ID NO:52). Accordingly, in one example there is provided an agonistic humanised antibody comprising the sequence given in SEQ ID NO:1 for CDR-H1, the sequence given in SEQ ID NO:2 for CDR-H2 and the sequence given in SEQ ID NO:3 for CDRH3 wherein the heavy chain framework region is derived from the human subgroup VH1 sequence 1-3 1-46 together with JH4. The sequence of human JH4 is as follows: (YFDY) WGQGTLVTVS (Seq ID No: 56). The YFDY motif is part of CDR-H3 and is not part of framework 4 (Ravetch, J V. et al., 1981, Cell, 27, 583-591).

Another suitable framework region for the heavy chain of the humanised antibody of the present invention is derived from the human sub-group VH1 sequence 1-2 1-e together with JH4 (SEQ ID NO:54). Accordingly, in one example there is provided an agonistic humanised antibody comprising the sequence given in SEQ ID NO:1 for CDR-H1, the sequence given in SEQ ID NO:2 for CDR-H2 and the sequence given in SEQ ID NO:3 for CDRH3 wherein the heavy chain framework region is derived from the human subgroup VH1 sequence 1-2 1-e together with JH4, see for example SEQ ID NO:46). The sequence of human JH4 is as follows: (YFDY)WGQGTLVTVS (Seq ID No: 56). The YFDY motif is part of CDR-H3 and is not part of framework 4 (Ravetch, J V. et al., 1981, Cell, 27, 583-591). In one example the heavy chain variable domain of the antibody comprises the sequence given in SEQ ID NO:46.

A suitable framework region for the light chain of the humanised antibody of the present invention is derived from the human germline sub-group VK1 sequence 2-1-(1) L23 together with JK4 (SEQ ID NO:48). Accordingly, in one example there is provided an agonistic humanised antibody comprising the sequence given in SEQ ID NO:4 for CDR-L1, the sequence given in SEQ ID NO:5 for CDR-L2 and the sequence given in SEQ ID NO:6 or SEQ ID NO:7 for CDRL3 wherein the light chain framework region is derived from the human subgroup sequence 2-1-(1) L23 together with JK4. The JK4 sequence is as follows: (LT)FGGGTKVEIK (Seq ID No: 57). The LT motif is part of CDR-L3 and is not part of framework 4 (Hieter, P A., et al., 1982, J. Biol. Chem., 257, 1516-1522).

Another suitable framework region for the light chain of the humanised antibody of the present invention is derived from the human germline sub-group VK3 sequence 6-1-(1) A27 together with JK4 (SEQ ID NO:50). Accordingly, in one example there is provided an agonistic humanised antibody comprising the sequence given in SEQ ID NO:4 for CDR-L1, the sequence given in SEQ ID NO:5 for CDR-L2 and the sequence given in SEQ ID NO:6 or SEQ ID NO:7 for CDRL3 wherein the light chain framework region is derived from the human subgroup sequence VK3 6-1-(1) A27 together with JK4. The JK4 sequence is as follows: (LT)FGGGTKVEIK (Seq ID No: 57). The LT motif is part of CDR-L3 and is not part of framework 4 (Hieter, P A., et al., 1982, J. Biol. Chem., 257, 1516-1522).

Also, in a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Suitably, in a humanised antibody molecule of the present invention, if the acceptor heavy chain has the human VH1 sequence 1-3 1-46 together with JH4, then the acceptor framework regions of the heavy chain comprise, in addition to the three donor CDRs (SEQ ID NOs:1, 2 and 3), a donor residue at at least one of positions 25, 37, 41, 48, 71, 73 and 76 (according to Kabat et al., (supra)). Accordingly, in one example there is provided a humanised antibody, wherein at least the residues at each of positions 25, 37, 41, 48, 71, 73 and 76 of the variable domain of the heavy chain are donor residues, see for example the sequence given in SEQ ID NO:30. In one example there is provided a humanised antibody, wherein at least the residues at each of positions 25, 37, 41 and 48 of the variable domain of the heavy chain are donor residues, see for example the sequence given in SEQ ID NO:38. In one example there is provided a humanised antibody, wherein at least the residue at position 25 of the variable domain of the heavy chain is a donor residue, see for example the sequence given in SEQ ID NO: 40.

Suitably, in a humanised antibody molecule of the present invention, if the acceptor heavy chain has the human VH1 sequence 1-2 1-e together with JH4, then the acceptor framework regions of the heavy chain comprise, in addition to the three donor CDRs (SEQ ID NOs:1, 2 and 3), a donor residue at at least one of positions 25, 37, 41, 48, 71, 76 and 78 (according to Kabat et al., (supra)). Accordingly, in one example there is provided a humanised antibody, wherein at least the residues at each of positions 25, 37, 41, 48, 71, 76 and 78 of the variable domain of the heavy chain are donor residues, see for example the sequence given in SEQ ID NO:42. In one example there is provided a humanised antibody, wherein at least the residues at each of positions 25, 37, 41 and 48 of the variable domain of the heavy chain are donor residues, see for example the sequence given in SEQ ID NO:44.

Suitably, in a humanised antibody molecule according to the present invention, if the acceptor light chain has the human sub-group VK1 sequence 2-1-(1) L23 together with JK4, then the acceptor framework regions of the light chain comprise, in addition to three donor CDRs (SEQ ID NOs:4, 5 and 6 or 7), a donor residue at at least one of positions 1, 2, 3, 4, 47, 60 and 70. Accordingly, in one example there is provided a humanised antibody, wherein at least the residues at each of positions 1, 2, 3, 4, 47, 60 and 70 of the variable domain of the light chain are donor residues, see for example SEQ ID NO:10. In one example there is provided a humanised antibody, wherein at least the residues at each of positions 1, 2, 3, and 4 of the variable domain of the light chain are donor residues, see for example SEQ ID NO:18 or SEQ ID NO:20. In one embodiment the antibody comprises a sequence as shown in SEQ ID NO. 66. In one example there is provided a humanised antibody, wherein at least the residues at each of positions 1, 2 and 3 of the variable domain of the light chain are donor residues, see for example SEQ ID NO:22 or SEQ ID NO:24.

Suitably, in a humanised antibody molecule according to the present invention, if the acceptor light chain has the human sub-group VK3 sequence 6-1-(1) A27 together with JK4, then the acceptor framework regions of the light chain comprise, in addition to the three donor CDRs (SEQ ID NOs:4, 5 and 6 or 7), a donor residue at at least one of positions 2, 47, 58, 70, 71 and 85. Accordingly, in one example there is provided a humanised antibody, wherein at least the residues at each of positions 2, 47, 58, 70, 71 and 85 of the variable domain of the light chain are donor residues, see for example, SEQ ID NO:26 or SEQ ID NO:28.

Donor residues are residues from the donor antibody, i.e. the antibody from which the CDRs were originally derived. Donor residues may replace human acceptor framework residues (acceptor residues) at one or more of the positions listed below.

| VK1 Light chain 2-1(1) L23 | |
|---|---|
| Kabat position | Human acceptor residue |
| 1 | Alanine |
| 2 | Isoleucine |
| 3 | Arginine |
| 4 | Methionine |
| 47 | Phenylalanine |
| 60 | Serine |
| 70 | Aspartic acid |

| VK3 Light chain 6-1-(1) A27 | |
|---|---|
| Kabat position | Human acceptor residue |
| 2 | Isoleucine |
| 47 | Leucine |
| 58 | Isoleucine |
| 70 | Aspartic acid |
| 71 | Phenylalanine |
| 85 | Valine |

| VH1 Heavy chain 1-3 1-46 | |
|---|---|
| Kabat position | Human acceptor residue |
| 25 | Serine |
| 37 | Valine |
| 41 | Proline |
| 48 | Methionine |
| 71 | Arginine |
| 73 | Threonine |
| 76 | Serine |

| VH1 Heavy chain 1-2 1-e | |
|---|---|
| Kabat position | Human acceptor residue |
| 25 | Serine |
| 37 | Valine |
| 41 | Proline |
| 48 | Methionine |
| 71 | Alanine |
| 76 | Serine |
| 78 | Alanine |

The antibody molecules of the present invention suitably comprise a complementary light chain or a complementary heavy chain, respectively. Accordingly, in one embodiment the present invention provides a humanised agonistic antibody which binds human PD-1 having a heavy chain comprising a sequence selected from the group consisting of: SEQ ID NO:30, SEQ ID NO:38, SEQ ID NO:40, SEQ ID NO:42, SEQ ID NO:44 and SEQ ID NO:46 and a light chain comprising a sequence selected from the group consisting of SEQ ID NO: 10, SEQ ID NO:18, SEQ ID NO:20, SEQ ID NO:22, SEQ ID NO:24, SEQ ID NO:26 and SEQ ID NO:28.

The antibody molecules of the present invention suitably comprise a complementary light chain or a complementary heavy chain, respectively. Accordingly, in one embodiment the present invention provides a humanised agonistic antibody which binds human PD-1 having a heavy chain comprising a sequence selected from the group consisting of: SEQ ID NO:30, SEQ ID NO:38, SEQ ID NO:40, SEQ ID NO:42, SEQ ID NO:44 and SEQ ID NO:46 and a light chain comprising a sequence selected from the group consisting of SEQ ID NO: 10, SEQ ID NO:18, SEQ ID NO:20, SEQ ID NO:22, SEQ ID NO:24, SEQ ID NO:26, SEQ ID NO:28 and SEQ ID NO:66.

In one embodiment the heavy chain comprises a sequence selected from SEQ ID NO: 30 and SEQ ID NO: 46 and the light chain comprises a sequence according to SEQ ID NO: 66.

It will be appreciated that one or more amino acid substitutions, additions and/or deletions may be made to the CDRs or other sequences (e.g variable domains) provided by the present invention without significantly altering the ability of the antibody to bind to PD-1 and to agonise PD-1 activity. The effect of any amino acid substitutions, additions and/or deletions can be readily tested by one skilled in the art, for example by using the methods described herein, in particular in the Examples, to determine PD-1 binding and PD-1 agonism.

In another embodiment, an antibody of the present invention comprises a heavy chain, wherein the variable domain of the heavy chain comprises a sequence having at least 60% identity or similarity to the sequence given in any one of SEQ ID NO:30, SEQ ID NO:38, SEQ ID NO:40, SEQ ID NO:42, SEQ ID NO:44 or SEQ ID NO:46. In one embodiment, an antibody of the present invention comprises a heavy chain, wherein the variable domain of the heavy chain comprises a sequence having at least 70%, 80%, 90%, 95% or 98% identity or similarity to the sequence given in any one of SEQ ID NO:30, SEQ ID NO:38, SEQ ID NO:40, SEQ ID NO:42, SEQ ID NO:44 or SEQ ID NO:46.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:
phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In another embodiment, an antibody of the present invention comprises a light chain, wherein the variable domain of the light chain comprises a sequence having at least 60% identity or similarity to the sequence given in any one of SEQ ID NO: 10, SEQ ID NO:18, SEQ ID NO:20, SEQ ID NO:22, SEQ ID NO:24, SEQ ID NO:26 or SEQ ID NO:28

In one embodiment the antibody of the present invention comprises a light chain, wherein the variable domain of the light chain comprises a sequence having at least 70%, 80%, 90%, 95% or 98% identity or similarity to the sequence given in any one of SEQ ID NO: 10, SEQ ID NO:18, SEQ ID NO:20, SEQ ID NO:22, SEQ ID NO:24, SEQ ID NO:26 or SEQ ID NO:28.

In one embodiment the antibody of the present invention comprises a sequence having at least 70%, 80%, 90%, 95% or 98% identity or similarity to the sequence given herein, for example SEQ ID NO:66 or SEQ ID NO:70.

In one embodiment the antibody of the present invention comprises a sequence having at least 70%, 80%, 90%, 95% or 98% identity or similarity to the sequence given herein, for example SEQ ID NO: 34, SEQ ID NO:58, SEQ ID NO:62, SEQ ID NO:76 or SEQ ID NO:80.

In another embodiment of the invention, the antibody comprises a heavy chain and a light chain, wherein the variable domain of the heavy chain comprises a sequence having at least 60% identity or similarity to the sequence given in any one of SEQ ID NO:30, SEQ ID NO:38, SEQ ID NO:40, SEQ ID NO:42, SEQ ID NO:44 or SEQ ID NO:46 and the variable domain of the light chain comprises a sequence having at least 60% identity or similarity to the sequence given in any one of SEQ ID NO: 10, SEQ ID NO:18, SEQ ID NO:20, SEQ ID NO:22, SEQ ID NO:24, SEQ ID NO:26 or SEQ ID NO:28.

Suitably, the antibody comprises a heavy chain, wherein the variable domain of the heavy chain comprises a sequence having at least 70%, 80%, 90%, 95% or 98% identity or similarity to the sequence given in any one of SEQ ID NO:30, SEQ ID NO:38, SEQ ID NO:40, SEQ ID NO:42, SEQ ID NO:44 or SEQ ID NO:46 and a light chain, wherein the variable domain of the light chain comprises a sequence having at least 70%, 80%, 90%, 95% or 98% identity or similarity to the sequence given in any one of SEQ ID NO: 10, SEQ ID NO:18, SEQ ID NO:20, SEQ ID NO:22, SEQ ID NO:24, SEQ ID NO:26 or SEQ ID NO:28.

In another embodiment of the invention, the antibody comprises a heavy chain and a light chain, wherein the variable domain of the heavy chain comprises a sequence having at least 60% identity or similarity to the sequence given in any one of SEQ ID NO:30, SEQ ID NO:38, SEQ ID NO:40, SEQ ID NO:42, SEQ ID NO:44, SEQ ID NO:46, SEQ ID NO: 58, SEQ ID NO: 62, SEQ ID NO:76 or SEQ ID NO:80 and the variable domain of the light chain comprises a sequence having at least 60% identity or similarity to the sequence given in any one of SEQ ID NO: 10, SEQ ID NO:18, SEQ ID NO:20, SEQ ID NO:22, SEQ ID NO:24, SEQ ID NO:26, SEQ ID NO:28, SEQ ID NO:66 or SEQ ID NO:70.

Suitably, the antibody comprises a heavy chain, wherein the variable domain of the heavy chain comprises a sequence having at least 70%, 80%, 90%, 95% or 98% identity or similarity to the sequence given in any one of SEQ ID NO:30, SEQ ID NO:38, SEQ ID NO:40, SEQ ID NO:42, SEQ ID NO:44, SEQ ID NO:46, SEQ ID NO: 58, SEQ ID NO: 62, SEQ ID NO:76 or SEQ ID NO:80 and a light chain, wherein the variable domain of the light chain comprises a sequence having at least 70%, 80%, 90%, 95% or 98% identity or similarity to the sequence given in any one of SEQ ID NO: 10, SEQ ID NO:18, SEQ ID NO:20, SEQ ID NO:22, SEQ ID NO:24, SEQ ID NO:26, SEQ ID NO:28, SEQ ID NO: 66 or SEQ ID NO: 70.

The antibody molecules of the present invention may comprise a complete antibody molecule having full length heavy and light chains or a fragment thereof and may be, but are not limited to Fab, modified Fab, Fab', modified Fab', F(ab)$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment there is a provided a heavy chain selected from SEQ ID NO: 58, SEQ ID NO: 62, SEQ ID NO: 76 or SEQ ID NO:80 in combination with a light chain comprising SEQ ID NO: 66.

In one embodiment there is provided a heavy chain selected from SEQ ID NO: 58 in combination with a light chain comprising SEQ ID NO: 66.

In one embodiment there is provided a heavy chain selected from SEQ ID NO: 62 in combination with a light chain comprising SEQ ID NO: 66.

In one embodiment there is provided a heavy chain selected from SEQ ID NO: 76 in combination with a light chain comprising SEQ ID NO: 66.

In one embodiment there is provided a heavy chain selected from SEQ ID NO: 80 in combination with a light chain comprising SEQ ID NO: 66.

In one embodiment there is provided a heavy chain selected from SEQ ID NO: 58, SEQ ID NO: 62 or SEQ ID NO: 76 in combination with a light chain according to SEQ ID NO: 70.

In one embodiment there is provided a heavy chain selected from SEQ ID NO: 58 in combination with a light chain according to SEQ ID NO: 70.

In one embodiment there is provided a heavy chain selected from SEQ ID NO: 62 or in combination with a light chain according to SEQ ID NO: 70.

In one embodiment there is provided a heavy chain selected from SEQ ID NO: 76 in combination with a light chain according to SEQ ID NO: 70.

In one embodiment there is provided a heavy chain selected from SEQ ID NO: 80 in combination with a light chain according to SEQ ID NO: 70.

In one embodiment the antibody according to the present disclosure is provided as PD-1 binding antibody fusion protein which comprises an immunoglobulin moiety, for example a Fab or Fab' fragment, and one or two single domain antibodies (dAb) linked directly or indirectly thereto, for example as described in WO2009/040562.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply agonising PD-1 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). Accordingly, the C-terminal lysine of the antibody heavy chain, for example as given in FIG. 8(*a*), SEQ ID NO: 36, may be absent.

In one embodiment there is provided an antibody heavy chain comprising or consisting of a sequence as per SEQ ID NO:58.

In one embodiment there is provided an antibody heavy chain comprising or consisting of a sequence as per SEQ ID NO:62.

In one embodiment there is provided an antibody heavy chain comprising or consisting of a sequence as per SEQ ID NO:76.

In one embodiment there is provided an antibody heavy chain comprising or consisting of a sequence as per SEQ ID NO:80.

In one embodiment there is provided a light chain comprising or consisting of a sequence as per SEQ ID NO: 70.

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the PD-1 antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised PD-1 antibody engineered to have an isoelectric point, different to that of the originally identified antibody 949. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY http://www.expasy.ch/tools/pi_tool.html, and http://www.iut-arles.up.univ-mrs.fr/w3bb/d_abim/compo-p.html, may be used to predict the isoelectric point of the antibody or fragment.

The antibody molecules of the present invention suitably have a high binding affinity, in particular nanomolar. Affinity may be measured using any suitable method known in the art, including BIAcore, as described in the Examples herein, using isolated natural or recombinant PD-1 or a suitable fusion protein/polypeptide. In one example affinity is measured using recombinant human PD-1 extracellular domain as described in the Examples herein. In one example the recombinant human PD-1 extracellular domain used is a monomer. Suitably the antibody molecules of the present invention have a binding affinity for isolated human PD-1 of about 6 nM or better. In one embodiment the antibody molecule of the present invention has a binding affinity of about 5 nM or better. In one embodiment the antibody molecule of the present invention has a binding affinity of about 4 nM or better. In one embodiment the antibody molecule of the present invention has a binding affinity of about 3 nM or better. In one embodiment the present invention provides a humanised antibody with a binding affinity of about 5 nM or better.

It will be appreciated that the affinity of antibodies provided by the present invention may be altered using any suitable method known in the art. The present invention therefore also relates to variants of the antibody molecules of the present invention, which have an improved affinity for PD-1. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention agonise human PD-1 activity. Assays suitable for determining the ability of an antibody to agonise PD-1 are described in the Examples herein. In a preferred embodiment, the antibodies of the present invention do not block the interaction between PD-1 and its ligand PD-1 L. Suitable assays for determining whether antibodies block PD-1 interaction with its ligand PD-1L are described in the examples herein (Freeman, Gordon et al. 2000 J Exp Med 192 1027; Butte, Mannish et al, 2007 Immunity 27(1) 2007).

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), caliccheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin. Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington, D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

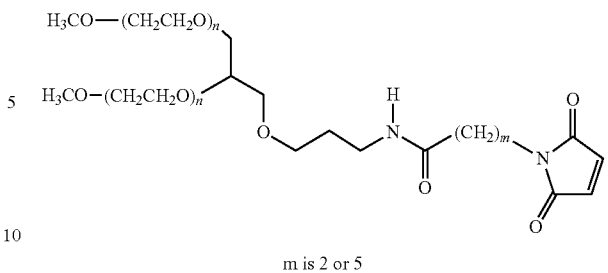

m is 2 or 5

That is to say each PEG is about 20,000 Da.
Further alternative PEG effector molecules of the following type:

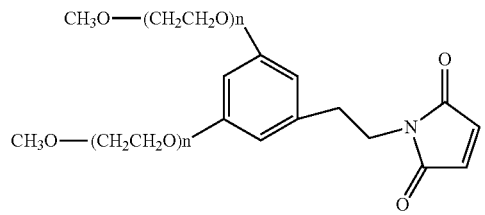

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof. DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in FIGS. 2-12, in particular SEQ ID NOs 11, 13, 15, 17, 19, 21, 23, 25, 27, 29, 31, 33, 35, 37, 39, 41, 43, 45 and 47.

Other examples of suitable DNA sequences are provided in FIGS. 20, 22, 24 and 26-38, in particular SEQ ID NO: 65, SEQ ID NO: 73, SEQ ID NO: 75, SEQ ID NO: 77, SEQ ID NO: 79, SEQ ID NO: 81 and SEQ ID NO: 83.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are optimised and conducive to commercial processing.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and for CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one embodiment the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

For example the formulation at approximately pH6 may comprise 1 to 50 mg/mL of antibody, 20 mM L-histidine HCl, 240 mM trehalose and 0.02% polysorbate 20. Alternatively a formulation at approximately pH 5.5 may comprise 1 to 50 mg/mL of antibody, 20 mM citrate buffer, 240 mM sucrose, 20 mM arginine, and 0.02% polysorbate 20.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody or fragment) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of inflammatory diseases, for example acute or chronic inflammatory disease. Suitably, the antibody molecule (or compositions comprising same) can be used to reduce the inflammatory process or to prevent the inflammatory process. In one embodiment there is provided an in vivo reduction of activated T cells, in particular those involved in inappropriate inflammatory immune responses, for example recruited to the vicinity/location of such a response.

Reduction of activated T cells, as employed herein, may be a reduction, 10, 20, 30, 40, 50, 60, 70, 80, 90 or more percent in comparison to before treatment or without treatment. Advantageously, treatment with an antibody, fragment or composition according to the present invention, may allow the reduction in the level of activated T cells, without reducing the patients general level of T cells (unactivated T cells). This may result in fewer side effects, and possibly prevent T cell depletion in the patient.

The present invention also provides the antibody molecule of the present invention for use in the treatment or prophylaxis of an immune disorder. The immune disorder, may, for example be selected from the group consisting of infections (viral, bacterial, fungal and parasitic), endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia, or infertility related to lack of fetal-maternal tolerance.

In one embodiment the antibody according to the invention is employed in the treatment of allergy, COPD, autoimmune disease or rheumatoid arthritis.

The present invention also provides an antibody molecule according to the present invention for use in the treatment or prophylaxis of pain, particularly pain associated with inflammation.

The present invention further provides the use of an antibody molecule, fragment or composition according to the present invention in the manufacture of a medicament for the treatment or prophylaxis of an immune disorder, in particular the immune disorder is rheumatoid arthritis, asthma or COPD.

The present invention further provides the use of an antibody molecule, fragment or composition according to the present invention in the manufacture of a medicament for the treatment or prophylaxis of one or more medical indications described herein.

An antibody molecule, fragment or composition of the present invention may be utilised in any therapy where it is desired to increase the effects of PD-1 in the human or animal body.

In one embodiment the antibody molecule of the present invention or a composition comprising the same is used for the control of inflammatory disease, e.g. as described herein.

The present invention also provides a method of treating human or animal subjects suffering from or at risk of an immune disorder, the method comprising administering to the subject an effective amount of the antibody molecule of the present invention, or a composition comprising the same.

In one embodiment there is provided a process for purifying an antibody (in particular an antibody or fragment according to the invention) comprising the steps:
performing anion exchange chromatography in non-binding mode such that the impurities are retained on the column and the antibody is eluted.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a dia filtration step.

Thus in one embodiment there is provided a purified anti-PD-1 antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

The antibody molecule of the present invention may also be used in diagnosis, for example in the in vivo diagnosis and imaging of disease states involving PD-1.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

EXAMPLES

FIG. 1 in detail:
a) Light chain V region of antibody 949 (SEQ ID NO:8)
b) Heavy chain V region of antibody 949 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody 949)

FIG. 2
a) Modified CDRL3 (deamidation site modified)
b) 949 VK1 gL1 V region (SEQ ID NO:10)
c) 949 VK1 gL1 V region DNA (SEQ ID NO:11)
d) 949 VK1 gL1 V region with signal sequence (SEQ ID NO:12)
e) 949 VK1 gL1 V region DNA with signal sequence (SEQ ID NO:13)
f) 949 VK1 gL1 light chain V+constant (SEQ ID NO:14)

FIG. 3
a) 949 VK1 gL1 light chain V+constant DNA (SEQ ID NO:15)
b) 949 VK1 gL1 light chain V+constant with signal sequence (SEQ ID NO:16)
c) 949 VK1 gL1 light chain V+constant DNA with signal sequence (SEQ ID NO:17)
d) 949 VK1 gL9 V region (SEQ ID NO:18)

FIG. 4
a) 949 VK1 gL9 V region DNA (SEQ ID NO:19)
b) 949 VK1 gL11 V region (SEQ ID NO:20)
c) 949 VK1 gL11 V region DNA (SEQ ID NO:21)
d) 949 VK1 gL12 V region (SEQ ID NO:22)
e) 949 VK1 gL12 V region DNA (SEQ ID NO:23)
f) 949 VK1 gL14 V region (SEQ ID NO:24)

FIG. 5
a) 949 VK1 gL14 V region DNA (SEQ ID NO:25)
b) 949 VK3 gL1 V region (SEQ ID NO:26)
c) 949 VK3 gL1 V region DNA (SEQ ID NO:27)
d) 949 VK3 gL11 V region (SEQ ID NO:28)
e) 949 VK3 gL11 V region DNA (SEQ ID NO:29)
f) 949 gH1a V region (SEQ ID NO:30)

FIG. 6
a) 949 gH1a V region DNA (SEQ ID NO:31)
b) 949 gH1a V region with signal sequence (SEQ ID NO:32)
c) 949 gH1a V region with signal sequence DNA (SEQ ID NO:33)
d) 949 gH1a V region and constant region (SEQ ID NO:34)

FIG. 7
a) 949 gH1a V region and constant region DNA (SEQ ID NO:35)

FIG. 8
a) 949 gH1a V region and constant region with signal sequence (SEQ ID NO:36)

FIG. 9
a) 949 gH1a V region and constant region with signal sequence DNA (SEQ ID NO:37)

FIG. 10
a) 949 gH8a V region (SEQ ID NO:38)
b) 949 gH8a V region DNA (SEQ ID NO:39)
c) 949 gH20a V region (SEQ ID NO:40)
d) 949 gH20a V region DNA (SEQ ID NO:41)
e) 949 gH1b V region (SEQ ID NO:42)
f) 949 gH1b V region (SEQ ID NO:43)

FIG. 11
a) 949 gH8b V region (SEQ ID NO:44)
b) 949 gH8b V region DNA (SEQ ID NO:45)
c) 949 gH20b V region (SEQ ID NO:46)
d) 949 gH20b V region DNA (SEQ ID NO:47)
e) Human VK1 2-1-(1) L23 JK4 acceptor framework (SEQ ID NO:48)
f) Human VK1 2-1-(1) L23 JK4 acceptor framework DNA (SEQ ID NO:49)

FIG. 12
a) Human VK3 6-1-(1) A27 JK4 acceptor framework (SEQ ID NO:50)
b) Human VK3 6-141) A27 JK4 acceptor framework DNA (SEQ ID NO:51)
c) Human VH1 1-3 1-46 JH4 acceptor framework (SEQ ID NO:52)
d) Human VH1 1-3 1-46 JH4 acceptor framework DNA (SEQ ID NO:53)
e) Human VH1 1-2 1-e JH4 acceptor framework (SEQ ID NO:54)
f) Human VH1 1-2 1-e JH4 acceptor framework DNA (SEQ ID NO:55)

FIG. 13 shows Inhibition of human CD4+ T cell proliferation by antibody 949. CD4+ T cells were purified from human PBMCs by negative selection and cultured with Dynalbeads coated with anti-CD3 plus control (BSA) or anti-PD-1 antibodies/recombinant PD-L2. Proliferation (y-axis) was measured by $^3$H-thymidine incorporation at day 6. Bars represent the % of maximal response (anti-CD3/BSA) and are the mean+/−S.E.M. of 4 different donor cultures.

Figure 14:
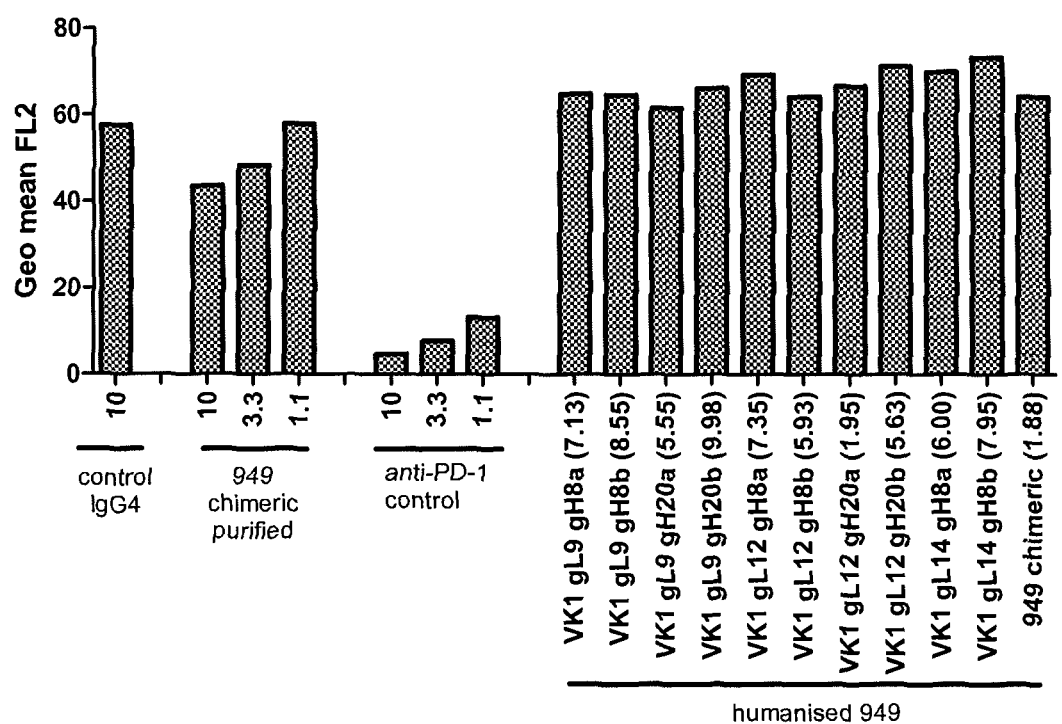
FIG. 14 Ligand blocking assay with antibody 949 and humanised versions.

FIG. 14 Ligand blocking assay with antibody 949. PD-1 expressing HEK293 cells were pre-incubated with purified chimeric 949 or humanised 949, or isotype matched positive and negative controls, followed by incubation with recombinant PD-L2. Blocking of PD-L2 to PD-1 by antibody 949 was assessed by revealing PD-L2 binding with an anti-mouse IgG H+L PE conjugated antibody. Figures in parentheses denote calculated concentration in μg/mL of humanised 949 added during the pre-incubation stage.

Figure 15:
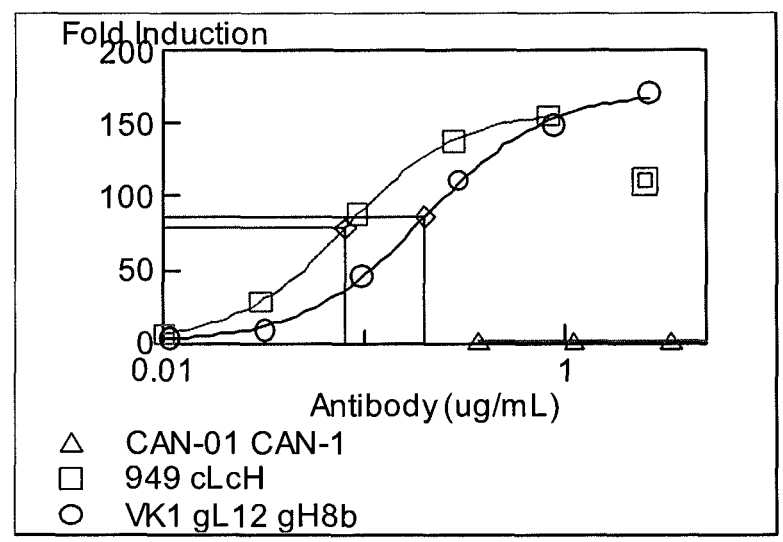
FIG. 15 Stimulation of SEAP from the human PD-1/CD28/Zeta reporter cell line by antibody 949.

FIG. 15 Stimulation of SEAP from the human PD-1/CD28/TCRζ SEAP reporter cell line by antibody 949. Dilutions of antibody were incubated with reporter cells and the released SEAP determined. Data was plotted as fold induction (signal/background signal).

Figure 16:
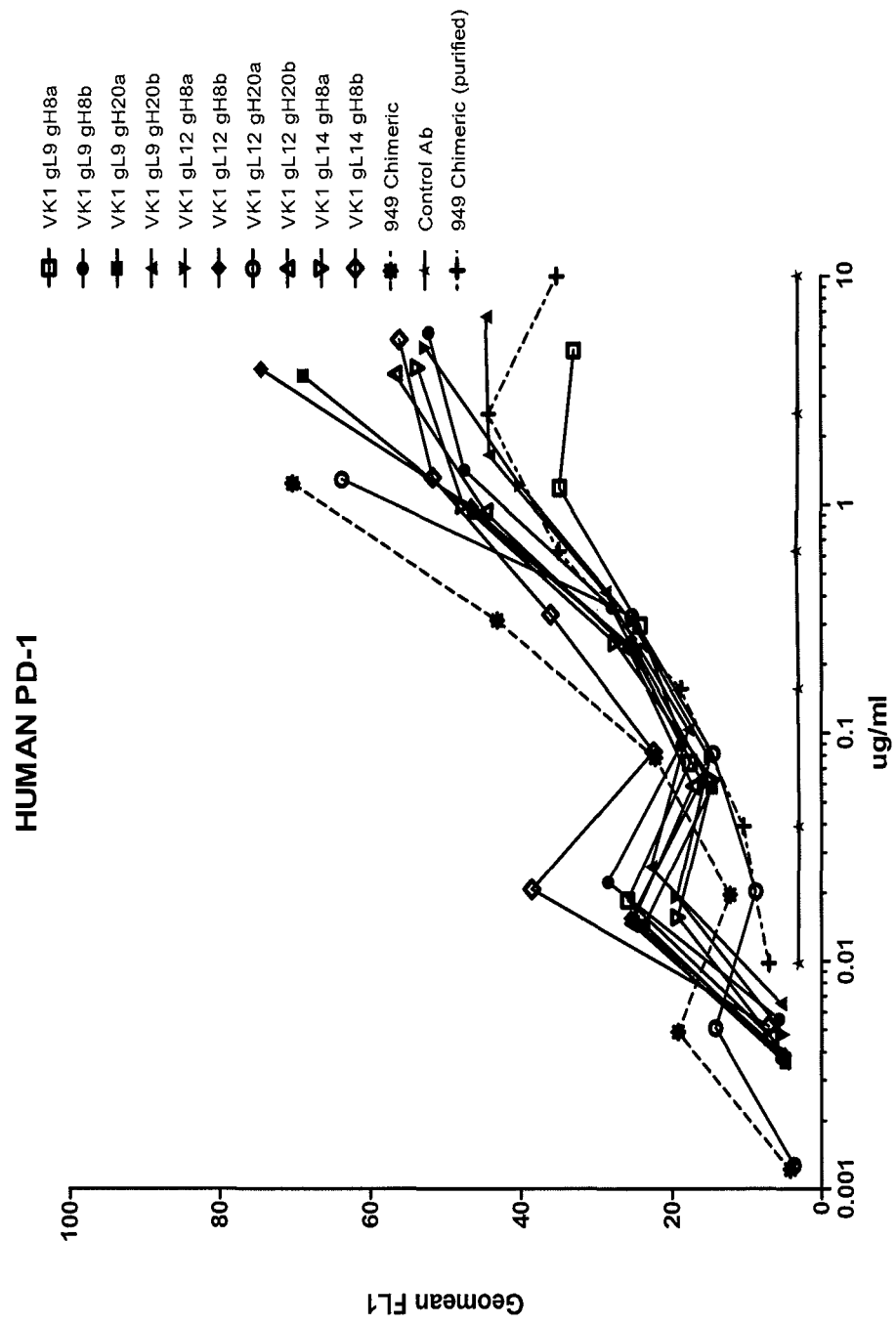
FIG. 16 Species Cross-reactivity of 949 chimeric and humanised grafts with PD-1

FIG. 16 Cross-reactivity of 949 chimeric and humanised grafts with PD-1 from Cynomolgus and Rhesus monkeys. Binding of 949 grafts to HEK293 cells transfected with empty vector (d), or PD-1 from human (a), cynomolgus (b) or rhesus (c) was measured by flow cytometry. Data is presented as geomean of PD-1 antibody associated fluorescence.

FIG. 17 shows an alignment of the light chains for the murine, acceptor frameworks and humanised light chains. CDRs are in bold and underlined. Donor residues are in bold, italic and are highlighted.

FIG. 18 shows an alignment of the heavy chains for the murine, acceptor frameworks and humanised heavy chains. CDRs are in bold and underlined. Donor residues are in bold, italic and are highlighted.

FIG. 19 shows 949gH1a heavy chain (V+constant–hu IgG4P delta Lys) (SEQ ID NO:58)

FIG. 20 949gH1a heavy chain (V+constant–hu IgG4P delta Lys, exons underlined) (SEQ ID NO:59)

FIG. 21 949gH1a heavy chain (V+constant–hu IgG4P delta Lys) with signal sequence underlined and italicised (SEQ ID NO: 60)

FIG. 22 949gH1a heavy chain (V+constant–hu IgG4P delta Lys, exons underlined) with signal sequence underlined and italicised (SEQ ID NO: 61)

FIG. 23 949gH1a heavy chain (V+constant–hu IgG1 delta Lys) (SEQ ID NO: 62)

FIG. 24 949gH1a heavy chain (V+constant–hu IgG1 delta Lys, exons underlined) (SEQ ID NO: 63)

FIG. 25 949gH1a heavy chain (V+constant–hu IgG1 delta Lys) with signal sequence underlined and italicised (SEQ ID NO:64)

FIG. 26 949gH1a heavy chain (V+constant–hu IgG1 delta Lys exons underlined) with signal sequence underlined and italicised (SEQ ID NO: 65)

FIG. 27
(a) 49 VK1 gL15 V-region amino acid and nucleic acid sequence and a corresponding amino acid sequence where a signal sequence is included. (SEQ ID NO: 66)
(b) 949 VK1 gL15 V-region (SEQ ID NO: 67)
(c) 949 VK1 gL15 V-region with signal sequence underlined and italicised (SEQ ID NO: 68)

FIG. 28
(a) 949 VK1 gL15 V-region nucleic acid sequence including a signal sequence. Also shown is an amino acid sequence of a light chain variable region and constant region. (SEQ ID NO: 69)
(b) 949 VK1 gL15 light chain (V+constant) (SEQ ID NO: 70)

FIG. 29
(a) 949VK1 gL15 light chain variable and constant region nucleic acid sequence. Also shown is a light chain amino acid sequence including a signal sequence. (SEQ ID NO: 71)
(b) 949 VK1 gL15 light chain with signal sequence underlined and italicised (SEQ ID NO: 72)

FIG. 30
(a) 949 VK1 gL15 light chain with signal sequence underlined and italicised (SEQ ID NO:73)

FIG. 31
(a) 949gH20b V-region with signal sequence underlined and italicized (SEQ ID NO:74)
(b) 949gH20b V-region with signal sequence underlined and italicized (SEQ ID NO: 75)
(c) 949gH20b heavy chain (V+constant–hu IgG4P delta Lys) (SEQ ID NO:76)

FIG. 32
(a) 949gH20b heavy chain (V+constant–hu IgG4P delta Lys) (SEQ ID NO:77)

FIG. 33
(a) 949gH20b heavy chain (V+constant–hu IgG4P delta Lys) with signal sequence underlined and italicized (SEQ ID NO: 78)

FIG. 34
(a) 949gH20b heavy chain (V+constant–hu IgG4P delta Lys, exons underlined) with signal sequence underlined and italicised (SEQ ID NO: 79)

FIG. 35
(a) 949gH20b heavy chain (V+constant–hu IgG1 delta Lys) (SEQ ID NO:80)

FIG. 36
(a) 949gH20b heavy chain (V+constant–hu IgG1 delta Lys, exons underlined) (SEQ ID NO:81)

FIG. 37
(a) 949gH20b heavy chain (V+constant–hu IgG1 delta Lys) with signal sequence underlined and italicized (SEQ ID NO:82)

FIG. 38
(a) 949gH20b heavy chain (V+constant–hu IgG1 delta Lys, exons underlined) with signal sequence underlined and italicised (SEQ ID NO: 83)

Figure 39:
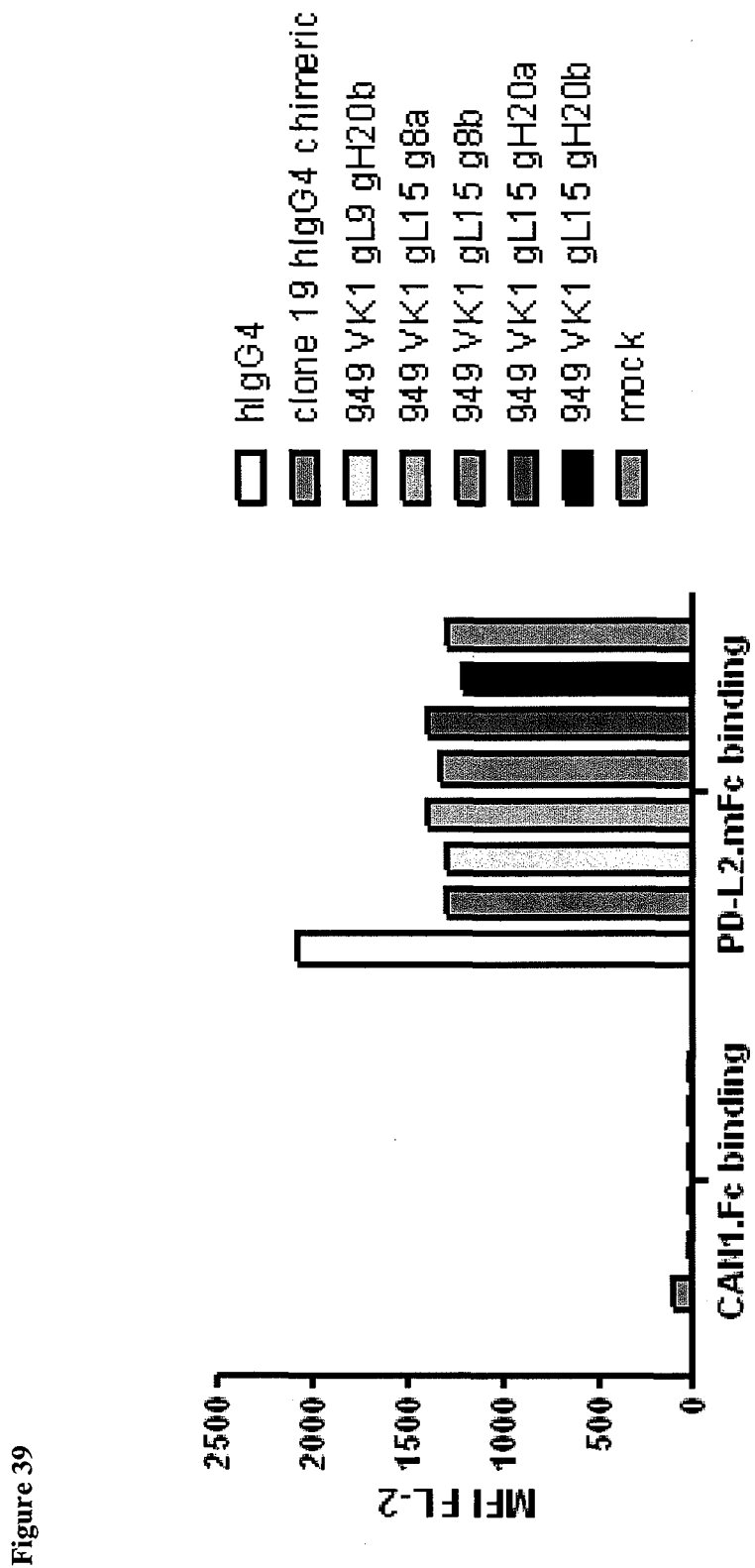
FIG. 39 shows the results of PD-1 ligand blocking binding assay.

FIG. 39 Ligand blocking binding assay for 949 VK1 gL9 gH20b, 949 VK1 gL15 g8a, 949 VK1 gL15 g8b, 949 VK1 gL15 gH20a, VK1 gL15 gH20b.

Figure 40:
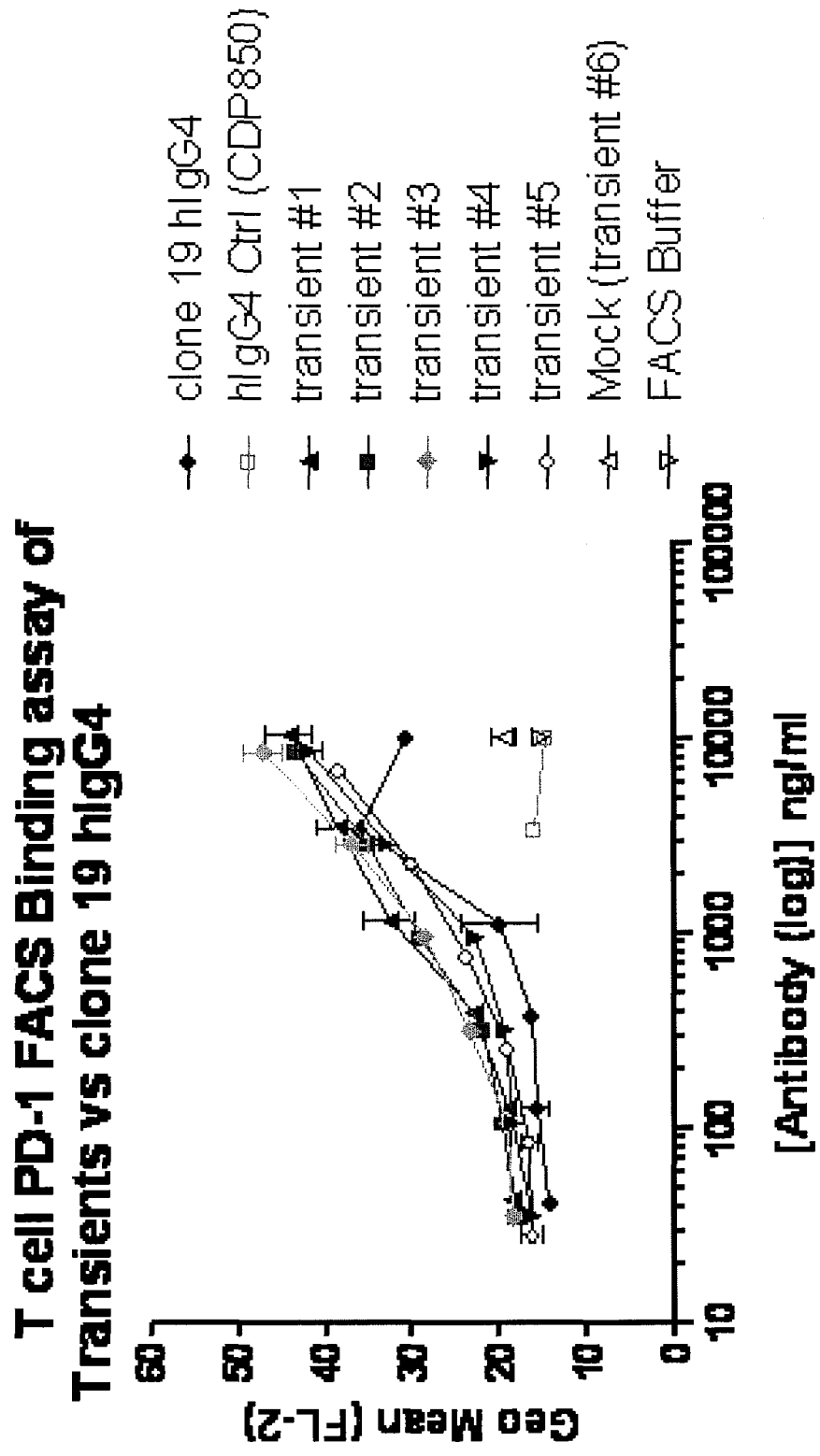
FIGS. 40 and 41 shows activated T-cell binding assay with various constructs
Figure 41:
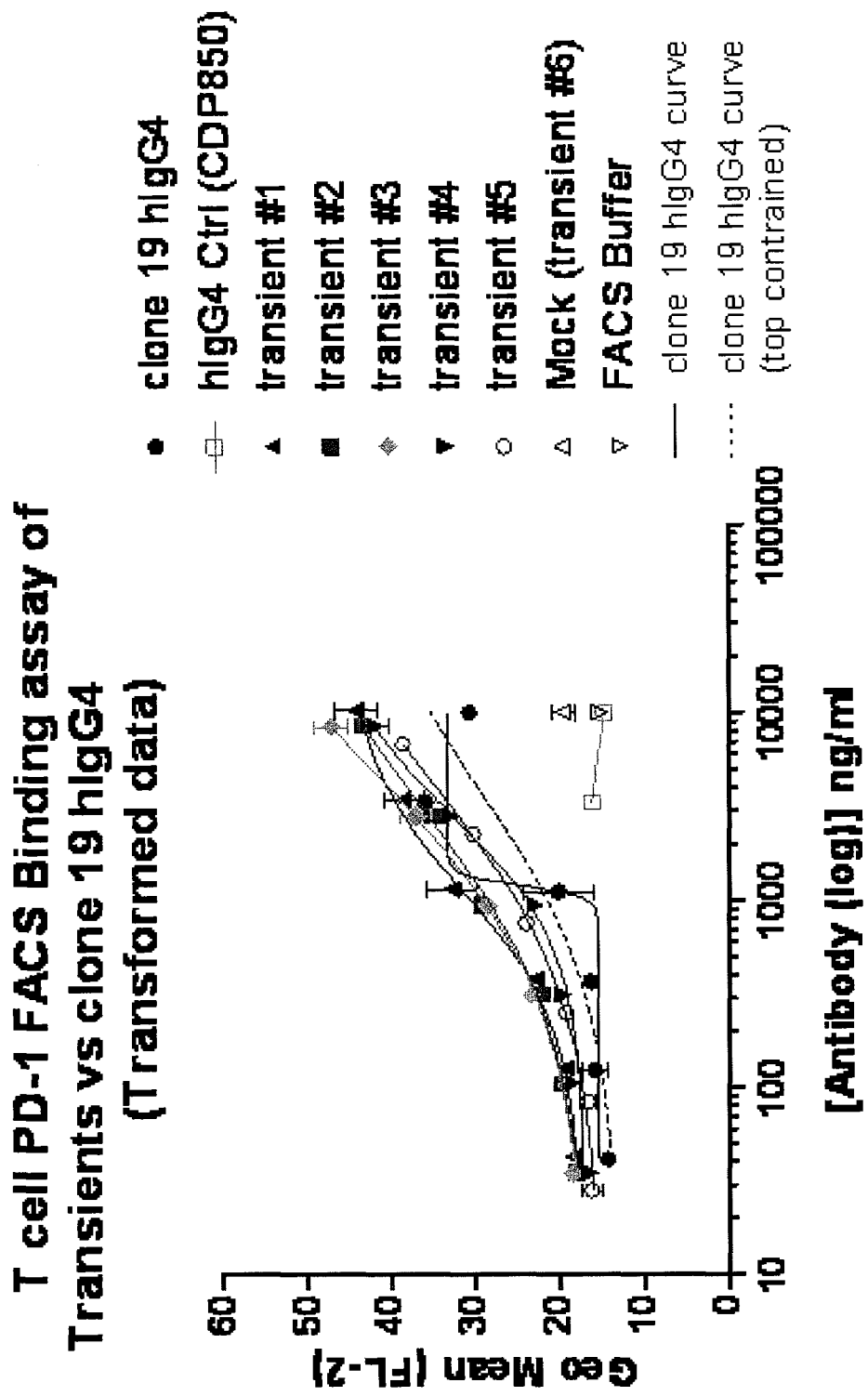

FIGS. 40 and 41 Activated T-cell binding assay with various constructs

FIGS. 42a) and b)—The various antibody constructs cross react with human and cyno PD-1

FIG. 43 shows an alignment of the light chains for the murine, acceptor frameworks and humanised light chains. CDRs are in bold and underlined. Donor residues are in bold, italic and are highlighted.

Example 1

Methods for Generation of Anti-PD-1 Antibody Clone 19

The generation of antibody clone 19 has already been described in international application WO2010/029434.

1.1 Myeloma Cell Line

For fusion the myeloma cell line SP2/0-Ag14 from the German Collection of Microorganisms and Cell Cultures (DSMZ GmbH, Braunschweig) was used. This cell line is a hybrid between BALB/c spleen cells and the myeloma cell line P3x63Ag8. The cells have been described as not synthesizing or secreting immunoglobulin chains, being resistant to 8-azaguanine at 20 µg/ml, and not growing in HAT (Hypoxanthine, Aminopterin, Thymidine) medium. The SP2/0 cells are routinely maintained in tissue culture flasks in standard growth medium (with 10% FCS). A new aliquot of frozen SP2/0 cells was used after a period of 2 weeks in order to avoid the implementation of HGPRT-positive revertants. The myeloma cells were shown to be negative in all mycoplasma tests.

1.2 Antigens for Immunization and Screening

The recombinant protein PD-1Fc was prepared using the methods described for the production of CD28Fc (Evans et al. *Nat Immunol.* 6, 271-9 (2005)) and concentrated to 5.1 mg/ml in 0.01 M HEPES, 150 mM NaCl, pH 7.4. SDS-PAGE analysis of the antigen run under reducing and non-reducing conditions established the purity of the protein to be >95%.

1.3 Immunization

Five mice (about 8 weeks old) were immunized via the intraperitoneal cavity using an immunization protocol over 60 days. For immunization an alum precipitate of the immunogen was prepared. The alum precipitate was freshly prepared for each boost. The mice were immunized with 50 µg protein and boosted with 25 µg protein. Three mice were used for fusion.

1.4 General Handling of Cells

Cells were handled under sterile conditions using a laminar air-flow system, sterile materials and sterile solutions. Cells were incubated at 37° C. in a humid atmosphere containing 5% carbon dioxide. For cultivation of the hybridoma cells a complete growth medium (CGM) containing DMEM with supplements 2-mercaptoethanol, L-Glutamine, GlutaMax, HT, non essential amino acids, sodium pyruvate, antibiotics/antimycotic solution (in concentrations recommended by the supplier) and FCS at different concentrations (10%, 15% or 20%) was used.

1.5 Preparation of Spleen Cells and Cell Fusions

After asphyxiation of the three immunized mice in $CO_2$ spleens were aseptically removed. A single cell suspension of pooled spleens was prepared. The spleen cells and the myeloma cells were washed several times with DMEM and fused twice in the presence of 1 ml 50% (w/v) PEG 3550 (ratio spleen cells to SP2/0 2.5:1 and 2.4:1). The hybridomas produced were resuspended in CGM containing 20% FCS and aminopterin (HAT medium). The cell suspension (140 Cl/well) of each fusion was plated out into eight 96-well tissue culture flat-bottom plates (Corning-Costar) containing 140 Cl/well peritoneal exudate cells as feeder cells in CGM with 20% FCS. The plates were incubated for 10 days. During this period cells were fed two times with HAT medium. An aliquot of the spleen cell preparation (about $8 \times 10^6$ spleen cells) was cultivated 10 days in a well of a 24-well plate and the cell culture supernatant served as positive control in ELISA.

1.6 Screening Assay

An ELISA was used for screening of IgG in cell culture supernatants. 96 well flat-bottom polystyrene microtiter plates (Greiner, Cat. No 655061) were coated with 50 µl/well PD-1Fc antigen (5 µg/ml) in 0.5 M carbonate/bicarbonate buffer, pH 9.6. After incubation overnight in a moist chamber at 4° C. the plates were washed with tris-buffered saline (TBS, 50 mM Tris, pH 7.8, 500 mM sodium chloride) containing 0.01% Triton X-100 (washing buffer) and blocked with 200 µl/well 2% FCS in TBS (blocking buffer) for 1 hour at room temperature (RT) on a shaker. The wells were washed with washing buffer and 100 µl cell culture supernatant was added in the appropriate well. Cell culture supernatant from SP 2/0 myeloma cells was used as a negative control. As positive control cell culture supernatant from spleen cell culture was used. The plates were incubated on a shaker for 1 h at RT, followed by several washes. For detection of bound antibodies plates were incubated with 50 µl/well goat anti-mouse IgG (Fab specific) conjugated to alkaline phosphatase (1:5000) in blocking buffer for 1 h at RT on a shaker, followed by several washes and addition of 150 µl/well substrate buffer (2 mM 4-nitrophenyl phosphate in 5% diethanolamine+0.5 mM $MgCl_2$, pH 9.8). The optical density (OD) was estimated in a 12-channel Dynex Opsys MR microplate reader at 405 nm. Wells with OD405 nm 2-fold higher than the OD405 nm of the average plate value were selected as positive.

1.7 Selection of Stable Antibody Producers

Cells from positive IgG producing cultures were transferred into wells of a 48-well plate and cultivated for several days (depending on the growth characteristics of the cells). An ELISA on PD-1Fc and without precoated antigen in order to select the specific binders was carried out. The cells from ELISA-positive wells were frozen in freezing medium (90% FCS, 10% DMSO). An aliquot of the cells was further cultivated for production of cell culture supernatants for further characterization.

1.8 Limiting Dilution Cloning

As soon as positive wells were identified, hybridoma cells were cloned to reduce the risk of overgrowth by non-producing cells (first cloning). To ensure that the antibodies are truly monoclonal the hybridomas were cloned again (second cloning). The method of limiting dilution was used for both cloning procedures. IgG producing cells were distributed into one 96 well plate containing feeder cells at a density of 1-3 cells per well. After 8-10 days (depending on growth characteristics) all plates were visually inspected under the microscope for detection of monoclonal growth. Culture supernatants from such wells were screened for specific immunoglobulin content using the above-described screening assay. The appropriate clones concerning growth characteristic and ELISA signal were selected, transferred into wells of a 24-well plate and cultivated for some days. A screening assay was performed. This procedure was repeated two to three times. The appropriate subclone was selected respectively for the second cloning procedure or cultivation for cryopreservation. This procedure resulted in the production of an anti-PD-1 antibody known as Clone 19.

1.9 Preparation and Isotyping of Antibodies

Hybridoma supernatant was prepared and diluted into sterile, azide-free PBS. Purified stocks of monoclonal antibodies were isotyped at 1 µg/ml in PBS using the IsoStrip Mouse Monoclonal Antibody Isotyping Kit (Santa Cruz; sc-24958). Clone 19 was found to be isotype $IgG_{1\kappa}$.

1.10 Sequencing of Clone 19

The genes encoding clone 19 were cloned and sequenced and are provided in FIG. 1. This antibody was named antibody CA051__00949 (often abbreviated to 949).

Example 2

Characterisation and Selection of Antibody 949

2.1 Rationale for Antibody Selection

In order to generate a therapeutic reagent which is able to transduce an inhibitory signal to T cells through PD-1, an agonistic anti-PD-1 monoclonal antibody was selected. Targeting the membrane proximal epitope with this antibody will ensure that it does not block the binding of the endogenous ligands for PD-1 (PD-L1 or PD-L2). Therefore, the agonistic antibody will act in addition to, and may potentiate, any natural inhibitory signals from the ligands being transduced through PD-1. Humanised versions of this antibody will have potential therapeutic utility in a wide range of human diseases which involve inappropriate levels of T or B lymphocyte activation.

2.2 Analysis of PD-1 Agonism Induced by Antibody 949 on Human $CD4^+$ T Cells To demonstrate that antibody 949 (parental variable regions, murine IgG1) can induce signaling through PD-1, it was tested for its ability to inhibit T cell receptor (TCR)-derived activating signals. This was achieved by covalently coupling 949, along with a TCR-activating anti-CD3 antibody, to Dynalbeads. The beads were then added to cultures of primary human $CD4^+$ T cells and the resultant proliferation measured by $^3H$-thymidine incorporation after 6 days.

Tosyl-activated 4.5 µm Dynalbeads (M450; Invitrogen) were washed in 0.1M sterile phosphate buffer (pH 7.5) and loaded with 2 µg of anti-human CD3 (clone OKT3) per 1×10⁷ beads at 37° C. for 8 h with continuous inversion mixing. The beads were then washed to remove unconjugated anti-CD3 and aliquots were secondarily coated with 3 µg of BSA, a non-agonistic control anti-PD-1 antibody, 949 or recombinant human PD-L2.mFc per 1×10⁷ beads at 37° C. for 19 h with continuous inversion mixing. Beads were subsequently washed and incubated in 0.2M Tris/0.1% BSA (pH 8.5) for 3 hours to inactivate free tosyl groups, followed by washing and re-suspension of beads in PBS/0.1% BSA/2 mM EDTA (pH 7.4). Equal anti-CD3 and antibody/ligand coating of the bead sets was confirmed by staining the beads with fluorochrome-labelled isotype-specific antibodies and analysing by flow cytometry.

For human T cell proliferation studies, fresh heparinised blood was diluted 1:1 with RPMI and the lymphocytes isolated by density gradient separation (Ficoll Hypaque). CD4⁺ T cells were purified from the whole PBMCs by negative selection using MACS (CD4⁺ T cell isolation Kit II; Miltenyi Biotec). 1×10⁵ human CD4⁺ T cells/well were cultured at a 1:1 ratio with the coated beads in 96-well round-bottomed plates and incubated at 37° C./5% CO₂/100% humidity for 6 days. Proliferation was measured after 6 days by addition of 0.5 µCi/well ³H-thymidine for the last 6 hours of culture. Cells were harvested onto glass-fibre filters and incorporated ³H-thymidine was measured by β-scintillation counting.

2.3 Results

The results in FIG. 13 show the day 6 proliferative response by human CD4⁺ T cells measured in the presence of anti-CD3 plus anti-PD-1 antibody or BSA control coated beads. The data are expressed as percentage of the maximal response (anti-CD3 plus BSA control) and are the mean of 4 different donor responses. CD4⁺ T cell proliferation was inhibited by antibody 949, so that the average proliferation observed was only 51.6% of the maximum. Similar inhibition of CD4⁺ T cell proliferation was seen with recombinant human PD-L2, utilised as a positive control for PD-1 signaling. In comparison, a non-agonistic anti-PD-1 mAb was used, which showed no effect on CD4⁺ T cell proliferation in this assay as expected. This demonstrates that antibody 949 is capable of inducing agonistic signaling through PD-1, which leads to inhibition of human CD4⁺ T cell responses.

Example 3

Humanisation of Antibody CA051_00949

Antibody CA051_00949 was humanised by grafting the complementarity determining regions (CDRs, FIG. 1c) from the mouse antibody V-regions onto human germline antibody V-region frameworks. In order to recover the activity of the antibody, a number of framework residues from the mouse V-regions were also retained in the humanised sequence. These residues were selected using the protocol outlined by Adair et al. (1991) (Humanised antibodies. WO91/09967). Alignments of the mouse antibody (donor) V-region sequences with the human germline antibody (acceptor) V-region sequences are shown in FIGS. 17 and 18 together with the designed humanised sequences.

The CDRs grafted from the donor to the acceptor sequence are as defined by Kabat (Kabat et al. Sequence of proteins of immunological interest (1987). Bethesda, Md., National Institutes of Health, US), with the exception of CDR-H1 where the combined Chothia/Kabat definition is used (see Adair et al. (1991) Humanised antibodies. WO91/09967).

The heavy chain CDRs of antibody 949 were grafted onto the human V-region VH1 1-3 1-46 plus JH4 J-region (V BASE, http://vbase.mrc-cpe.cam.ac.uk/). The heavy chain framework residues are all from the human germline gene, with the exception of residues 25, 37, 41, 48, 71, 73 and 76 (Kabat numbering), where the donor residues Phenylalanine (F25), Methionine (M37), Histidine (H41), Isoleucine (I48), Valine (V71), Lysine (K73) and Threonine (T76) were retained, respectively. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. The resulting humanised sequence was named 949 gH1a. An alternative humanised heavy chain sequence, 949 gH1b, was created by grafting the CDRs onto human V-region VH1 1-2 1-e plus JH4 J-region (V BASE, http://vbase.mrc-cpe.cam.ac.uk/). The heavy chain framework residues are all from the human germline gene, with the exception of residues 25, 37, 41, 48, 71, 76 and 78 (Kabat numbering), where the donor residues Phenylalanine (F25), Methionine (M37), Histidine (H41), Isoleucine (I48), Valine (V71), Threonine (T76) and Valine (V78) were retained, respectively. The Glutamine residue at position 1 of the human framework was replaced with Glutamic acid (E1) to afford the expression and purification of a homogeneous product.

Human V-region VK1 2-1-(1) L23 plus JK4 J-region (V BASE, http://vbase.mrc-cpe.cam.ac.uk/) was chosen as the acceptor for the light chain CDRs. The light chain framework residues are all from the human germline gene, with the exception of residues 1, 2, 3, 4, 47, 60 and 70 (Kabat numbering), where the donor residues Glutamaic acid (E1), Asparagine (N2), Valine (V3), Leucine (L4), Tryptophan (W47), Aspartic acid (D60) and Serine (S70) were retained, respectively. The resulting humanised sequence was named 949 VK1 gL1. An alternative humanised light chain sequence, 949 VK3 gL1, was created by grafting the CDRs onto human V-region VK3 6-1-(1) A27 plus JK4 J-region (V BASE, http://vbase.mrc-cpe.cam.ac.uk/). The light chain framework residues are all from the human germline gene, with the exception of residues 2, 47, 58, 70, 71 and 85 (Kabat numbering), where the donor residues Asparagine (N2), Tryptophan (W47), Valine (V58), Serine (S70), Tyrosine (Y71) and Threonine (T85) were retained, respectively.

Genes encoding the humanised 949 VK1 gL1, 949 VK3 gL1, 949 gH1a and 949 gH1b light and heavy chain V-region sequences were designed and constructed by an automated synthesis approach by Entelechon GmbH. Oligonucleotide-directed mutagenesis was used to modify the genes to create variants of the humanized heavy chains (gH2a through to gH20a, and gH2b through to gH20b) and light chains (VK1 gL2 through to gL17, and VK3 gL2 through to gL17), and in some cases a deamidation site in CDRL3 was modified (FIG. 2a). FIG. 27a shows a light chain gL15 comprising a modified CDRL3. The humanised 949 light chain V-region gene sequences were cloned into the UCB-Celltech human light chain expression vector pKH10.1, which contains DNA encoding the human Kappa chain constant region (Km3 allotype). The humanised 949 heavy chain V-region gene sequences were cloned into the UCB-Celltech human gamma-4 heavy chain expression vector pVhγ4P FL, which contains DNA encoding the human gamma-4 heavy chain constant region with the hinge stabilising mutation S241P (Angal et al., Mol Immunol. 1993, 30(1):105-8), and also into a version of the human gamma-4P heavy chain vector in which the codon for the C-terminal Lysine residue has been removed, pVhγ4P delta Lys. The humanised 949 heavy chain V-region gene sequences were also cloned into the UCB- Celltech human gamma-1 heavy chain expression vector pVhγ1 delta Lys, which contains DNA encoding the human gamma-1 heavy chain constant region with the C-terminal Lysine residue removed. Transient co-transfection of light and heavy chain vectors into HEK293 suspension cells was achieved using 293 Fectin (12347-019 Invitrogen), and gave expression of the humanised, recombinant 949 antibodies.

A number of different variants of the humanised heavy and light chains were generated by including the CDRs in FIG. 1(c) derived from antibody 949 and 2(a) CDRL3 from clone 19 with a modified deamidation site, and one or more of the donor residues listed below, depending on the framework used. The sequences are provided in FIGS. 2-11 and FIGS. 17 to 38.

| 3.1 Ab949 residues for humanization VK1 Light chain 2-1-(1) L23 | |
|---|---|
| Kabat position | Human acceptor residue |
| 1 | Alanine |
| 2 | Isoleucine |
| 3 | Arginine |
| 4 | Methionine |
| 47 | Phenylalanine |
| 60 | Serine |
| 70 | Aspartic acid |

| VK3 Light chain 6-1-(1) A27 | |
|---|---|
| Kabat position | Human acceptor residue |
| 2 | Isoleucine |
| 47 | Leucine |
| 58 | Isoleucine |
| 70 | Aspartic acid |
| 71 | Phenylalanine |
| 85 | Valine |

| VH Heavy chain 1-3 1-46 | |
|---|---|
| Kabat position | Human acceptor residue |
| 25 | Serine |
| 37 | Valine |
| 41 | Proline |
| 48 | Methionine |
| 71 | Arginine |
| 73 | Threonine |
| 76 | Serine |

| VH Heavy chain 1-2 1-e | |
|---|---|
| Kabat position | Human acceptor residue |
| 25 | Serine |
| 37 | Valine |
| 41 | Proline |
| 48 | Methionine |
| 71 | Alanine |
| 76 | Serine |
| 78 | Alanine |

Example 4

Characterisation of the Humanised Antibodies Generated in Example 3

4.1 Affinity
Binding Affinity Measurements

The assay format involved capture of 949 or humanised version thereof by immobilised anti-human Fc and subsequent titration of the human PD-1 over the captured surface.

BIA (Biamolecular Interaction Analysis) was performed using a BIAcore 3000 (BIAcore AB). Affinipure F(ab')$_2$ Fragment, goat anti-human IgG, Fc fragment specific (Jackson ImmunoResearch) was immobilised on a CM5 Sensor Chip via amine coupling chemistry to a capture level of ≈6000 response units (RUs). A blank surface was prepared in a similar way, omitting the Fc fragment from the procedure. HBS-EP buffer (10 mM HEPES pH 7.4, 0.15 M NaCl, 3 mM EDTA, 0.005% Surfactant P20, BIAcore AB) was used as the running buffer with a flow rate of 10 μl/min. A 10 μl injection of 949 IgG at ~1 μg/mL was used to give ~200RU capture by the immobilised anti-human IgG-Fc. Human PD-1 was titrated over the captured 949 or humanised variants at various concentrations (50 nM or below) at a flow rate of 30 μL/min. The surface was regenerated by a 10 μL injection of 40 mM HCl, followed by a 5 μL injection of 5 mM NaOH at a flowrate of 10 μL/min.

Background subtraction binding curves were analysed using the BIAevaluation software (version 3.2) following standard procedures. Kinetic parameters were determined from the fitting algorithm.

Data for 949 and the various humanised versions are shown in Table 1. For all grafts tested except for 1, (VK1 gL11gH1a) affinity for PD-1 was improved compared to the 949 parental antibody. The chimeric contained the 949 variable regions with human IgG4 constant domains.

TABLE 1

| 4.2 Analysis of ligand blocking activity of antibody 949 and humanised versions of 949 | | | |
|---|---|---|---|
| Antibody | ka (1/Ms) | kd (1/s) | KD (nM) |
| 949 parental | 2.66E+05 | 1.35E−03 | 5.07 |
| 949 chimeric | 1.95E+05 | 1.17E−03 | 5.98 |
| 949 VK1gL1 gH1a | 2.11E+05 | 7.82E−04 | 3.71 |
| 949 VK1 gL1 gH1b | 1.91E+05 | 5.56E−04 | 2.92 |
| 949 VK1 gL11 gH1a | 2.07E+05 | 1.15E−03 | 5.54 |
| 949 VK1 gL9 gH8a | 2.45E+05 | 5.74E−04 | 2.35 |
| 949 VK1 gL9 gH20a | 2.30E+05 | 7.27E−04 | 3.17 |
| 949 VK1 gL9 gH8b | 2.27E+05 | 5.32E−04 | 2.34 |
| 949 VK1 gL9 gH20b | 2.47E+05 | 6.58E−04 | 2.66 |
| 949 VK1 gL12 gH8a | 2.34E+05 | 5.74E−04 | 2.46 |
| 949 VK1 gL12 gH20a | 2.26E+05 | 7.66E−04 | 3.38 |
| 949 VK1 gL12 gH8b | 2.22E+05 | 6.14E−04 | 2.77 |
| 949 VK1 gL12 gH20b | 2.20E+05 | 8.35E−04 | 3.80 |
| 949 VK1 gL14 gH8a | 2.09E+05 | 9.92E−04 | 4.75 |
| 949 VK1 gL14 gH8b | 2.03E+05 | 8.88E−04 | 4.38 |
| 949 VK3 gL1 gH1a | 2.10E+05 | 8.44E−04 | 4.02 |
| 949 VK3 gL1 gH1b | 2.07E+05 | 6.50E−04 | 3.14 |
| 949 VK3 gL11 gH1a | 2.23E+05 | 1.09E−03 | 4.89 |
| 949 VK1 gL15 Gh2 | 2.37E+05 | 8.56E−04 | 3.61 |

PD-1 ligand binding assays were performed to determine if antibody 949 (chimeric human IgG4 (parental V region), and humanised transient clones of 949) had the capacity to block ligand binding. In these assays PD-1 expressing HEK cells were incubated with purified or transiently expressed antibody supernatants for 30 minutes, followed by incubation with recombinant human PD-L2.mFc fusion protein. Binding of the PD-L2.mFc to cell expressed PD-1 was then revealed with a PE-conjugated anti-mouse IgG H+L antibody.

Method

HEK293 cells were transiently transfected by culturing at 5×10$^6$/well with 5 μg human PD-1 DNA and 293 fectin (Invitrogen) overnight in 6 well plates. The following day PD-1 expressing HEK293 cells were added to 96 well U-plate at 1×10$^5$/well in 50 μL and pre-incubated for 30 mins on ice with 50 μL of either human IgG4 control (10 μg/mL), or purified chimeric 949 (10, 3.3 or 1.1 μg/mL), or control anti-PD-1 antibody (10, 3.3 or 1.1 μg/mL), or 150 μL neat humanised 949 transient supernatants. Recombinant human PD-L2.mFc fusion protein was added to the cells at 0.3 μg/mL final concentration for a further 30 minutes on ice. HEK cells were washed twice in FACS buffer. Phycoerythrin conjugated anti-mouse H+L IgG was diluted 1/200 and added to the cell pellets at 50 μL per well. Cells were incubated on ice for 30 minutes. Cells were washed twice in FACS buffer and immediately acquired on the flow cytometer.

Results

The data in FIG. 14 shows PD-L2.mFc binding to PD-1 transfected HEK cells when pre-blocked with either control IgG4 or anti-PD-1 antibodies. Control IgG4 did not inhibit binding of PD-L2 to the cells as indicated by an increase in geometric mean fluorescent intensity. Purified, chimeric 949 antibody did not inhibit PD-L2 binding to PD-1 expressing cells at concentrations between 1 and 10 μg/mL. A control anti-PD-1 antibody with known ligand blocking properties did block PD-L2 binding to PD-1 expressing cells at the concentrations tested, confirming that ligand blocking could be detected in this assay format. All humanised versions of antibody 949 also did not inhibit PD-L2 binding to PD-1 expressed on cells.

4.3 Analysis of Functional Activity of Antibody 949 and Humanised Versions thereof A reporter gene assay was developed using a Jurkat cell line which stably expresses a chimeric receptor comprising the extracellular ligand binding and transmembrane domains of human PD-1 and human CD28 signaling and human TCRζ intracellular domains. These cells have a reporter gene under the control of an NFκB-dependent promoter and the cells produce secreted alkaline phosphatase (SEAP) when stimulated with recombinant human PD-Ligand 1 or 2, demonstrating that this reporter assay is capable of detecting PD-1 agonism. The assay was used to compare the functional agonistic activity of the parental murine antibody 949 with a range of humanised constructs.

The human PD-1/CD28/TCRζ chimera construct was generated according to the methods described in International Application WO 2007/060406. Jurkat cells were stably transfected with the human PD-1/CD28/TCRζ chimera in the SEAP reporter vector. Cells were prepared in bulk and stored in liquid nitrogen until used. Cells were thawed and dispensed in 15 μL aliquots of medium containing 30,000 cells per 384 well. The antibody/construct was prepared at 4× final concentration in NM6 medium, and a 5 μL volume added to duplicate wells. After 18 hours incubation, 4 μL of supernatant was assayed for SEAP activity as described in the pack leaflet (Clontech, Great Escape™ SEAP). Activity was calculated as fold induction (signal divided by background signal).

The data in FIG. 15 shows antibody 949 stimulated release of SEAP from the Jurkat human PD-1/CD28/TCRζ SEAP reporter cell line. The control human antibody, CAN-1, did not stimulate release of SEAP. The original CA949 construct, cLcH, and the construct VK1 gL12 gH8b produced similar titrations in the assay. Table 2 indicates that all the humanised constructs tested generated a SEAP response in this assay, demonstrating that they have maintained their agonistic function after humanisation.

TABLE 2

Comparison of humanised versions of 949 in the human PD-1/CD28/TCRζ SEAP reporter assay. EC50 values were calculated as the concentration of antibody required to generate 50% of the maximal signal generated by that antibody

| | EC50 (ug/mL) |
|---|---|
| VK1 gL9 gH8a | 0.22 |
| VK1 gL9 gH8b | 0.23 |
| VK1 gL9 gH20a | 0.25 |
| VK1 gL9 gH20b | 0.27 |
| VK1 gL12 gH8a | 0.29 |
| VK1 gL12 gH8b | 0.20 |
| VK1 gL12 gH20a | 0.18 |
| VK1 gL12 gH20b | 0.18 |
| VK1 gL14 gH8a | 0.15 |
| VK1 gL14 gH8b | 0.11 |
| 949 cLcH | 0.08 |

4.4 Flow Cytometry Analysis of 949 Chimeric and 949 Humanised Grafts Binding to HEK293 Human, Cynomolgus and Rhesus PD-1

To confirm that the humanised grafts of antibody 949 maintained cross-reactivity with non-human primate PD-1, flow cytometry assays were carried out with HEK293 suspension cells which had been transiently transfected with DNA encoding full length human, cynomolgus or rhesus PD-1. HEK293 cells were transiently transfected by culturing at 5×10$^6$/well with 5 μg DNA and 293 fectin (Invitrogen) overnight in 6 well plates. The following day human, cynomolgus or rhesus PD-1 expressing HEK293 cells were resuspended in 0.2% BSA (w/v) PBS+0.09% sodium azide and incubated for 1 hr at 4° C. with stated concentrations of 949 chimeric, 949 humanised grafts, 949 chimeric (purified) or control antibodies. Cells were washed with PBS and incubated with secondary antibody—1:1000 FITC (Fab)2 Goat anti Human Fc specific (109-006-098 Jackson) for 1 hr at 4° C. Analyses were performed on a FACSCalibur (Becton Dickinson).

Figure 16B:
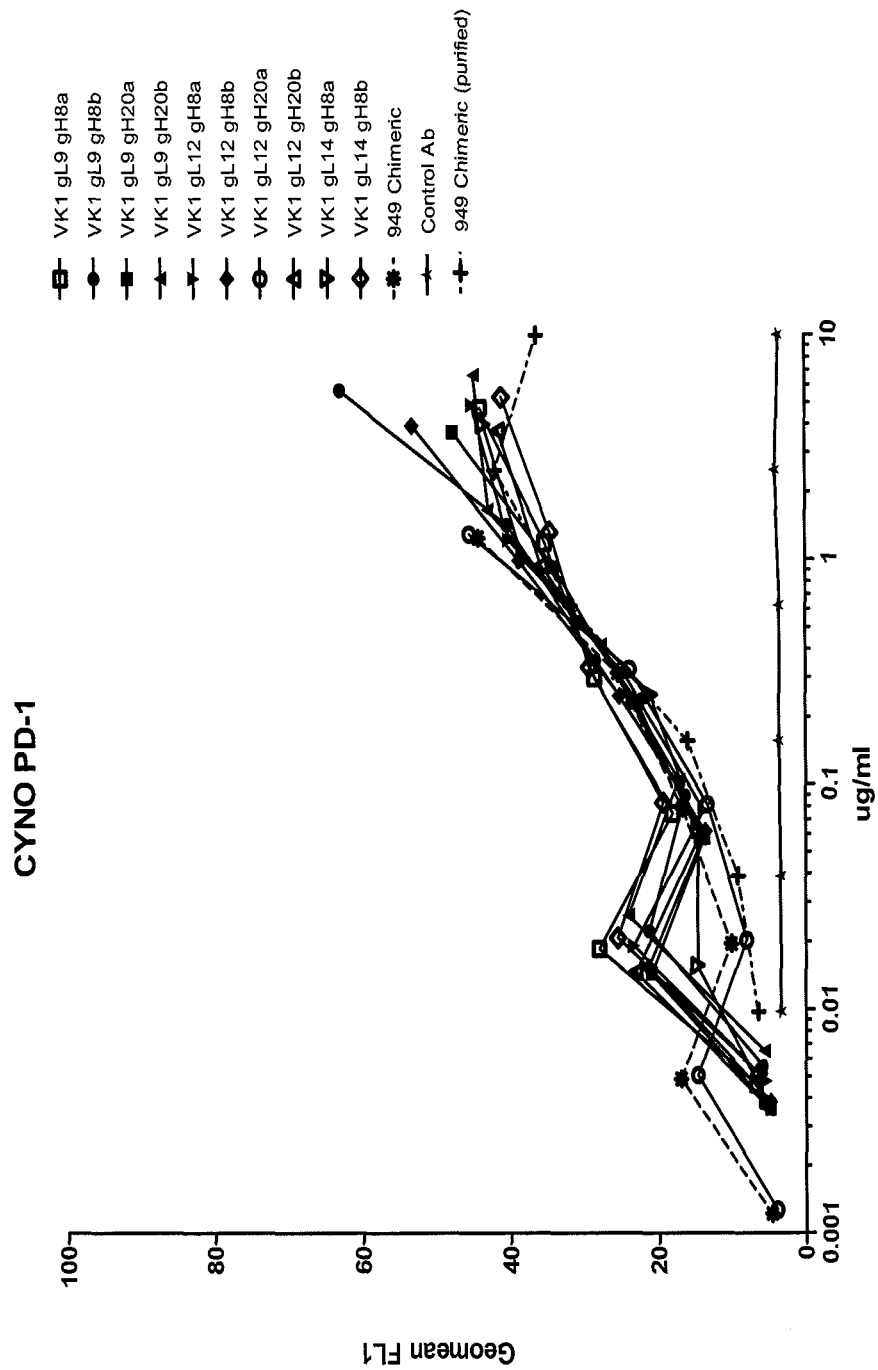
Figure 16:
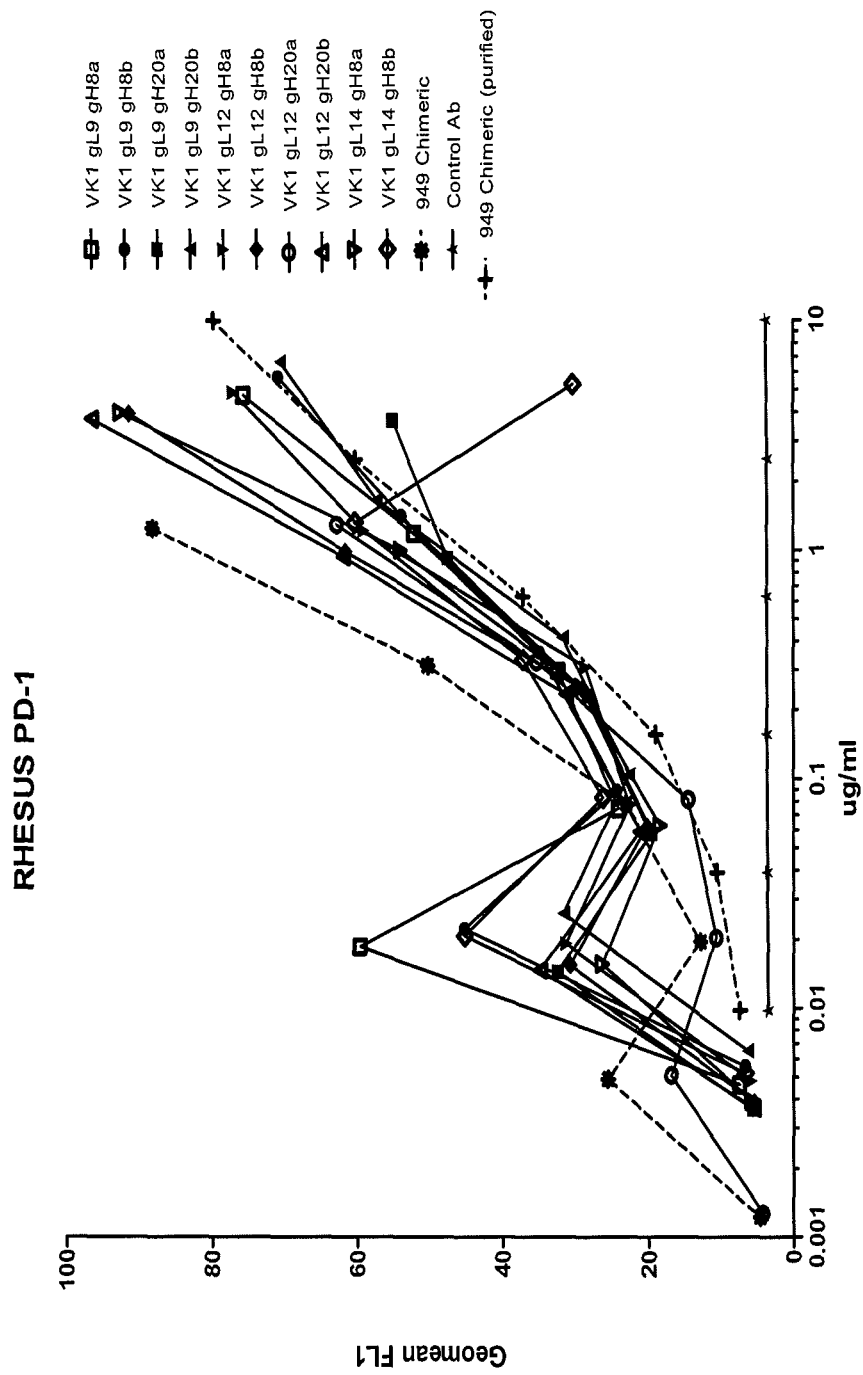
Figure 16:
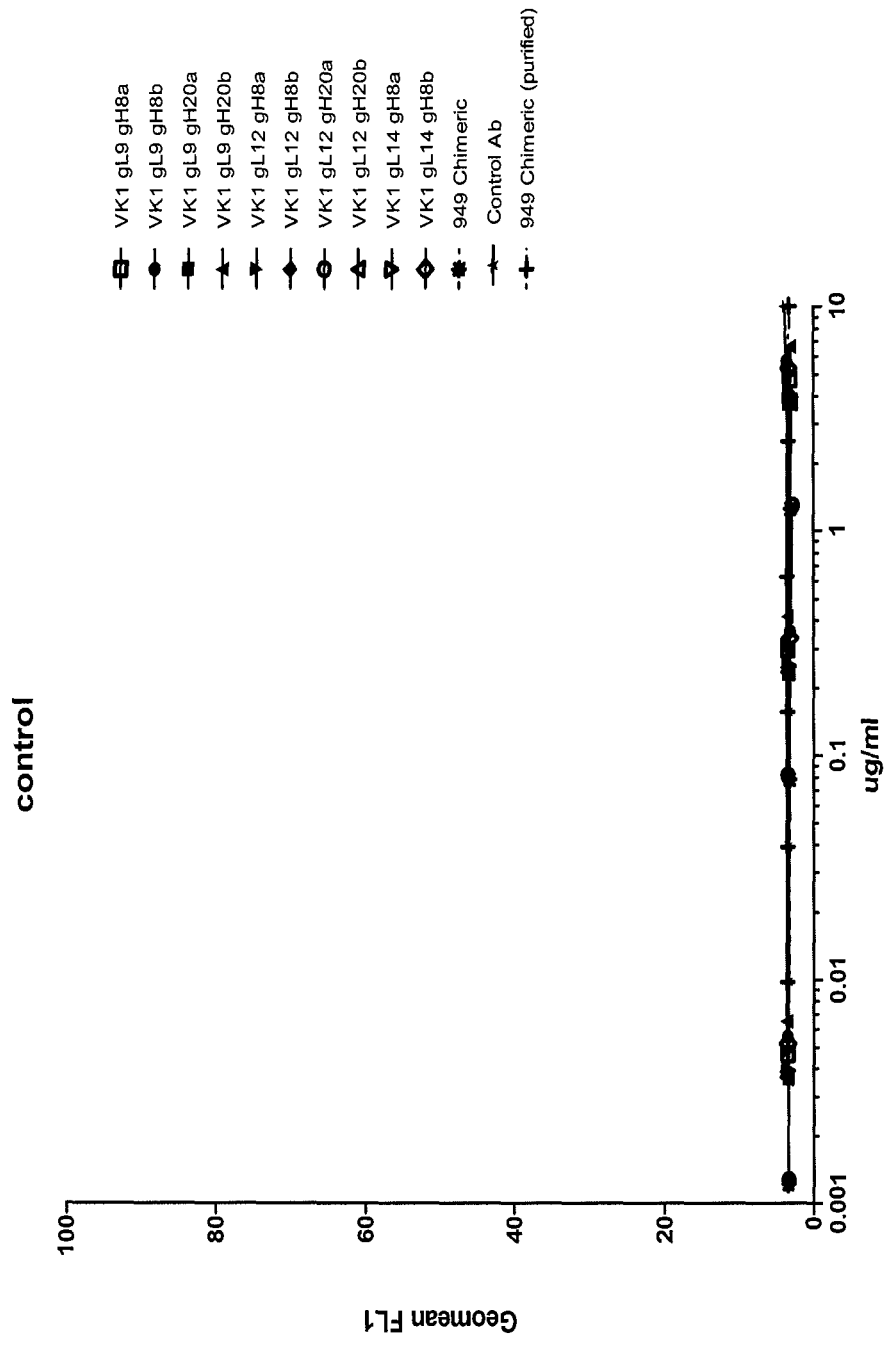

The results are shown in FIG. 16. They indicate that i) all the grafts bind specifically to PD-1 expressing cells (FIG. 16a, d), ii) they all retain human PD-1 binding equivalent to the original sequence (FIG. 16a) and iii) they all cross-react with PD-1 from cynomolgus (FIG. 16b) and rhesus (FIG. 16c) monkeys.

4.5 Ligand Blocking Assay

PD-1 transfect HEK293 cells with test antibody for 30 minutes on ice. Then a control CAN1.Fc or PD-L2mFc were added at 0.3 μg/mL for a further 30 minutes on ice after which cells were washed and the ligand binding revealed with anti mouse IgG H+L PE. The results are shown in FIG. 39. In summary the results show that the various 949 constructs do not prevent ligand binding.

4.6 Activated T-Cell Binding Assay

Human T cells isolated from whole blood via MACS (pan T cell kit) and activated with PHA-L (1 μg/ml) & IL-2 (1 ng/ml) for 3 days Cells washed in FACS buffer and added to a 96-well plate at ~1×10$^5$ cell/well Cells were incubated with samples for ½ hour on ice, and then washed twice in FACS buffer.

Antibody samples (in duplicate) diluted ⅓ from 10 μg/ml or neat (6-point titration curve)

Samples include Clone 19 hIgG4, CDP850 (hIgG4 control) and transient samples:

Transient #1=949 VK1 gL9 gH 20b (10.3 μg/ml)
Transient #2=949 VK1 gL15 gH 8a (8.5 μg/ml)
Transient #3=949 VK1 gL15 gH 8b (8.4 μg/ml)
Transient #4=949 VK1 gL15 gH 20a (8.53 μg/ml)
Transient #5=949 VK1 gL15 gH 20b (6.8 μg/ml)
Transient #6=mock (tested neat)

Cells were then incubated with reveal antibody (anti-human IgG H+L, PE conjugated, diluted to 1/200 in FACS buffer) for ½ hour on ice.

Cells were washed twice in FACS buffer and read on FACSCalibur 2 (acquired ~10 000 lymphocytes per sample). The results are shown in FIG. 40.

The EC50's were all between 1-6 µg/ml
EC50's (ng/ml):
Clone 19 hIgG4: ~1197 (unconstrained curve) or 3611 (top part curve constrained to ~45 geo mean)
Transient #1: 1142
Transient #2: 3147
Transient #3: 6092
Transient #4: 2889
Transient #5: 4096

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

What is claimed is:

1. A humanised agonistic antibody which binds human PD-1 comprising a heavy chain and a light chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the variable domain of the light chain comprises the sequence given in SEQ ID NO:4 for CDR-L1, the sequence given in SEQ ID NO:5 for CDR-L2 and the sequence given in SEQ ID NO:7 for CDR-L3.

2. A humanised agonistic antibody according to claim 1, which binds human PD-1 comprising a heavy chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the heavy chain framework region is derived from human sub-group sequence VH 1-3 1-46+JH4 (SEQ ID NO: 52).

3. A humanised antibody according to claim 2 wherein the residue at at least one of positions 25, 37, 41, 48, 71, 73 and 76 of the variable domain of the heavy chain is a donor residue.

4. A humanised antibody according to claim 3 having the heavy chain variable domain sequence given in SEQ ID NO:30, SEQ ID NO:38 or SEQ ID NO:40.

5. A humanised agonistic antibody according to claim 1, which binds human PD-1 comprising a heavy chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the heavy chain framework region is derived from human sub-group sequence VH 1-2 1-e+JH4 (SEQ ID NO: 54).

6. A humanised antibody according to claim 5 having the heavy chain variable domain sequence given in SEQ ID NO:46.

7. A humanised antibody according to claim 5 wherein the residue at, at least one of, positions 25, 37, 41, 48, 71, 76 and 78 of the variable domain of the heavy chain is a donor residue.

8. A humanised antibody according to claim 7 having the heavy chain variable domain sequence given in SEQ ID NO:42 or SEQ ID NO:44.

9. A humanised agonistic antibody according to claim 1, which binds human PD-1 comprising a light chain wherein the variable domain of the light chain comprises the sequence given in SEQ ID NO:4 for CDR-L1, the sequence given in SEQ ID NO:5 for CDR-L2 and the sequence given in SEQ ID NO:7 for CDR-L3 and the light chain framework region is derived from human sub-group sequence VK1 2-1(1) L23+JK4 (SEQ ID NO:48).

10. A humanised antibody according to claim 9 wherein the residue at, at least one of positions 1, 2, 3, 4, 47, 60 and 70 of the variable domain of the light chain is a donor residue.

11. A humanised antibody according to claim 10 having the light chain variable domain sequence given in SEQ ID NO:20, SEQ ID NO:24 or SEQ ID NO:66.

12. A humanised agonistic antibody according to claim 1, which binds human PD-1 comprising a light chain wherein the variable domain of the light chain comprises the sequence given in SEQ ID NO:4 for CDR-L1, the sequence given in SEQ ID NO:5 for CDR-L2 and the sequence given in SEQ ID NO:7 for CDR-L3 and the light chain framework region is derived from human sub-group sequence VK3 6-1-(1) A27+JK4 (SEQ ID NO:50).

13. A humanised antibody according to claim 12 wherein the residue at least one of positions 2, 47, 58, 70, 71 and 85 of the variable domain of the light chain is a donor residue.

14. A humanised antibody according to claim 13 having the light chain variable domain sequence given in SEQ ID NO:28.

15. A humanised agonistic antibody according to claim 1 having a heavy chain comprising a sequence selected from the group consisting of: SEQ ID NO:30, SEQ ID NO:38, SEQ ID NO:40, SEQ ID NO:42, SEQ ID NO:44 and SEQ ID NO:46 and a light chain comprising a sequence selected from the group consisting of SEQ ID NO:20, SEQ ID NO:24, SEQ ID NO:28 and SEQ ID NO:66.

16. A humanised agonistic antibody according to claim 1 having a heavy chain comprising a sequence selected from the group consisting of: SEQ ID NO:46, SEQ ID NO:58, SEQ ID NO:62, SEQ ID NO:76 and SEQ ID NO:80 and a light chain comprising a sequence selected from the group consisting of SEQ ID NO:20, SEQ ID NO:24, SEQ ID NO:28, SEQ ID NO:66 and SEQ ID NO:70.

17. An agonistic antibody molecule according to claim 1, wherein the antibody molecule is selected from the group consisting of: a complete antibody molecule having full length heavy and light chains or a fragment thereof, such as a Fab, modified Fab', Fab', F(ab')$_2$, Fv, VH, VL or scFv fragment.

18. A humanised agonistic antibody according to claim 1, wherein the variable domain of the light chain comprises a sequence having at least 80% identity or similarity to the light chain variable domain of a light chain comprising a sequence selected from the group consisting of SEQ ID NO:20, SEQ ID NO:24, SEQ ID NO:28 and SEQ ID NO:66; and wherein the variable domain of the heavy chain comprises a sequence having at least 80% identity or similarity to the heavy chain variable domain of a heavy chain comprising a sequence selected from the group consisting of: SEQ ID NO:30, SEQ ID NO:38, SEQ ID NO:40, SEQ ID NO:42, SEQ ID NO:44 and SEQ ID NO:46.

19. A humanised agonistic antibody according to claim 1, wherein the variable domain of the light chain comprises a sequence having at least 80% identity or similarity to the light chain variable domain of a light chain comprising a sequence selected from the group consisting of SEQ ID NO: 20, SEQ ID NO:24, SEQ ID NO:28, SEQ ID NO:66 and SEQ ID NO:70; and wherein the variable domain of the heavy chain comprises a sequence having at least 80% identity or similarity to the heavy chain variable domain of a heavy chain comprising a sequence selected from the group consisting of: SEQ ID NO:46, SEQ ID NO:58, SEQ ID NO:62, SEQ ID NO:76 and SEQ ID NO:80.

20. A humanised agonistic antibody according to claim 1 having a binding affinity for isolated human PD-1 (for example human extracellular domain) of less than 5 nM.

21. A pharmaceutical composition comprising an antibody according to claim 1, in combination with one or more of a pharmaceutically acceptable excipient, diluent or carrier.

22. A pharmaceutical composition according to claim 21, additionally comprising other active ingredients.

23. A humanised agonistic antibody according to claim 1, wherein the heavy chain framework region is derived from human sub-group sequence VH 1-2 1-e+JH4 (SEQ ID NO: 54), and the residue at, at least one of, positions 25, 37, 41, 48, 71, 76 and 78 of the variable domain of the heavy chain is a donor residue; or derived from human sub-group sequence VH 1-3 1-46+JH4 (SEQ ID NO: 52), wherein a residue at at least one of positions 25, 37, 41, 48, 71, 73 and 76 of the variable domain of the heavy chain is a donor residue; and the light chain framework region is derived from human sub-group sequence VK1 2-1(1) L23+JK4 (SEQ ID NO:48), and the residue at, at least one of, positions 2, 47, 58, 70, 71 and 85 of the variable domain of the light chain is a donor residue; or derived from human sub-group sequence VK1 2-1(1) L23+ JK4 (SEQ ID NO: 50), and the residue at, at least one of, positions 2, 47, 58, 70, 71 and 85 of the variable domain of the light chain is a donor residue.

* * * * *

SEQUENCE LISTING

```
<160> NUMBER OF SEQ ID NOS: 83

<210> SEQ ID NO 1
<211> LENGTH: 10
<212> TYPE: PRT
<213> ORGANISM: Artificial Sequence
<220> FEATURE:
<223> OTHER INFORMATION: recombinant

<400> SEQUENCE: 1

Gly Tyr Thr Phe Thr Thr Tyr Pro Ile Glu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: recombinant

<400> SEQUENCE: 2

Asn Phe His Pro Tyr Asn Asp Asp Thr Lys Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: recombinant

<400> SEQUENCE: 3

Glu Asn Tyr Gly Ser His Gly Gly Phe Val Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: recombinant

<400> SEQUENCE: 4

Arg Ala Ser Ser Ser Val Ile Ser Ser Tyr Leu His
1               5                   10

<210> SEQ ID NO 5
<211> LENGTH: 7
<212> TYPE: PRT
<213> ORGANISM: Artificial Sequence
```

```
<220> FEATURE:
<223> OTHER INFORMATION: recombinant

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: recombinant

<400> SEQUENCE: 6

Gln Gln Tyr Asn Gly Tyr Pro Leu Thr
1               5

<210> SEQ ID NO 7
<211> LENGTH: 9
<212> TYPE: PRT
<213> ORGANISM: Artificial Sequence
<220> FEATURE:
<223> OTHER INFORMATION: recombinant

<400> SEQUENCE: 7

Gln Gln Tyr Asn Ser Tyr Pro Leu Thr
1               5

<210> SEQ ID NO 8
<211> LENGTH: 108
<212> TYPE: PRT
<213> ORGANISM: Artificial Sequence
<220> FEATURE:
<223> OTHER INFORMATION: recombinant

<400> SEQUENCE: 8

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ile Ser Ser
                20                  25                  30

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Asp Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asn Gly Tyr Pro
                85                  90                  95

Leu Thr Phe Gly Ala Gly Thr Lys Leu Glu Ile Lys
            100                 105

<210> SEQ ID NO 9
<211> LENGTH: 119
<212> TYPE: PRT
<213> ORGANISM: Artificial Sequence
<220> FEATURE:
<223> OTHER INFORMATION: recombinant

<400> SEQUENCE: 9

Gln Val Gln Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Thr Tyr
```

```
                20                  25                  30
Pro Ile Glu Trp Met Lys Gln Asn His Gly Lys Ser Leu Glu Trp Ile
        35                  40                  45

Gly Asn Phe His Pro Tyr Asn Asp Asp Thr Lys Tyr Asn Glu Lys Phe
    50                  55                  60

Lys Gly Lys Ala Lys Leu Thr Val Glu Lys Ser Ser Thr Thr Val Tyr
65                  70                  75                  80

Leu Glu Leu Ser Arg Leu Thr Ser Asp Asp Ser Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser
        115

<210> SEQ ID NO 10
<211> LENGTH: 108
<212> TYPE: PRT
<213> ORGANISM: Artificial Sequence
<220> FEATURE:
<223> OTHER INFORMATION: recombinant

<400> SEQUENCE: 10

Glu Asn Val Leu Thr Gln Ser Pro Phe Ser Leu Ser Ala Ser Val Gly
1               5                   10                  15

Asp Arg Val Thr Ile Thr Cys Arg Ala Ser Ser Ser Val Ile Ser Ser
            20                  25                  30

Tyr Leu His Trp Tyr Gln Gln Lys Pro Ala Lys Ala Pro Lys Leu Trp
        35                  40                  45

Ile Tyr Ser Thr Ser Asn Leu Ala Ser Gly Val Pro Asp Arg Phe Ser
    50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys Gln Gln Tyr Asn Gly Tyr Pro
                85                  90                  95

Leu Thr Phe Gly Gly Gly Thr Lys Val Glu Ile Lys
            100                 105

<210> SEQ ID NO 11
<211> LENGTH: 324
<212> TYPE: DNA
<213> ORGANISM: Artificial Sequence
<220> FEATURE:
<223> OTHER INFORMATION: recombinant

<400> SEQUENCE: 11
gagaatgtgc tgacacagag cccctttca ctgtctgcat ctgtgggaga ccgggtcaca      60
ataacctgca gggctagctc aagcgtgatc agctcatacc tgcactggta tcagcaaaag    120
cccgccaaag ctcctaagct ctggatctac tccacctcca acttggcatc tggcgtgcct    180
gatagatttt ctgggagcgg ttccgggaca agctataccc tgacgattag ttccctgcaa    240
ccggaggact cgccaccta ttactgtcag cagtacaacg gctacccact gacattcggc     300
ggagggacta aagtcgaaat caag                                            324

<210> SEQ ID NO 12
<211> LENGTH: 128
<212> TYPE: PRT
<213> ORGANISM: Artificial Sequence
<220> FEATURE:
```

<223> OTHER INFORMATION: recombinant

<400> SEQUENCE: 12

Met Ser Val Pro Thr Gln Val Leu Gly Leu Leu Leu Trp Leu Thr
1               5                   10                  15

Asp Ala Arg Cys Glu Asn Val Leu Thr Gln Ser Pro Phe Ser Leu Ser
            20                  25                  30

Ala Ser Val Gly Asp Arg Val Thr Ile Thr Cys Arg Ala Ser Ser Ser
        35                  40                  45

Val Ile Ser Ser Tyr Leu His Trp Tyr Gln Gln Lys Pro Ala Lys Ala
    50                  55                  60

Pro Lys Leu Trp Ile Tyr Ser Thr Ser Asn Leu Ala Ser Gly Val Pro
65                  70                  75                  80

Asp Arg Phe Ser Gly Ser Gly Ser Gly Thr Ser Tyr Thr Leu Thr Ile
                85                  90                  95

Ser Ser Leu Gln Pro Glu Asp Phe Ala Thr Tyr Tyr Cys Gln Gln Tyr
            100                 105                 110

Asn Gly Tyr Pro Leu Thr Phe Gly Gly Gly Thr Lys Val Glu Ile Lys
        115                 120                 125

<210> SEQ ID NO 13
<211> LENGTH: 384
<212> TYPE: DNA
<213> ORGANISM: Artificial Sequence
<220> FEATURE:
<223> OTHER INFORMATION: recombinant

<400> SEQUENCE: 13
atgagtgtgc caactcaggt tctcggattg ctgcttctgt ggcttactga tgcccgctgc      60
gagaatgtgc tgacacagag ccccttttca ctgtctgcat ctgtgggaga ccgggtcaca     120
ataacctgca gggctagctc aagcgtgatc agctcatacc tgcactggta tcagcaaaag     180
cccgccaaag ctcctaagct ctggatctac tccacctcca acttggcatc tggcgtgcct     240
gatagatttt ctgggagcgg ttccgggaca agctataccc tgacgattag ttccctgcaa     300
ccggaggact cgccacctc ttactgtcag cagtacaacg gctacccact gacattcggc     360
ggagggacta agtcgaaat caag                                              384

<210> SEQ ID NO 14
<211> LENGTH: 215
<212> TYPE: PRT
<213> ORGANISM: Artificial Sequence
<220> FEATURE:
<223> OTHER INFORMATION: recombinant

<400> SEQUENCE: 14

Glu Asn Val Leu Thr Gln Ser Pro Phe Ser Leu Ser Ala Ser Val Gly
1               5                   10                  15

Asp Arg Val Thr Ile Thr Cys Arg Ala Ser Ser Ser Val Ile Ser Ser
            20                  25                  30

Tyr Leu His Trp Tyr Gln Gln Lys Pro Ala Lys Ala Pro Lys Leu Trp
        35                  40                  45

Ile Tyr Ser Thr Ser Asn Leu Ala Ser Gly Val Pro Asp Arg Phe Ser
    50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys Gln Gln Tyr Asn Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 15
<211> LENGTH: 645
<212> TYPE: DNA
<213> ORGANISM: Artificial Sequence
<220> FEATURE:
<223> OTHER INFORMATION: recombinant

<400> SEQUENCE: 15
gagaatgtgc tgacacagag cccctttca ctgtctgcat ctgtgggaga ccgggtcaca      60
ataacctgca gggctagctc aagcgtgatc agctcatacc tgcactggta tcagcaaaag   120
cccgccaaag ctcctaagct ctggatctac tccacctcca acttggcatc tggcgtgcct   180
gatagatttt ctgggagcgg ttccgggaca agctataccc tgacgattag ttccctgcaa   240
ccggaggact cgccaccta ttactgtcag cagtacaacg ctacccact gacattcggc      300 ggagggacta aagtcgaaat caagcgtacg gtagcggccc catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac cgagaaacac aaagtctacg cctgcgaagt cacccatcag   600
ggcctgagct cgcccgtcac aaagagcttc aacaggggag agtgt                    645

<210> SEQ ID NO 16
<211> LENGTH: 235
<212> TYPE: PRT
<213> ORGANISM: Artificial Sequence
<220> FEATURE:
<223> OTHER INFORMATION: recombinant

<400> SEQUENCE: 16

Met Ser Val Pro Thr Gln Val Leu Gly Leu Leu Leu Leu Trp Leu Thr
1               5                   10                  15

Asp Ala Arg Cys Glu Asn Val Leu Thr Gln Ser Pro Phe Ser Leu Ser
            20                  25                  30

Ala Ser Val Gly Asp Arg Val Thr Ile Thr Cys Arg Ala Ser Ser Ser
        35                  40                  45

Val Ile Ser Ser Tyr Leu His Trp Tyr Gln Gln Lys Pro Ala Lys Ala
    50                  55                  60

```
Pro Lys Leu Trp Ile Tyr Ser Thr Ser Asn Leu Ala Ser Gly Val Pro
 65                  70                  75                  80

Asp Arg Phe Ser Gly Ser Gly Ser Gly Thr Tyr Thr Leu Thr Ile
                 85                  90                  95

Ser Ser Leu Gln Pro Glu Asp Phe Ala Thr Tyr Tyr Cys Gln Gln Tyr
            100                 105                 110

Asn Gly Tyr Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
        180                 185                 190

Thr Tyr Ser Leu Ser Ser Thr Leu Ser Lys Ala Asp Tyr Glu
    195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 17
<211> LENGTH: 705
<212> TYPE: DNA
<213> ORGANISM: Artificial Sequence
<220> FEATURE:
<223> OTHER INFORMATION: recombinant

<400> SEQUENCE: 17

```
atgagtgtgc caactcaggt tctcggattg ctgcttctgt ggcttactga tgcccgctgc     60
gagaatgtgc tgacacagag ccccttttca ctgtctgcat ctgtgggaga ccgggtcaca    120
ataacctgca gggctagctc aagcgtgatc agctcatacc tgcactggta tcagcaaaag    180
cccgccaaag ctcctaagct ctggatctac tccacctcca acttggcatc tggcgtgcct    240
gatagatttt ctgggagcgg ttccgggaca agctataccc tgacgattag ttccctgcaa    300
ccggaggact cgccaccta ttactgtcag cagtacaacg ctacccact gacattcggc     360
ggagggacta agtcgaaat caagcgtacg gtagcggccc catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag acagcacct acagcctcag cagcaccctg    600
acgctgagca agcagacta cgagaaacac aaagtctacg cctgcgaagt cacccatcag    660
ggcctgagct cgcccgtcac aaagagcttc aacaggggag agtgt              705
```

<210> SEQ ID NO 18
<211> LENGTH: 108
<212> TYPE: PRT
<213> ORGANISM: Artificial Sequence
<220> FEATURE:
<223> OTHER INFORMATION: recombinant

<400> SEQUENCE: 18

```
Glu Asn Val Leu Thr Gln Ser Pro Phe Ser Leu Ser Ala Ser Val Gly
 1               5                  10                  15
```

Asp Arg Val Thr Ile Thr Cys Arg Ala Ser Ser Val Ile Ser Ser
            20                  25                  30

Tyr Leu His Trp Tyr Gln Gln Lys Pro Ala Lys Ala Pro Lys Leu Phe
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Tyr Asn Gly Tyr Pro
                85                  90                  95

Leu Thr Phe Gly Gly Gly Thr Lys Val Glu Ile Lys
            100                 105

<210> SEQ ID NO 19
<211> LENGTH: 324
<212> TYPE: DNA
<213> ORGANISM: Artificial Sequence
<220> FEATURE:
<223> OTHER INFORMATION: recombinant

<400> SEQUENCE: 19
gagaatgtgc tgacacagag ccccttttca ctgtctgcat ctgtgggaga ccgggtcaca    60
ataacctgca gggctagctc aagcgtgatc agctcatacc tgcactggta tcagcaaaag   120
cccgccaaag ctcctaagct cttcatctac tccacctcca acttggcatc tggcgtgcct   180
agcagatttt ctgggagcgg ttccgggaca gactataccc tgacgattag ttccctgcaa   240
ccggaggact cgccaccta ttactgtcag cagtacaacg gctacccact gacattcggc    300
ggagggacta agtcgaaat caag                                          324

<210> SEQ ID NO 20
<211> LENGTH: 108
<212> TYPE: PRT
<213> ORGANISM: Artificial Sequence
<220> FEATURE:
<223> OTHER INFORMATION: recombinant

<400> SEQUENCE: 20

Glu Asn Val Leu Thr Gln Ser Pro Phe Ser Leu Ser Ala Ser Val Gly
1               5                   10                  15

Asp Arg Val Thr Ile Thr Cys Arg Ala Ser Ser Val Ile Ser Ser
            20                  25                  30

Tyr Leu His Trp Tyr Gln Gln Lys Pro Ala Lys Ala Pro Lys Leu Trp
        35                  40                  45

Ile Tyr Ser Thr Ser Asn Leu Ala Ser Gly Val Pro Asp Arg Phe Ser
    50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys
            100                 105

<210> SEQ ID NO 21
<211> LENGTH: 324
<212> TYPE: DNA
<213> ORGANISM: Artificial Sequence
<220> FEATURE:
<223> OTHER INFORMATION: recombinant

<400> SEQUENCE: 21

```
gagaatgtgc tgacacagag ccccttttca ctgtctgcat ctgtgggaga ccgggtcaca      60
ataacctgca gggctagctc aagcgtgatc agctcatacc tgcactggta tcagcaaaag     120
cccgccaaag ctcctaagct ctggatctac tccacctcca acttggcatc tggcgtgcct     180
gatagatttt ctgggagcgg ttccgggaca agctataccc tgacgattag ttccctgcaa     240
ccggaggact cgccaccta ttactgtcag cagtacaact cctacccact gacattcggc      300
ggagggacta aagtcgaaat caag                                            324
```

<210> SEQ ID NO 22
<211> LENGTH: 108
<212> TYPE: PRT
<213> ORGANISM: Artificial Sequence
<220> FEATURE:
<223> OTHER INFORMATION: recombinant

<400> SEQUENCE: 22

```
Glu Asn Val Met Thr Gln Ser Pro Phe Ser Leu Ser Ala Ser Val Gly
1               5                   10                  15

Asp Arg Val Thr Ile Thr Cys Arg Ala Ser Ser Ser Val Ile Ser Ser
            20                  25                  30

Tyr Leu His Trp Tyr Gln Gln Lys Pro Ala Lys Ala Pro Lys Leu Phe
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys
            100                 105
```

<210> SEQ ID NO 23
<211> LENGTH: 324
<212> TYPE: DNA
<213> ORGANISM: Artificial Sequence
<220> FEATURE:
<223> OTHER INFORMATION: recombinant

<400> SEQUENCE: 23

```
gagaatgtga tgacacagag ccccttttca ctgtctgcat ctgtgggaga ccgggtcaca      60
ataacctgca gggctagctc aagcgtgatc agctcatacc tgcactggta tcagcaaaag     120
cccgccaaag ctcctaagct cttcatctac tccacctcca acttggcatc tggcgtgcct     180
agcagatttt ctgggagcgg ttccgggaca gactataccc tgacgattag ttccctgcaa     240
ccggaggact cgccaccta ttactgtcag cagtacaacg gctacccact gacattcggc      300
ggagggacta aagtcgaaat caag                                            324
```

<210> SEQ ID NO 24
<211> LENGTH: 108
<212> TYPE: PRT
<213> ORGANISM: Artificial Sequence
<220> FEATURE:
<223> OTHER INFORMATION: recombinant

<400> SEQUENCE: 24

```
Glu Asn Val Met Thr Gln Ser Pro Phe Ser Leu Ser Ala Ser Val Gly
```

```
              1               5                  10                 15
            Asp Arg Val Thr Ile Thr Cys Arg Ala Ser Ser Ser Val Ile Ser Ser
                            20                  25                 30

Tyr Leu His Trp Tyr Gln Gln Lys Pro Ala Lys Ala Pro Lys Leu Phe
                        35                  40                  45

Ile Tyr Ser Thr Ser Asn Leu Ala Ser Gly Val Pro Ser Arg Phe Ser
                    50                  55                  60

Gly Ser Gly Ser Gly Thr Asp Tyr Thr Leu Thr Ile Ser Ser Leu Gln
            65                  70                  75                  80

Pro Glu Asp Phe Ala Thr Tyr Tyr Cys Gln Gln Tyr Asn Ser Tyr Pro
                                85                  90                  95

Leu Thr Phe Gly Gly Gly Thr Lys Val Glu Ile Lys
                            100                 105

<210> SEQ ID NO 25
<211> LENGTH: 324
<212> TYPE: DNA
<213> ORGANISM: Artificial Sequence
<220> FEATURE:
<223> OTHER INFORMATION: recombinant

<400> SEQUENCE: 25
gagaatgtga tgacacagag ccccttttca ctgtctgcat ctgtgggaga ccgggtcaca    60
ataacctgca gggctagctc aagcgtgatc agctcatacc tgcactggta tcagcaaaag  120
cccgccaaag ctcctaagct cttcatctac tccacctcca acttggcatc tggcgtgcct  180
agcagatttt ctgggagcgg ttccgggaca gactataccc tgacgattag ttccctgcaa  240
ccggaggact cgccaccta ttactgtcag cagtacaact cctacccact gacattcggc  300
ggagggacta aagtcgaaat caag                                         324

<210> SEQ ID NO 26
<211> LENGTH: 108
<212> TYPE: PRT
<213> ORGANISM: Artificial Sequence
<220> FEATURE:
<223> OTHER INFORMATION: recombinant

<400> SEQUENCE: 26

Glu Asn Val Leu Thr Gln Ser Pro Gly Thr Leu Ser Leu Ser Pro Gly
            1               5                  10                  15

Glu Arg Ala Thr Leu Ser Cys Arg Ala Ser Ser Ser Val Ile Ser Ser
                            20                  25                  30

Tyr Leu His Trp Tyr Gln Gln Lys Pro Gly Gln Ala Pro Arg Leu Trp
                        35                  40                  45

Ile Tyr Ser Thr Ser Asn Leu Ala Ser Gly Val Pro Asp Arg Phe Ser
                    50                  55                  60

Gly Ser Gly Ser Gly Thr Ser Tyr Thr Leu Thr Ile Ser Arg Leu Glu
            65                  70                  75                  80

Pro Glu Asp Phe Ala Thr Tyr Tyr Cys Gln Gln Tyr Asn Gly Tyr Pro
                                85                  90                  95

Leu Thr Phe Gly Gly Gly Thr Lys Val Glu Ile Lys
                            100                 105

<210> SEQ ID NO 27
<211> LENGTH: 324
<212> TYPE: DNA
<213> ORGANISM: Artificial Sequence
<220> FEATURE:
```

<223> OTHER INFORMATION: recombinant

<400> SEQUENCE: 27

```
gaaaacgtcc tgacacaatc tccgggtaca ctgtcactga gccctggaga gagagctacc    60
ttgagctgcc gagcctcaag tagcgtgatt agctcctacc tgcactggta tcagcaaaag   120
cctgggcaag caccaaggct gtggatctat agcacctcca atctggcctc tggtgtgcct   180
gacagattct ctggctctgg gtctggaacc tcctacaccc tgactatatc acgcctggag   240
ccagaggact cgccacatac tactgccagc agtacaacgc tatccccct gacctttggc    300
ggagggacta aggtggaaat caaa                                            324
```

<210> SEQ ID NO 28
<211> LENGTH: 108
<212> TYPE: PRT
<213> ORGANISM: Artificial Sequence
<220> FEATURE:
<223> OTHER INFORMATION: recombinant

<400> SEQUENCE: 28

```
Glu Asn Val Leu Thr Gln Ser Pro Gly Thr Leu Ser Leu Ser Pro Gly
 1               5                  10                  15

Glu Arg Ala Thr Leu Ser Cys Arg Ala Ser Ser Val Ile Ser Ser
            20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Val Pro Asp Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys
            100                 105
```

<210> SEQ ID NO 29
<211> LENGTH: 324
<212> TYPE: DNA
<213> ORGANISM: Artificial Sequence
<220> FEATURE:
<223> OTHER INFORMATION: recombinant

<400> SEQUENCE: 29

```
gaaaacgtcc tgacacaatc tccgggtaca ctgtcactga gccctggaga gagagctacc    60
ttgagctgcc gagcctcaag tagcgtgatt agctcctacc tgcactggta tcagcaaaag   120
cctgggcaag caccaaggct gtggatctat agcacctcca atctggcctc tggtgtgcct   180
gacagattct ctggctctgg gtctggaacc tcctacaccc tgactatatc acgcctggag   240
ccagaggact cgccacatac tactgccagc agtacaactc ctatcccct gacctttggc    300
ggagggacta aggtggaaat caaa                                            324
```

<210> SEQ ID NO 30
<211> LENGTH: 119
<212> TYPE: PRT
<213> ORGANISM: Artificial Sequence
<220> FEATURE:
<223> OTHER INFORMATION: recombinant

<400> SEQUENCE: 30

```
Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
            35                  40                  45

Gly Asn Phe His Pro Tyr Asn Asp Asp Thr Lys Tyr Asn Glu Lys Phe
50                  55                  60

Lys Gly Arg Val Thr Met Thr Val Asp Lys Ser Thr Thr Thr Val Tyr
65                  70                  75                  80

Met Glu Leu Ser Ser Leu Arg Ser Glu Asp Thr Ala Val Tyr Tyr Cys
            85                  90                  95

Ala Arg Glu Asn Tyr Gly Ser His Gly Gly Phe Val Tyr Trp Gly Gln
            100                 105                 110

Gly Thr Leu Val Thr Val Ser
            115
```

<210> SEQ ID NO 31
<211> LENGTH: 357
<212> TYPE: DNA
<213> ORGANISM: Artificial Sequence
<220> FEATURE:
<223> OTHER INFORMATION: recombinant

<400> SEQUENCE: 31

```
gaagtgcaac tggtgcagtc tggagctgaa gtgaagaaac ctggtgctag cgtcaaagtg      60
tcctgcaaag ccttcggcta taccttcacc acgtacccaa ttgagtggat gaggcaggca     120
cacggacaag gattggagtg gatcggcaac tttcaccccct acaacgacga cacgaagtac    180
aacgagaagt tcaagggtcg cgtgacaatg accgtcgata agagcacgac cactgttttat   240
atggagctga gctcactgag atccgaagat actgccgtct actattgtgc ccgagagaat    300
tacggatcac acggggqatt tgtttactgg ggacaaggca cactggttac cgtctcg       357
```

<210> SEQ ID NO 32
<211> LENGTH: 138
<212> TYPE: PRT
<213> ORGANISM: Artificial Sequence
<220> FEATURE:
<223> OTHER INFORMATION: recombinant

<400> SEQUENCE: 32

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Phe Gly Tyr Thr Phe
            35                  40                  45

Thr Thr Tyr Pro Ile Glu Trp Met Arg Gln Ala His Gly Gln Gly Leu
50                  55                  60

Glu Trp Ile Gly Asn Phe His Pro Tyr Asn Asp Asp Thr Lys Tyr Asn
65                  70                  75                  80

Glu Lys Phe Lys Gly Arg Val Thr Met Thr Val Asp Lys Ser Thr Thr
            85                  90                  95

Thr Val Tyr Met Glu Leu Ser Ser Leu Arg Ser Glu Asp Thr Ala Val
            100                 105                 110

Tyr Tyr Cys Ala Arg Glu Asn Tyr Gly Ser His Gly Gly Phe Val Tyr
            115                 120                 125
```

Trp Gly Gln Gly Thr Leu Val Thr Val Ser
            130                 135

<210> SEQ ID NO 33
<211> LENGTH: 414
<212> TYPE: DNA
<213> ORGANISM: Artificial Sequence
<220> FEATURE:
<223> OTHER INFORMATION: recombinant

<400> SEQUENCE: 33
atggaatgga gctgggtctt tctcttcttc ctgtccgtga caactggtgt gcactctgaa     60
gtgcaactgg tgcagtctgg agctgaagtg aagaaacctg gtgctagcgt caaagtgtcc    120
tgcaaagcct tcggctatac cttcaccacg tacccaattg agtggatgag gcaggcacac    180
ggacaaggat tggagtggat cggcaacttt caccctaca acgacgacac gaagtacaac    240
gagaagttca gggtcgcgt gacaatgacc gtcgataaga gcacgaccac tgtttatatg    300
gagctgagct cactgagatc cgaagatact gccgtctact attgtgcccg agagaattac    360
ggatcacacg ggggatttgt ttactgggga caaggcacac tggttaccgt ctcg          414

<210> SEQ ID NO 34
<211> LENGTH: 447
<212> TYPE: PRT
<213> ORGANISM: Artificial Sequence
<220> FEATURE:
<223> OTHER INFORMATION: recombinant

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45

Gly Asn Phe His Pro Tyr Asn Asp Asp Thr Lys Tyr Asn Glu Lys Phe
    50                  55                  60

Lys Gly Arg Val Thr Met Thr Val Asp Lys Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

| Pro | Cys | Pro | Cys | Pro | Ala | Pro | Glu | Phe | Leu | Gly | Gly | Pro | Ser | Val |
| 225 | | | | 230 | | | | | 235 | | | | | 240 |

Phe Leu Phe Pro Pro Lys Pro Lys Asp Thr Leu Met Ile Ser Arg Thr
                245                    250                    255

Pro Glu Val Thr Cys Val Val Val Asp Val Ser Gln Glu Asp Pro Glu
        260                    265                    270

Val Gln Phe Asn Trp Tyr Val Asp Gly Val Glu Val His Asn Ala Lys
            275                    280                    285

Thr Lys Pro Arg Glu Glu Gln Phe Asn Ser Thr Tyr Arg Val Val Ser
    290                    295                    300

Val Leu Thr Val Leu His Gln Asp Trp Leu Asn Gly Lys Glu Tyr Lys
305                    310                    315                    320

Cys Lys Val Ser Asn Lys Gly Leu Pro Ser Ser Ile Glu Lys Thr Ile
                325                    330                    335

Ser Lys Ala Lys Gly Gln Pro Arg Glu Pro Gln Val Tyr Thr Leu Pro
            340                    345                    350

Pro Ser Gln Glu Glu Met Thr Lys Asn Gln Val Ser Leu Thr Cys Leu
        355                    360                    365

Val Lys Gly Phe Tyr Pro Ser Asp Ile Ala Val Glu Trp Ser Asn
370                    375                    380

Gly Gln Pro Glu Asn Asn Tyr Lys Thr Thr Pro Pro Val Leu Asp Ser
385                    390                    395                    400

Asp Gly Ser Phe Phe Leu Tyr Ser Arg Leu Thr Val Asp Lys Ser Arg
                405                    410                    415

Trp Gln Glu Gly Asn Val Phe Ser Cys Ser Val Met His Glu Ala Leu
            420                    425                    430

His Asn His Tyr Thr Gln Lys Ser Leu Ser Leu Ser Leu Gly Lys
        435                    440                    445

<210> SEQ ID NO 35
<211> LENGTH: 1948
<212> TYPE: DNA
<213> ORGANISM: Artificial Sequence
<220> FEATURE:
<223> OTHER INFORMATION: recombinant

<400> SEQUENCE: 35

```
gaagtgcaac tggtgcagtc tggagctgaa gtgaagaaac tggtgctagc gtcaaagtg      60 tcctgcaaag ccttcggcta taccttcacc acgtacccaa ttgagtggat gaggcaggca     120
cacggacaag gattggagtg gatcggcaac tttcacccct acaacgacga cacgaagtac    180
aacgagaagt tcaagggtcg cgtgacaatg accgtcgata gagcacgac  cactgtttat    240 atggagctga gctcactgag atccgaagat actgccgtct actattgtgc cagagagaat    300
tacggatcac acgggggatt tgtttactgg ggacaaggca cactggttac cgtctcgagc    360
gcttctacaa agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttggtgag    660
aggccagcac aggagggag  ggtgtctgct ggaagccagg ctcagccctc ctgcctggac    720
gcaccccggc tgtgcagccc cagcccaggg cagcaaggca tgccccatct gtctcctcac    780
```

```
ccggaggcct ctgaccaccc cactcatgcc cagggagagg gtcttctgga ttttccacc      840
aggctccggg cagccacagg ctggatgccc tacccagg ccctgcgcat acagggcag        900
gtgctgcgct cagacctgcc aagagccata tccgggagga ccctgcccct gacctaagcc     960
caccccaaag gccaaactct ccactccctc agctcagaca ccttctctcc tcccagatct    1020
gagtaactcc caatcttctc tctgcagagt ccaaatatgg tcccccatgc ccaccatgcc    1080
caggtaagcc aacccaggcc tcgccctcca gctcaaggcg ggacaggtgc cctagagtag    1140
cctgcatcca gggacaggcc ccagccgggt gctgacgcat ccacctccat ctcttcctca    1200
gcacctgagt cctgggggg accatcagtc ttcctgttcc ccaaaaacc caaggacact      1260
ctcatgatct cccggacccc tgaggtcacg tgcgtggtgg tggacgtgag ccaggaagac    1320
cccgaggtcc agttcaactg gtacgtggat ggcgtggagg tgcataatgc caagacaaag    1380
ccgcgggagg agcagttcaa cagcacgtac cgtgtggtca gcgtcctcac cgtcctgcac    1440
caggactggc tgaacggcaa ggagtacaag tgcaaggtct ccaacaaagg cctcccgtcc    1500
tccatcgaga aaaccatctc caaagccaaa ggtgggaccc acggggtgcg agggccacat    1560
ggacagaggt cagctcggcc caccctctgc cctgggagtg accgctgtgc caacctctgt    1620
ccctacaggg cagccccgag agccacaggt gtacaccctg cccccatccc aggaggagat    1680
gaccaagaac caggtcagcc tgacctgcct ggtcaaaggc ttctacccca gcgacatcgc    1740
cgtggagtgg gagagcaatg ggcagccgga gaacaactac aagaccacgc ctcccgtgct    1800
ggactccgac ggctccttct cctctacag caggctaacc gtggacaaga gcaggtggca    1860
ggaggggaat gtcttctcat gctccgtgat gcatgaggct ctgcacaacc actacacaca    1920
gaagagcctc tccctgtctc tgggtaaa                                       1948

<210> SEQ ID NO 36
<211> LENGTH: 466
<212> TYPE: PRT
<213> ORGANISM: Artificial Sequence
<220> FEATURE:
<223> OTHER INFORMATION: recombinant

<400> SEQUENCE: 36

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Phe Gly Tyr Thr Phe
        35                  40                  45

Thr Thr Tyr Pro Ile Glu Trp Met Arg Gln Ala His Gly Gln Gly Leu
    50                  55                  60

Glu Trp Ile Gly Asn Phe His Pro Tyr Asn Asp Asp Thr Lys Tyr Asn
65                  70                  75                  80

Glu Lys Phe Lys Gly Arg Val Thr Met Thr Val Asp Lys Ser Thr Thr
                85                  90                  95

Thr Val Tyr Met Glu Leu Ser Ser Leu Arg Ser Glu Asp Thr Ala Val
            100                 105                 110

Tyr Tyr Cys Ala Arg Glu Asn Tyr Gly Ser His Gly Gly Phe Val Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160
```

```
            Thr Ala Ala Leu Gly Cys Leu Val Lys Asp Tyr Phe Pro Glu Pro Val
                            165                 170                 175

Thr Val Ser Trp Asn Ser Gly Ala Leu Thr Ser Gly Val His Thr Phe
                        180                 185                 190

Pro Ala Val Leu Gln Ser Ser Gly Leu Tyr Ser Leu Ser Ser Val Val
                    195                 200                 205

Thr Val Pro Ser Ser Ser Leu Gly Thr Lys Thr Tyr Thr Cys Asn Val
                210                 215                 220

Asp His Lys Pro Ser Asn Thr Lys Val Asp Lys Arg Val Glu Ser Lys
            225                 230                 235                 240

Tyr Gly Pro Pro Cys Pro Pro Cys Pro Ala Pro Glu Phe Leu Gly Gly
                            245                 250                 255

Pro Ser Val Phe Leu Phe Pro Pro Lys Pro Lys Asp Thr Leu Met Ile
                        260                 265                 270

Ser Arg Thr Pro Glu Val Thr Cys Val Val Val Asp Val Ser Gln Glu
                    275                 280                 285

Asp Pro Glu Val Gln Phe Asn Trp Tyr Val Asp Gly Val Glu Val His
                290                 295                 300

Asn Ala Lys Thr Lys Pro Arg Glu Glu Gln Phe Asn Ser Thr Tyr Arg
            305                 310                 315                 320

Val Val Ser Val Leu Thr Val Leu His Gln Asp Trp Leu Asn Gly Lys
                            325                 330                 335

Glu Tyr Lys Cys Lys Val Ser Asn Lys Gly Leu Pro Ser Ser Ile Glu
                        340                 345                 350

Lys Thr Ile Ser Lys Ala Lys Gly Gln Pro Arg Glu Pro Gln Val Tyr
                    355                 360                 365

Thr Leu Pro Pro Ser Gln Glu Glu Met Thr Lys Asn Gln Val Ser Leu
                370                 375                 380

Thr Cys Leu Val Lys Gly Phe Tyr Pro Ser Asp Ile Ala Val Glu Trp
            385                 390                 395                 400

Glu Ser Asn Gly Gln Pro Glu Asn Asn Tyr Lys Thr Thr Pro Pro Val
                            405                 410                 415

Leu Asp Ser Asp Gly Ser Phe Phe Leu Tyr Ser Arg Leu Thr Val Asp
                        420                 425                 430

Lys Ser Arg Trp Gln Glu Gly Asn Val Phe Ser Cys Ser Val Met His
                    435                 440                 445

Glu Ala Leu His Asn His Tyr Thr Gln Lys Ser Leu Ser Leu Ser Leu
                450                 455                 460

Gly Lys
            465

<210> SEQ ID NO 37
<211> LENGTH: 2005
<212> TYPE: DNA
<213> ORGANISM: Artificial Sequence
<220> FEATURE:
<223> OTHER INFORMATION: recombinant

<400> SEQUENCE: 37
atggaatgga gctgggtctt tctcttcttc ctgtccgtga caactggtgt gcactctgaa      60
gtgcaactgg tgcagtctgg agctgaagtg aagaaacctg gtgctagcgt caaagtgtcc     120
tgcaaagcct tcggctatac cttcaccacg tacccaattg agtggatgag gcaggcacac     180
ggacaaggat tggagtggat cggcaacttt caccccctaca acgacgacac gaagtacaac     240
```

-continued

```
gagaagttca agggtcgcgt gacaatgacc gtcgataaga gcacgaccac tgtttatatg    300
gagctgagct cactgagatc cgaagatact gccgtctact attgtgcccg agagaattac    360
ggatcacacg ggggatttgt ttactgggga caaggcacac tggttaccgt ctcgagcgct    420
tctacaaagg gcccatccgt cttcccctg gcgccctgct ccaggagcac tccgagagc     480 acagccgccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac gaagacctac    660
acctgcaacg tagatcacaa gcccagcaac accaaggtgg acaagagagt tggtgagagg    720
ccagcacagg gagggagggt gtctgctgga agccaggctc agccctcctg cctggacgca    780
ccccggctgt gcagcccag cccagggcag caaggcatgc cccatctgtc tcctcacccg    840
gaggcctctg accaccccac tcatgcccag ggagagggtc ttctggatt ttccaccagg   900 ctccgggcag ccacaggctg gatgccccta ccccaggccc tgcgcataca ggggcaggtg    960
ctgcgctcag acctgccaag agccatatcc gggaggaccc tgcccctgac ctaagcccac   1020
cccaaaggcc aaactctcca ctccctcagc tcagacacct tctctcctcc cagatctgag   1080
taactcccaa tcttctctct gcagagtcca aatatggtcc cccatgccca ccatgccag    1140 gtaagccaac ccaggcctcg ccctccagct caaggcggga caggtgccct agagtagcct   1200
gcatccaggg acaggcccca gccgggtgct gacgcatcca cctccatctc ttcctcagca   1260
cctgagttcc tggggggacc atcagtcttc ctgttccccc caaaacccaa ggacactctc   1320
atgatctccc ggacccctga ggtcacgtgc gtggtggtgg acgtgagcca ggaagacccc   1380
gaggtccagt tcaactggta cgtggatggc gtggaggtgc ataatgccaa gacaaagccg   1440
cgggaggagc agttcaacag cacgtaccgt gtggtcagcg tcctcaccgt cctgcaccag   1500
gactggctga acggcaagga gtacaagtgc aaggtctcca acaaaggcct cccgtcctcc   1560
atcgagaaaa ccatctccaa agccaaaggt gggacccacg gggtgcgagg gccacatgga   1620
cagaggtcag ctcggcccac cctctgccct gggagtgacc gctgtgccaa cctctgtccc   1680
tacagggcag ccccgagagc cacaggtgta ccctgccc ccatcccagg aggagatgac    1740
caagaaccag gtcagcctga cctgcctggt caaaggcttc taccccagcg acatcgccgt   1800
ggagtgggag agcaatgggc agccggagaa caactacaag accacgcctc ccgtgctgga   1860
ctccgacggc tccttcttcc tctacagcag gctaaccgtg gacaagagca ggtggcagga   1920
ggggaatgtc ttctcatgct ccgtgatgca tgaggctctg cacaaccact acacacagaa   1980
gagcctctcc ctgtctctgg gtaaa                                        2005
```

<210> SEQ ID NO 38
<211> LENGTH: 119
<212> TYPE: PRT
<213> ORGANISM: Artificial Sequence
<220> FEATURE:
<223> OTHER INFORMATION: recombinant

<400> SEQUENCE: 38

```
Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45
```

Gly Asn Phe His Pro Tyr Asn Asp Asp Thr Lys Tyr Asn Glu Lys Phe
            50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
                100                 105                 110

Gly Thr Leu Val Thr Val Ser
        115

<210> SEQ ID NO 39
<211> LENGTH: 357
<212> TYPE: DNA
<213> ORGANISM: Artificial Sequence
<220> FEATURE:
<223> OTHER INFORMATION: recombinant

<400> SEQUENCE: 39
gaagtgcaac tggtgcagtc tggagctgaa gtgaagaaac ctggtgctag cgtcaaagtg      60
tcctgcaaag ccttcggcta taccttcacc acgtacccaa ttgagtggat gaggcaggca     120
cacggacaag gattggagtg gatcggcaac tttcacccct acaacgacga cacgaagtac     180
aacgagaagt tcaagggtcg cgtgacaatg accagggata ccagcacgag cactgtttat     240
atggagctga gctcactgag atccgaagat actgccgtct actattgtgc ccgagagaat     300
tacggatcac acgggggatt tgtttactgg ggacaaggca cactggttac cgtctcg       357

<210> SEQ ID NO 40
<211> LENGTH: 119
<212> TYPE: PRT
<213> ORGANISM: Artificial Sequence
<220> FEATURE:
<223> OTHER INFORMATION: recombinant

<400> SEQUENCE: 40

Glu Val Gln Leu Val Gln Ser Gly Ala Glu Val Lys Lys Pro Gly Ala
 1               5                  10                  15

Ser Val Lys Val Ser Cys Lys Ala Phe Gly Tyr Thr Phe Thr Thr Tyr
                20                  25                  30

Pro Ile Glu Trp Val Arg Gln Ala Pro Gly Gln Gly Leu Glu Trp Met
            35                  40                  45

Gly Asn Phe His Pro Tyr Asn Asp Asp Thr Lys Tyr Asn Glu Lys Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
                100                 105                 110

Gly Thr Leu Val Thr Val Ser
        115

<210> SEQ ID NO 41
<211> LENGTH: 357
<212> TYPE: DNA
<213> ORGANISM: Artificial Sequence
<220> FEATURE:
<223> OTHER INFORMATION: recombinant

<400> SEQUENCE: 41

```
gaagtgcaac tggtgcagtc tggagctgaa gtgaagaaac ctggtgctag cgtcaaagtg    60
tcctgcaaag ccttcggcta taccttcacc acgtacccaa ttgagtgggt gaggcaggca   120
cccggacaag gattggagtg gatgggcaac tttcacccct acaacgacga cacgaagtac   180
aacgagaagt tcaagggtcg cgtgacaatg accagggata ccagcacgag cactgtttat   240
atggagctga gctcactgag atccgaagat actgccgtct actattgtgc ccgagagaat   300
tacggatcac acgggggatt tgtttactgg ggacaaggca cactggttac cgtctcg     357
```

<210> SEQ ID NO 42
<211> LENGTH: 119
<212> TYPE: PRT
<213> ORGANISM: Artificial Sequence
<220> FEATURE:
<223> OTHER INFORMATION: recombinant

<400> SEQUENCE: 42

```
Glu Val Gln Leu Val Gln Ser Gly Ala Glu Val Lys Lys Pro Gly Ser
1               5                  10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45

Gly Asn Phe His Pro Tyr Asn Asp Asp Thr Lys Tyr Asn Glu Lys Phe
    50                  55                  60

Lys Gly Arg Val Thr Ile Thr Val Asp Lys Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser
        115
```

<210> SEQ ID NO 43
<211> LENGTH: 357
<212> TYPE: DNA
<213> ORGANISM: Artificial Sequence
<220> FEATURE:
<223> OTHER INFORMATION: recombinant

<400> SEQUENCE: 43

```
gaagtgcagc ttgtgcaaag cggcgctgag gtcaaaaagc ccggatcaag cgtgaaagtc    60
tcatgcaaag ccttcggcta caccttcaca acgtaccccta tcgagtggat gaggcaggct   120
catggccaag gactggaatg gattgggaac ttccacccat acaacgacga caccaagtac   180
aacgagaagt tcaagggggcg cgttactata accgtggaca gagcactac caccgtgtac   240
atggagctga gcagtctgag aagcgaggat acagccgtgt actattgtgc acggagaaat   300
tatggctctc acggcggatt tgtgtactgg ggccaaggaa cactggttac tgtctcg     357
```

<210> SEQ ID NO 44
<211> LENGTH: 119
<212> TYPE: PRT
<213> ORGANISM: Artificial Sequence
<220> FEATURE:
<223> OTHER INFORMATION: recombinant

<400> SEQUENCE: 44

Glu Val Gln Leu Val Gln Ser Gly Ala Glu Val Lys Lys Pro Gly Ser
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45

Gly Asn Phe His Pro Tyr Asn Asp Asp Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser
            115

<210> SEQ ID NO 45
<211> LENGTH: 357
<212> TYPE: DNA
<213> ORGANISM: Artificial Sequence
<220> FEATURE:
<223> OTHER INFORMATION: recombinant

<400> SEQUENCE: 45

```
gaagtgcagc ttgtgcaaag cggcgctgag gtcaaaaagc ccggatcaag cgtgaaagtc      60
tcatgcaaag ccttcggcta caccttcaca acgtacccta tcgagtggat gaggcaggct     120
catggccaag gactggaatg gattgggaac ttccacccat acaacgacga caccaagtac     180
aacgagaagt tcaaggggcg cgttactata accgccgaca gagcactagc accgcctac      240
atggagctga gcagtctgag aagcgaggat acagccgtgt actattgtgc acggagaat      300
tatggctctc acggcggatt tgtgtactgg ggccaaggaa cactggttac tgtctcg        357
```

<210> SEQ ID NO 46
<211> LENGTH: 119
<212> TYPE: PRT
<213> ORGANISM: Artificial Sequence
<220> FEATURE:
<223> OTHER INFORMATION: recombinant

<400> SEQUENCE: 46

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Pro Ile Glu Trp Val Arg Gln Ala Pro Gly Gln Gly Leu Glu Trp Met
        35                  40                  45

Gly Asn Phe His Pro Tyr Asn Asp Asp Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser

<210> SEQ ID NO 47
<211> LENGTH: 357
<212> TYPE: DNA
<213> ORGANISM: Artificial Sequence
<220> FEATURE:
<223> OTHER INFORMATION: recombinant

<400> SEQUENCE: 47

```
gaagtgcagc ttgtgcaaag cggcgctgag gtcaaaaagc ccggatcaag cgtgaaagtc      60
tcatgcaaag ccagcggcta caccttcaca acgtacccta tcgagtgggt gaggcaggct     120
cccggccaag gactggaatg gatggggaac ttccacccat acaacgacga caccaagtac     180
aacgagaagt tcaaggggcg cgttactata accgccgaca gagcactag caccgcctac      240
atggagctga gcagtctgag aagcgaggat acagccgtgt actattgtgc acgggagaat     300
tatggctctc acggcggatt tgtgtactgg ggccaaggaa cactggttac tgtctcg        357
```

<210> SEQ ID NO 48
<211> LENGTH: 107
<212> TYPE: PRT
<213> ORGANISM: Artificial Sequence
<220> FEATURE:
<223> OTHER INFORMATION: recombinant

<400> SEQUENCE: 48

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys
            100                 105

<210> SEQ ID NO 49
<211> LENGTH: 321
<212> TYPE: DNA
<213> ORGANISM: Artificial Sequence
<220> FEATURE:
<223> OTHER INFORMATION: recombinant

<400> SEQUENCE: 49

```
gccatccgga tgacccagtc tccattctcc ctgtctgcat ctgtaggaga cagagtcacc      60
atcacttgct gggccagtca gggcattagc agttatttag cctggtatca gcaaaaacca     120
gcaaaagccc ctaagctctt catctattat gcatccagtt tgcaaagtgg ggtcccatca     180
aggttcagcg gcagtggatc tgggacggat tacactctca ccatcagcag cctgcagcct     240
gaagattttg caacttatta ctgtcaacag tattatagta cccctctcac tttcggcgga     300
gggaccaagg tggagatcaa a                                               321
```

<210> SEQ ID NO 50

<211> LENGTH: 108
<212> TYPE: PRT
<213> ORGANISM: Artificial Sequence
<220> FEATURE:
<223> OTHER INFORMATION: recombinant

<400> SEQUENCE: 50

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Leu Thr Phe Gly Gly Gly Thr Lys Val Glu Ile Lys
            100                 105
```

<210> SEQ ID NO 51
<211> LENGTH: 324
<212> TYPE: DNA
<213> ORGANISM: Artificial Sequence
<220> FEATURE:
<223> OTHER INFORMATION: recombinant

<400> SEQUENCE: 51

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctct cactttcggc     300
ggagggacca aggtggagat caaa                                            324
```

<210> SEQ ID NO 52
<211> LENGTH: 112
<212> TYPE: PRT
<213> ORGANISM: Artificial Sequence
<220> FEATURE:
<223> OTHER INFORMATION: recombinant

<400> SEQUENCE: 52

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
```

-continued

```
Ala Arg Tyr Phe Asp Tyr Trp Gly Gln Gly Thr Leu Val Thr Val Ser
        100                 105                 110
```

<210> SEQ ID NO 53
<211> LENGTH: 336
<212> TYPE: DNA
<213> ORGANISM: Artificial Sequence
<220> FEATURE:
<223> OTHER INFORMATION: recombinant

<400> SEQUENCE: 53

```
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg atgggaata atcaaccct gtggtggtag cacaagctac        180
gcacagaagt tccagggcag agtcaccatg accaggaca cgtccacgag cacagtctac      240
atggagctga gcagcctgag atctgaggac acggccgtgt attactgtgc gagatacttt     300
gactactggg gccagggaac cctggtcacc gtctcc                                336
```

<210> SEQ ID NO 54
<211> LENGTH: 112
<212> TYPE: PRT
<213> ORGANISM: Artificial Sequence
<220> FEATURE:
<223> OTHER INFORMATION: recombinant

<400> SEQUENCE: 54

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Phe Asp Tyr Trp Gly Gln Gly Thr Leu Val Thr Val Ser
        100                 105                 110
```

<210> SEQ ID NO 55
<211> LENGTH: 336
<212> TYPE: DNA
<213> ORGANISM: Artificial Sequence
<220> FEATURE:
<223> OTHER INFORMATION: recombinant

<400> SEQUENCE: 55

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg atgggaggg atcatcccta tctttggtac agcaaactac       180
gcacagaagt tccagggcag agtcacgatt accgcggaca atccacgag cacagcctac      240
atggagctga gcagcctgag atctgaggac acggccgtgt attactgtgc gagatacttt     300
gactactggg gccagggaac cctggtcacc gtctcc                                336
```

-continued

```
<210> SEQ ID NO 56
<211> LENGTH: 14
<212> TYPE: PRT
<213> ORGANISM: Artificial Sequence
<220> FEATURE:
<223> OTHER INFORMATION: recombinant

<400> SEQUENCE: 56

Tyr Phe Asp Tyr Trp Gly Gln Gly Thr Leu Val Thr Val Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: recombinant

<400> SEQUENCE: 57

Leu Thr Phe Gly Gly Gly Thr Lys Val Glu Ile Lys
1               5                   10

<210> SEQ ID NO 58
<211> LENGTH: 446
<212> TYPE: PRT
<213> ORGANISM: Artificial Sequence
<220> FEATURE:
<223> OTHER INFORMATION: recombinant

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45

Gly Asn Phe His Pro Tyr Asn Asp Asp Thr Lys Tyr Asn Glu Lys Phe
    50                  55                  60

Lys Gly Arg Val Thr Met Thr Val Asp Lys Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 59
<211> LENGTH: 1945
<212> TYPE: DNA
<213> ORGANISM: Artificial Sequence
<220> FEATURE:
<223> OTHER INFORMATION: recombinant

<400> SEQUENCE: 59
gaagtgcaac tggtgcagtc tggagctgaa gtgaagaaac ctggtgctag cgtcaaagtg     60
tcctgcaaag ccttcggcta taccttcacc acgtacccaa ttgagtggat gaggcaggca    120
cacggacaag gattggagtg gatcggcaac tttcacccct acaacgacga cacgaagtac    180
aacgagaagt tcaagggtcg cgtgacaatg accgtcgata gagcacgac cactgtttat     240 atggagctga gctcactgag atccgaagat actgccgtct actattgtgc ccgagagaat    300
tacggatcac acgggggatt tgtttactgg ggacaaggca cactggttac cgtctcgagc    360
gcttctacaa agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttggtgag    660
aggccagcac agggagggag ggtgtctgct ggaagccagg ctcagccctc ctgcctggac    720 gcacccggc tgtgcagccc cagcccaggg cagcaaggca tgccccatct gtctcctcac    780
ccggaggcct ctgaccaccc cactcatgcc caggagagg tcttctgga ttttccacc      840 aggctccggg cagccacagg ctggatgccc ctaccccagg ccctgcgcat acaggggcag    900

```
gtgctgcgct cagacctgcc aagagccata tccgggagga ccctgcccct gacctaagcc    960
caccccaaag gccaaactct ccactccctc agctcagaca ccttctctcc tcccagatct   1020
gagtaactcc caatcttctc tctgcagagt ccaaatatgg tcccccatgc ccaccatgcc   1080
caggtaagcc aacccaggcc tcgccctcca gctcaaggcg ggacaggtgc ctagagtag    1140 cctgcatcca gggacaggcc ccagccgggt gctgacgcat ccacctccat ctcttcctca   1200
gcacctgagt tcctgggggg accatcagtc ttcctgttcc ccccaaaacc caaggacact   1260
ctcatgatct cccggacccc tgaggtcacg tgcgtggtgg tggacgtgag ccaggaagac   1320
cccgaggtcc agttcaactg gtacgtggat ggcgtggagg tgcataatgc caagacaaag   1380
ccgcgggagg agcagttcaa cagcacgtac cgtgtggtca gcgtcctcac cgtcctgcac   1440
caggactggc tgaacggcaa ggagtacaag tgcaaggtct ccaacaaagg cctcccgtcc   1500
tccatcgaga aaaccatctc caaagccaaa ggtgggaccc acggggtgcg agggccacat   1560
ggacagaggt cagctcggcc caccctctgc cctgggagtg accgctgtgc caacctctgt   1620
ccctacaggg cagccccgag agccacaggt gtacaccctg cccccatccc aggaggagat   1680
gaccaagaac caggtcagcc tgacctgcct ggtcaaaggc ttctacccca gcgacatcgc   1740
cgtggagtgg gagagcaatg ggcagccgga gaacaactac aagaccacgc ctcccgtgct   1800
ggactccgac ggctccttct tcctctacag caggctaacc gtggacaaga gcaggtggca   1860 ggagggaat gtcttctcat gctccgtgat gcatgaggct ctgcacaacc actacacaca    1920
gaagagcctc tccctgtctc tgggt                                         1945
```

<210> SEQ ID NO 60
<211> LENGTH: 465
<212> TYPE: PRT
<213> ORGANISM: Artificial Sequence
<220> FEATURE:
<223> OTHER INFORMATION: recombinant

<400> SEQUENCE: 60

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Phe Gly Tyr Thr Phe
        35                  40                  45

Thr Thr Tyr Pro Ile Glu Trp Met Arg Gln Ala His Gly Gln Gly Leu
    50                  55                  60

Glu Trp Ile Gly Asn Phe His Pro Tyr Asn Asp Asp Thr Lys Tyr Asn
65                  70                  75                  80

Glu Lys Phe Lys Gly Arg Val Thr Met Thr Val Asp Lys Ser Thr Thr
                85                  90                  95

Thr Val Tyr Met Glu Leu Ser Ser Leu Arg Ser Glu Asp Thr Ala Val
            100                 105                 110

Tyr Tyr Cys Ala Arg Glu Asn Tyr Gly Ser His Gly Gly Phe Val Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175
```

```
Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
            275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
    450                 455                 460

Gly
465

<210> SEQ ID NO 61
<211> LENGTH: 2002
<212> TYPE: DNA
<213> ORGANISM: Artificial Sequence
<220> FEATURE:
<223> OTHER INFORMATION: recombinant

<400> SEQUENCE: 61
atggaatgga gctgggtctt tctcttcttc ctgtccgtga caactggtgt gcactctgaa      60
gtgcaactgg tgcagtctgg agctgaagtg aagaaacctg gtgctagcgt caaagtgtcc     120
tgcaaagcct tcggctatac cttcaccacg tacccaattg agtggatgag gcaggcacac     180
ggacaaggat tggagtggat cggcaacttt caccccctaca acgacgacac gaagtacaac     240
gagaagttca gggtcgcgt gacaatgacc gtcgataaga gcacgaccac tgtttatatg     300
gagctgagct cactgagatc cgaagatact gccgtctact attgtgcccg agagaattac     360
```

-continued

```
ggatcacacg gggatttgt tactggga caaggcacac tggttaccgt ctcgagcgct      420
tctacaaagg gcccatccgt cttcccctg gcgccctgct ccaggagcac ctccgagagc      480
acagccgccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac gaagacctac      660
acctgcaacg tagatcacaa gcccagcaac accaaggtgg acaagagagt tggtgagagg      720
ccagcacagg agggagggt gtctgctgga agccaggctc agccctcctg cctggacgca      780
ccccggctgt gcagcccag cccagggcag caaggcatgc cccatctgtc cctcacccg      840
gaggcctctg accaccccac tcatgcccag ggagagggtc ttctggattt ttccaccagg      900
ctccgggcag ccacaggctg gatgccccta ccccaggccc tgcgcataca ggggcaggtg      960
ctgcgctcag acctgccaag agccatatcc gggaggaccc tgcccctgac taagcccac     1020
cccaaaggcc aaactctcca ctccctcagc tcagacacct tctctcctcc cagatctgag     1080
taactcccaa tcttctctct gcagagtcca aatatggtcc cccatgccca ccatgcccag     1140
gtaagccaac ccaggcctcg ccctccagct caaggcggga caggtgccct agagtagcct     1200
gcatccaggg acaggcccca gccgggtgct gacgcatcca cctccatctc ttcctcagca     1260
cctgagttcc tggggggacc atcagtcttc ctgttcccc caaaacccaa ggacactctc     1320
atgatctccc ggacccctga ggtcacgtgc gtggtggtgg acgtgagcca ggaagacccc     1380
gaggtccagt tcaactggta cgtggatggc gtggaggtgc ataatgccaa gacaaagccg     1440
cgggaggagc agttcaacag cacgtaccgt gtggtcagcg tcctcaccgt cctgcaccag     1500
gactggctga acggcaagga gtacaagtgc aaggtctcca acaaaggcct cccgtcctcc     1560
atcgagaaaa ccatctccaa agccaaaggt gggacccacg gggtgcgagg gccacatgga     1620
cagaggtcag ctcggcccac cctctgccct gggagtgacc gctgtgccaa cctctgtccc     1680
tacagggcag ccccgagagc cacaggtgta caccctgccc ccatcccagg aggagatgac     1740
caagaaccag gtcagcctga cctgcctggt caaaggcttc taccccagcg acatcgccgt     1800
ggagtgggag agcaatgggc agccggagaa caactacaag accacgcctc ccgtgctgga     1860
ctccgacggc tccttcttcc tctacagcag gctaaccgtg gacaagagca ggtggcagga     1920
ggggaatgtc ttctcatgct ccgtgatgca tgaggctctg cacaaccact acacacagaa     1980
gagcctctcc ctgtctctgg gt                                             2002
```

<210> SEQ ID NO 62
<211> LENGTH: 449
<212> TYPE: PRT
<213> ORGANISM: Artificial Sequence
<220> FEATURE:
<223> OTHER INFORMATION: recombinant

<400> SEQUENCE: 62

```
Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Ala His Gly Gln Gly Leu Glu Trp Ile
        35                  40                  45

Gly Asn Phe His Pro Tyr Asn Asp Asp Thr Lys Tyr Asn Glu Lys Phe
    50                  55                  60
```

```
Lys Gly Arg Val Thr Met Thr Val Asp Lys Ser Thr Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Asn Tyr Gly Ser His Gly Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 63
<211> LENGTH: 1953
<212> TYPE: DNA
<213> ORGANISM: Artificial Sequence
```

<220> FEATURE:
<223> OTHER INFORMATION: recombinant

<400> SEQUENCE: 63

```
gaagtgcaac tggtgcagtc tggagctgaa gtgaagaaac ctggtgctag cgtcaaagtg      60
tcctgcaaag ccttcggcta taccttcacc acgtacccaa ttgagtggat gaggcaggca     120
cacggacaag gattggagtg gatcggcaac tttcacccct acaacgacga cacgaagtac     180
aacgagaagt tcaagggtcg cgtgacaatg accgtcgata gagcacgac cactgttttat     240
atggagctga gctcactgag atccgaagat actgccgtct actattgtgc ccgagagaat     300
tacggatcac acgggggatt tgtttactgg ggacaaggca cactggttac cgtctcgagc     360
gcttctacaa agggcccatc ggtcttcccc ctggcaccct cctccaagag cacctctggg     420
ggcacagcgg ccctgggctg cctggtcaag gactacttcc ccgaaccggt gacggtgtcg     480
tggaactcag cgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttggtgag     660
aggccagcac agggagggag ggtgtctgct ggaagccagg ctcagcgctc ctgcctggac     720
gcatcccggc tatgcagccc cagtccaggg cagcaaggca ggccccgtct gcctcttcac     780
ccggaggcct ctgcccgccc cactcatgct caggagagag gtcttctggc ttttcccca     840
ggctctgggc aggcacaggc taggtgcccc taacccaggc cctgcacaca aggggcagg     900
tgctgggctc agacctgcca agagccatat ccgggaggac cctgccctg acctaagccc     960
accccaaagg ccaaactctc cactccctca gctcggacac cttctctcct cccagatctg    1020
agtaactccc aatcttctct ctgcagagcc caaatcttgt gacaaaactc acacatgccc    1080
accgtgccca ggtaagccag cccaggcctc gccctccagc tcaaggcggg acaggtgccc    1140
tagagtagcc tgcatccagg acaggcccc agccgggtgc tgacacgtcc acctccatct    1200
cttcctcagc acctgaactc ctgggggggac cgtcagtctt cctcttcccc ccaaaaccca    1260
aggacaccct catgatctcc cggacccctg aggtcacatg cgtggtggtg gacgtgagcc    1320
acgaagaccc tgaggtcaag ttcaactggt acgtggacgg cgtggaggtg cataatgcca    1380
agacaaagcc gcgggaggag cagtacaaca gcacgtaccg tgtggtcagc gtcctcaccg    1440
tcctgcacca ggactggctg aatggcaagg agtacaagtg caaggtctcc aacaaagccc    1500
tcccagcccc catcgagaaa accatctcca aagccaaagg tgggacccgt ggggtgcgag    1560
ggccacatgg acagaggccg gctcggccca ccctctgccc tgagagtgac cgctgtacca    1620
acctctgtcc ctacagggca gccccgagaa ccacaggtgt acaccctgcc cccatcccgg    1680
gatgagctga ccaagaacca ggtcagcctg acctgcctgg tcaaaggctt ctatcccagc    1740
gacatcgccg tggagtggga gagcaatggg cagccggaga caactacaa gaccacgcct    1800
cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggt                                 1953
```

<210> SEQ ID NO 64
<211> LENGTH: 468
<212> TYPE: PRT
<213> ORGANISM: Artificial Sequence
<220> FEATURE:
<223> OTHER INFORMATION: recombinant

<400> SEQUENCE: 64

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Phe Gly Tyr Thr Phe
        35                  40                  45

Thr Thr Tyr Pro Ile Glu Trp Met Arg Gln Ala His Gly Gln Gly Leu
    50                  55                  60

Glu Trp Ile Gly Asn Phe His Pro Tyr Asn Asp Asp Thr Lys Tyr Asn
65                  70                  75                  80

Glu Lys Phe Lys Gly Arg Val Thr Met Thr Val Asp Lys Ser Thr Thr
                85                  90                  95

Thr Val Tyr Met Glu Leu Ser Ser Leu Arg Ser Glu Asp Thr Ala Val
            100                 105                 110

Tyr Tyr Cys Ala Arg Glu Asn Tyr Gly Ser His Gly Gly Phe Val Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly
465

<210> SEQ ID NO 65
<211> LENGTH: 2010
<212> TYPE: DNA
<213> ORGANISM: Artificial Sequence
<220> FEATURE:
<223> OTHER INFORMATION: recombinant

<400> SEQUENCE: 65

| | | | | | |
|---|---|---|---|---|---|
| atggaatgga | gctgggtctt | tctcttcttc | ctgtccgtga | caactggtgt | gcactctgaa | 60 |
| gtgcaactgg | tgcagtctgg | agctgaagtg | aagaaacctg | gtgctagcgt | caaagtgtcc | 120 |
| tgcaaagcct | tcggctatac | cttcaccacg | tacccaattg | agtggatgag | gcaggcacac | 180 |
| ggacaaggat | tggagtggat | cggcaacttt | caccectaca | acgacgacac | gaagtacaac | 240 |
| gagaagttca | agggtcgcgt | gacaatgacc | gtcgataaga | gcacgaccac | tgtttatatg | 300 |
| gagctgagct | cactgagatc | cgaagatact | gccgtctact | attgtgcccg | agagaattac | 360 |
| ggatcacacg | ggggatttgt | ttactgggga | caaggcacac | tggttaccgt | ctcgagcgct | 420 |
| tctacaaagg | gcccatcggt | cttccccctg | gcaccctcct | ccaagagcac | ctctgggggc | 480 |
| acagcggccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagaaagt | tggtgagagg | 720 |
| ccagcacagg | gagggagggt | gtctgctgga | agccaggctc | agcgctcctg | cctggacgca | 780 |
| tcccggctat | gcagccccag | tccagggcag | caaggcaggc | cccgtctgcc | tcttcacccg | 840 |
| gaggcctctg | cccgcccac | tcatgctcag | ggagagggtc | ttctggcttt | tccccaggc | 900 |
| tctgggcagg | cacaggctag | gtgccccta | cccaggccct | gcacacaaag | gggcaggtgc | 960 |
| tgggctcaga | cctgccaaga | gccatatccg | ggaggaccct | gcccctgacc | taagcccacc | 1020 |
| ccaaaggcca | aactctccac | tccctcagct | cggacacctt | ctctcctccc | agatctgagt | 1080 |
| aactcccaat | cttctctctg | cagagcccaa | atcttgtgac | aaaactcaca | catgcccacc | 1140 |
| gtgcccaggt | aagccagccc | aggcctcgcc | ctccagctca | aggcgggaca | ggtgccctag | 1200 |
| agtagcctgc | atccagggac | aggccccagc | cgggtgctga | cacgtccacc | tccatctctt | 1260 |
| cctcagcacc | tgaactcctg | ggggaccgt | cagtcttcct | cttccccca | aaacccaagg | 1320 |
| acaccctcat | gatctcccgg | acccctgagg | tcacatgcgt | ggtggtggac | gtgagccacg | 1380 |
| aagaccctga | ggtcaagttc | aactggtacg | tggacggcgt | ggaggtgcat | aatgccaaga | 1440 |
| caaagccgcg | ggaggagcag | tacaacagca | cgtaccgtgt | ggtcagcgtc | ctcaccgtcc | 1500 |
| tgcaccagga | ctggctgaat | ggcaaggagt | acaagtgcaa | ggtctccaac | aaagccctcc | 1560 |
| cagcccccat | cgagaaaacc | atctccaaag | ccaaaggtgg | gacccgtggg | gtgcgagggc | 1620 |
| cacatggaca | gaggccggct | cggcccaccc | tctgccctga | gagtgaccgc | tgtaccaacc | 1680 |

```
tctgtccta caggcagcc ccgagaacca caggtgtaca ccctgccccc atcccgggat    1740
gagctgacca agaaccaggt cagcctgacc tgcctggtca aaggcttcta tcccagcgac    1800
atcgccgtgg agtgggagag caatgggcag ccggagaaca actacaagac cacgcctccc    1860
gtgctggact ccgacggctc cttcttcctc tacagcaagc tcaccgtgga caagagcagg    1920
tggcagcagg ggaacgtctt ctcatgctcc gtgatgcatg aggctctgca caaccactac    1980
acgcagaaga gcctctccct gtctccgggt                                    2010
```

<210> SEQ ID NO 66
<211> LENGTH: 108
<212> TYPE: PRT
<213> ORGANISM: Artificial Sequence
<220> FEATURE:
<223> OTHER INFORMATION: recombinant

<400> SEQUENCE: 66

```
Glu Asn Val Leu Thr Gln Ser Pro Phe Ser Leu Ser Ala Ser Val Gly
1               5                   10                  15

Asp Arg Val Thr Ile Thr Cys Arg Ala Ser Ser Ser Val Ile Ser Ser
            20                  25                  30

Tyr Leu His Trp Tyr Gln Gln Lys Pro Ala Lys Ala Pro Lys Leu Phe
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys
            100                 105
```

<210> SEQ ID NO 67
<211> LENGTH: 324
<212> TYPE: DNA
<213> ORGANISM: Artificial Sequence
<220> FEATURE:
<223> OTHER INFORMATION: recombinant

<400> SEQUENCE: 67

```
gagaatgtgc tgacacagag ccccttttca ctgtctgcat ctgtgggaga ccgggtcaca     60
ataacctgca gggctagctc aagcgtgatc agctcatacc tgcactggta tcagcaaaag    120
cccgccaaag ctcctaagct cttcatctac tccacctcca acttggcatc tggcgtgcct    180
agcagatttt ctgggagcgg ttccgggaca gactataccc tgacgattag ttccctgcaa    240
ccggaggact cgccaccta ttactgtcag cagtacaact cctacccact gacattcggc    300
ggagggacta agtcgaaat caag                                            324
```

<210> SEQ ID NO 68
<211> LENGTH: 128
<212> TYPE: PRT
<213> ORGANISM: Artificial Sequence
<220> FEATURE:
<223> OTHER INFORMATION: recombinant

<400> SEQUENCE: 68

```
Met Ser Val Pro Thr Gln Val Leu Gly Leu Leu Leu Leu Trp Leu Thr
1               5                   10                  15

Asp Ala Arg Cys Glu Asn Val Leu Thr Gln Ser Pro Phe Ser Leu Ser
```

```
                    20                  25                  30
Ala Ser Val Gly Asp Arg Val Thr Ile Thr Cys Arg Ala Ser Ser Ser
                35                  40                  45

Val Ile Ser Ser Tyr Leu His Trp Tyr Gln Gln Lys Pro Ala Lys Ala
            50                  55                  60

Pro Lys Leu Phe Ile Tyr Ser Thr Ser Asn Leu Ala Ser Gly Val Pro
 65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Phe Ala Thr Tyr Tyr Cys Gln Gln Tyr
                100                 105                 110

Asn Ser Tyr Pro Leu Thr Phe Gly Gly Gly Thr Lys Val Glu Ile Lys
                115                 120                 125

<210> SEQ ID NO 69
<211> LENGTH: 384
<212> TYPE: DNA
<213> ORGANISM: Artificial Sequence
<220> FEATURE:
<223> OTHER INFORMATION: recombinant

<400> SEQUENCE: 69
atgagtgtgc caactcaggt tctcggattg ctgcttctgt ggcttactga tgcccgctgc      60
gagaatgtgc tgacacagag ccccttttca ctgtctgcat ctgtgggaga ccgggtcaca     120
ataacctgca gggctagctc aagcgtgatc agctcatacc tgcactggta tcagcaaaag     180
cccgccaaag ctcctaagct cttcatctac tccacctcca acttggcatc tggcgtgcct     240
agcagatttt ctgggagcgg ttccgggaca gactataccc tgacgattag ttccctgcaa     300
ccggaggact cgccaccta ttactgtcag cagtacaact cctacccact gacattcggc      360
ggagggacta agtcgaaat caag                                             384

<210> SEQ ID NO 70
<211> LENGTH: 215
<212> TYPE: PRT
<213> ORGANISM: Artificial Sequence
<220> FEATURE:
<223> OTHER INFORMATION: recombinant

<400> SEQUENCE: 70

Glu Asn Val Leu Thr Gln Ser Pro Phe Ser Leu Ser Ala Ser Val Gly
 1               5                  10                  15

Asp Arg Val Thr Ile Thr Cys Arg Ala Ser Ser Ser Val Ile Ser Ser
                20                  25                  30

Tyr Leu His Trp Tyr Gln Gln Lys Pro Ala Lys Ala Pro Lys Leu Phe
                35                  40                  45

Ile Tyr Ser Thr Ser Asn Leu Ala Ser Gly Val Pro Ser Arg Phe Ser
            50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 71
<211> LENGTH: 645
<212> TYPE: DNA
<213> ORGANISM: Artificial Sequence
<220> FEATURE:
<223> OTHER INFORMATION: recombinant

<400> SEQUENCE: 71

```
gagaatgtgc tgacacagag ccccttttca ctgtctgcat ctgtgggaga ccgggtcaca      60
ataacctgca gggctagctc aagcgtgatc agctcatacc tgcactggta tcagcaaaag    120
cccgccaaag ctcctaagct cttcatctac tccacctcca acttggcatc tggcgtgcct    180
agcagatttt ctgggagcgg ttccgggaca gactataccc tgacgattag ttccctgcaa    240
ccggaggact cgccaccta ttactgtcag cagtacaact cctacccact gacattcggc    300
ggagggacta aagtcgaaat caagcgtacg gtagcggccc catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                    645
```

<210> SEQ ID NO 72
<211> LENGTH: 235
<212> TYPE: PRT
<213> ORGANISM: Artificial Sequence
<220> FEATURE:
<223> OTHER INFORMATION: recombinant

<400> SEQUENCE: 72

Met Ser Val Pro Thr Gln Val Leu Gly Leu Leu Leu Leu Trp Leu Thr
1               5                   10                  15

Asp Ala Arg Cys Glu Asn Val Leu Thr Gln Ser Pro Phe Ser Leu Ser
            20                  25                  30

Ala Ser Val Gly Asp Arg Val Thr Ile Thr Cys Arg Ala Ser Ser Ser
        35                  40                  45

Val Ile Ser Ser Tyr Leu His Trp Tyr Gln Gln Lys Pro Ala Lys Ala
    50                  55                  60

Pro Lys Leu Phe Ile Tyr Ser Thr Ser Asn Leu Ala Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Phe Ala Thr Tyr Tyr Cys Gln Gln Tyr
            100                 105                 110

Asn Ser Tyr Pro Leu Thr Phe Gly Gly Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 73
<211> LENGTH: 705
<212> TYPE: DNA
<213> ORGANISM: Artificial Sequence
<220> FEATURE:
<223> OTHER INFORMATION: recombinant

<400> SEQUENCE: 73

```
atgagtgtgc caactcaggt tctcggattg ctgcttctgt ggcttactga tgcccgctgc    60
gagaatgtgc tgacacagag ccccttttca ctgtctgcat ctgtgggaga ccgggtcaca   120
ataacctgca gggctagctc aagcgtgatc agctcatacc tgcactggta tcagcaaaag   180
cccgccaaag ctcctaagct cttcatctac tccacctcca acttggcatc tggcgtgcct   240
agcagatttt ctgggagcgg ttccgggaca gactataccc tgacgattag ttccctgcaa   300
ccggaggact cgccaccta ttactgtcag cagtacaact cctacccact gacattcggc   360
ggagggacta agtcgaaat caagcgtacg gtagcggccc catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag acagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtgt            705
```

<210> SEQ ID NO 74
<211> LENGTH: 138
<212> TYPE: PRT
<213> ORGANISM: Artificial Sequence
<220> FEATURE:
<223> OTHER INFORMATION: recombinant

<400> SEQUENCE: 74

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Thr Tyr Pro Ile Glu Trp Val Arg Gln Ala Pro Gly Gln Gly Leu

```
              50                  55                  60
Glu Trp Met Gly Asn Phe His Pro Tyr Asn Asp Asp Thr Lys Tyr Asn
 65                  70                  75                  80

Glu Lys Phe Lys Gly Arg Val Thr Ile Thr Ala Asp Lys Ser Thr Ser
                 85                  90                  95

Thr Ala Tyr Met Glu Leu Ser Ser Leu Arg Ser Glu Asp Thr Ala Val
                100                 105                 110

Tyr Tyr Cys Ala Arg Glu Asn Tyr Gly Ser His Gly Gly Phe Val Tyr
                115                 120                 125

Trp Gly Gln Gly Thr Leu Val Thr Val Ser
            130                 135

<210> SEQ ID NO 75
<211> LENGTH: 414
<212> TYPE: DNA
<213> ORGANISM: Artificial Sequence
<220> FEATURE:
<223> OTHER INFORMATION: recombinant

<400> SEQUENCE: 75
atggagtggt cctgggtgtt tctcttcttt ctctccgtca caacgggtgt tcatagcgaa      60
gtgcagcttg tgcaaagcgg cgctgaggtc aaaaagcccg gatcaagcgt gaaagtctca     120
tgcaaagcca gcggctacac cttcacaacg taccctatcg agtgggtgag gcaggctccc     180
ggccaaggac tggaatggat ggggaacttc cacccataca acgacgacac caagtacaac     240
gagaagttca gggggcgcgt tactataacc gccgacaaga gcactagcac cgcctacatg     300
gagctgagca gtctgagaag cgaggataca gccgtgtact attgtgcacg ggagaattat     360
ggctctcacg gcggatttgt gtactggggc caaggaacac tggttactgt ctcg           414

<210> SEQ ID NO 76
<211> LENGTH: 446
<212> TYPE: PRT
<213> ORGANISM: Artificial Sequence
<220> FEATURE:
<223> OTHER INFORMATION: recombinant

<400> SEQUENCE: 76

Glu Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Thr Tyr
                 20                  25                  30

Pro Ile Glu Trp Val Arg Gln Ala Pro Gly Gln Gly Leu Glu Trp Met
             35                  40                  45

Gly Asn Phe His Pro Tyr Asn Asp Asp Thr Lys Tyr Asn Glu Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asn Tyr Gly Ser His Gly Gly Phe Val Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
                210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly
                435                 440                 445

<210> SEQ ID NO 77
<211> LENGTH: 1945
<212> TYPE: DNA
<213> ORGANISM: Artificial Sequence
<220> FEATURE:
<223> OTHER INFORMATION: recombinant

<400> SEQUENCE: 77
gaagtgcagc ttgtgcaaag cggcgctgag gtcaaaaagc ccggatcaag cgtgaaagtc    60
tcatgcaaag ccagcggcta caccttcaca acgtacccta tcgagtgggt gaggcaggct   120
cccggccaag gactgaatgg atggggaaac ttccacccat acaacgacga caccaagtac   180
aacgagaagt tcaaggggcg cgttactata accgccgaca gagcactagt accgcctac    240 atggagctga gcagtctgag aagcgaggat acagccgtgt actattgtgc acgggagaat   300
tatggctctc acggcggatt tgtgtactgg ggccaaggaa cactggttac tgtctcgagc   360
gcttctacaa agggcccatc cgtcttcccc ctggcgccct gctccaggag cacctccgag   420
```

```
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttggtgag    660
aggccagcac agggagggag ggtgtctgct ggaagccagg ctcagccctc ctgcctggac    720
gcaccccggc tgtgcagccc cagcccaggg cagcaaggca tgccccatct gtctcctcac    780
ccggaggcct ctgaccaccc cactcatgcc cagggagagg gtcttctgga tttttccacc    840
aggctccggg cagccacagg ctggatgccc taccccaggg cctgcgcat acaggggcag     900 gtgctgcgct cagacctgcc aagagccata tccgggagga ccctgcccct gacctaagcc    960 cacccccaaag gccaaactct ccactccctc agctcagaca ccttctctcc tcccagatct   1020
gagtaactcc caatcttctc tctgcagagt ccaaatatgg tcccccatgc ccaccatgcc   1080
caggtaagcc aacccaggcc tcgccctcca gctcaaggcg ggacaggtgc cctagagtag   1140
cctgcatcca gggacaggcc ccagccgggt gctgacgcat ccacctccat ctcttcctca   1200
gcacctgagt tcctgggggg accatcagtc ttcctgttcc ccccaaaacc caaggacact   1260
ctcatgatct cccggacccc tgaggtcacg tgcgtggtgg tggacgtgag ccaggaagac   1320
cccgaggtcc agttcaactg gtacgtggat ggcgtggagg tgcataatgc caagacaaag   1380
ccgcgggagg agcagttcaa cagcacgtac cgtgtggtca gcgtcctcac cgtcctgcac   1440
caggactggc tgaacggcaa ggagtacaag tgcaaggtct ccaacaaagg cctcccgtcc   1500
tccatcgaga aaaccatctc caaagccaaa ggtgggaccc acggggtgcg agggccacat   1560
ggacagaggt cagctcggcc caccctctgc cctgggagtg accgctgtgc caacctctgt   1620
ccctacaggg cagccccgag agccacaggt gtacaccctg cccccatccc aggagagat    1680 gaccaagaac caggtcagcc tgacctgcct ggtcaaaggc ttctaccca gcgacatcgc    1740 cgtggagtgg gagagcaatg ggcagccgga gaacaactac aagaccacgc ctcccgtgct   1800
ggactccgac ggctccttct tcctctacag caggctaacc gtggacaaga gcaggtggca   1860 ggagggggaat gtcttctcat gctccgtgat gcatgaggct ctgcacaacc actacacaca   1920
gaagagcctc tccctgtctc tgggt    1945
```

<210> SEQ ID NO 78
<211> LENGTH: 465
<212> TYPE: PRT
<213> ORGANISM: Artificial Sequence
<220> FEATURE:
<223> OTHER INFORMATION: recombinant

<400> SEQUENCE: 78

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Thr Tyr Pro Ile Glu Trp Val Arg Gln Ala Pro Gly Gln Gly Leu
    50                  55                  60

Glu Trp Met Gly Asn Phe His Pro Tyr Asn Asp Asp Thr Lys Tyr Asn
65                  70                  75                  80

Glu Lys Phe Lys Gly Arg Val Thr Ile Thr Ala Asp Lys Ser Thr Ser
```

85                  90                  95
Thr Ala Tyr Met Glu Leu Ser Ser Leu Arg Ser Glu Asp Thr Ala Val
            100                 105                 110

Tyr Tyr Cys Ala Arg Glu Asn Tyr Gly Ser His Gly Gly Phe Val Tyr
            115                 120                 125

Trp Gly Gln Gly Thr Leu Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Lys Thr Tyr Thr Cys Asn Val
210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
                275                 280                 285

Asp Pro Glu Val Gln Phe Asn Trp Tyr Val Asp Gly Val Glu Val His
                290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Gln Glu Glu Met Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Leu
                450                 455                 460

Gly
465

<210> SEQ ID NO 79
<211> LENGTH: 2002
<212> TYPE: DNA
<213> ORGANISM: Artificial Sequence
<220> FEATURE:
<223> OTHER INFORMATION: recombinant

<400> SEQUENCE: 79

| | | | | | |
|---|---|---|---|---|---|
| atggagtggt | cctgggtgtt | tctcttcttt | ctctccgtca | caacgggtgt | tcatagcgaa | 60 |
| gtgcagcttg | tgcaaagcgg | cgctgaggtc | aaaaagcccg | gatcaagcgt | gaaagtctca | 120 |
| tgcaaagcca | gcggctacac | cttcacaacg | taccctatcg | agtgggtgag | gcaggctccc | 180 |
| ggccaaggac | tggaatggat | ggggaacttc | cacccataca | acgacgacac | caagtacaac | 240 |
| gagaagttca | aggggcgcgt | tactataacc | gccgacaaga | gcactagcac | cgcctacatg | 300 |
| gagctgagca | gtctgagaag | cgaggataca | gccgtgtact | attgtgcacg | ggagaattat | 360 |
| ggctctcacg | gcggatttgt | gtactggggc | caaggaacac | tggttactgt | ctcgagcgct | 420 |
| tctacaaagg | gcccatccgt | cttccccctg | gcgccctgct | ccaggagcac | ctccgagagc | 480 |
| acagccgccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | gaagacctac | 660 |
| acctgcaacg | tagatcacaa | gcccagcaac | accaaggtgg | acaagagagt | tggtgagagg | 720 |
| ccagcacagg | agggagggt | gtctgctgga | agccaggctc | agccctcctg | cctggacgca | 780 |
| ccccggctgt | gcagcccag | cccagggcag | caaggcatgc | cccatctgtc | tcctcacccg | 840 |
| gaggcctctg | accacccac | tcatgcccag | ggagagggtc | ttctggattt | ttccaccagg | 900 |
| ctccgggcag | ccacaggctg | gatgccccta | ccccaggccc | tgcgcataca | ggggcaggtg | 960 |
| ctgcgctcag | acctgccaag | agccatatcc | gggaggaccc | tgcccctgac | ctaagcccac | 1020 |
| cccaaaggcc | aaactctcca | ctccctcagc | tcagacacct | tctctcctcc | cagatctgag | 1080 |
| taactcccaa | tcttctctct | gcagagtcca | aatatggtcc | cccatgccca | ccatgcccag | 1140 |
| gtaagccaac | ccaggcctcg | ccctccagct | caaggcggga | caggtgccct | agagtagcct | 1200 |
| gcatccaggg | acaggcccca | gccgggtgct | gacgcatcca | cctccatctc | ttcctcagca | 1260 |
| cctgagttcc | tggggggacc | atcagtcttc | ctgttccccc | caaaacccaa | ggacactctc | 1320 |
| atgatctccc | ggaccoctga | ggtcacgtgc | gtggtggtgg | acgtgagcca | ggaagacccc | 1380 |
| gaggtccagt | tcaactggta | cgtggatggc | gtggaggtgc | ataatgccaa | gacaaagccg | 1440 |
| cgggaggagc | agttcaacag | cacgtaccgt | gtggtcagcg | tcctcaccgt | cctgcaccag | 1500 |
| gactggctga | acggcaagga | gtacaagtgc | aaggtctcca | acaaaggcct | cccgtcctcc | 1560 |
| atcgagaaaa | ccatctccaa | agccaaaggt | gggacccacg | gggtgcgagg | gccacatgga | 1620 |
| cagaggtcag | ctcggcccac | cctctgccct | gggagtgacc | gctgtgccaa | cctctgtccc | 1680 |
| tacagggcag | ccccgagagc | cacaggtgta | caccctgccc | catcccagg | aggagatgac | 1740 |
| caagaaccag | gtcagcctga | cctgcctggt | caaaggcttc | tacccagcg | acatcgccgt | 1800 |
| ggagtgggag | agcaatgggc | agccggagaa | caactacaag | accacgcctc | ccgtgctgga | 1860 |
| ctccgacggc | tccttcttcc | tctacagcag | gctaaccgtg | gacaagagca | ggtggcagga | 1920 |
| ggggaatgtc | ttctcatgct | ccgtgatgca | tgaggctctg | cacaaccact | acacacagaa | 1980 |
| gagcctctcc | ctgtctctgg | gt | | | | 2002 |

<210> SEQ ID NO 80
<211> LENGTH: 449
<212> TYPE: PRT
<213> ORGANISM: Artificial Sequence
<220> FEATURE:

<223> OTHER INFORMATION: recombinant

<400> SEQUENCE: 80

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Pro Ile Glu Trp Val Arg Gln Ala Pro Gly Gln Gly Leu Glu Trp Met
        35                  40                  45

Gly Asn Phe His Pro Tyr Asn Asp Asp Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Gly Ser His Gly Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 81
<211> LENGTH: 1953
<212> TYPE: DNA
<213> ORGANISM: Artificial Sequence
<220> FEATURE:
<223> OTHER INFORMATION: recombinant

<400> SEQUENCE: 81
```

| | | | | | |
|---|---|---|---|---|---|
| gaagtgcagc | ttgtgcaaag | cggcgctgag | gtcaaaaagc | ccggatcaag | cgtgaaagtc | 60 |
| tcatgcaaag | ccagcggcta | caccttcaca | acgtacccta | tcgagtgggt | gaggcaggct | 120 |
| cccggccaag | gactggaatg | gatggggaac | ttccacccat | acaacgacga | caccaagtac | 180 |
| aacgagaagt | tcaaggggcg | cgttactata | accgccgaca | agagcactag | caccgcctac | 240 |
| atggagctga | gcagtctgag | aagcgaggat | acagccgtgt | actattgtgc | acgggagaat | 300 |
| tatggctctc | acgcggattt | tgtgtactgg | ggccaaggaa | cactggttac | tgtctcgagc | 360 |
| gcttctacaa | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagaa | agttggtgag | 660 |
| aggccagcac | agggagggag | ggtgtctgct | ggaagccagg | ctcagcgctc | ctgcctggac | 720 |
| gcatcccggc | tatgcagccc | cagtccaggg | cagcaaggca | ggccccgtct | gcctcttcac | 780 |
| ccggaggcct | ctgcccgccc | cactcatgct | cagggagagg | gtcttctggc | tttttcccca | 840 |
| ggctctgggc | aggcacaggc | taggtgcccc | taacccaggc | cctgcacaca | aaggggcagg | 900 |
| tgctgggctc | agacctgcca | agagccatat | ccgggaggac | cctgcccctg | acctaagccc | 960 |
| accccaaagg | ccaaactctc | cactccctca | gctcggacac | tttctctcct | cccagatctg | 1020 |
| agtaactccc | aatcttctct | ctgcagagcc | caaatcttgt | gacaaaactc | acacatgccc | 1080 |
| accgtgccca | ggtaagccag | cccaggcctc | gccctccagc | tcaaggcggg | acaggtgccc | 1140 |
| tagagtagcc | tgcatccagg | acaggcccca | gccgggtgc | tgacacgtcc | acctccatct | 1200 |
| cttcctcagc | acctgaactc | ctggggggac | cgtcagtctt | cctcttcccc | ccaaaaccca | 1260 |
| aggacaccct | catgatctcc | cggacccctg | aggtcacatg | cgtggtggtg | gacgtgagcc | 1320 |
| acgaagaccc | tgaggtcaag | ttcaactggt | acgtggacgg | cgtggaggtg | cataatgcca | 1380 |
| agacaaagcc | gcgggaggag | cagtacaaca | gcacgtaccg | tgtggtcagc | gtcctcaccg | 1440 |
| tcctgcacca | ggactggctg | aatggcaagg | agtacaagtg | caaggtctcc | aacaaagccc | 1500 |
| tcccagcccc | catcgagaaa | accatctcca | aagccaaagg | tgggacccgt | ggggtgcgag | 1560 |
| ggccacatgg | acagaggccg | gctcggccca | ccctctgccc | tgagagtgac | cgctgtacca | 1620 |
| acctctgtcc | ctacagggca | gccccgagaa | ccacaggtgt | acaccctgcc | cccatcccgg | 1680 |
| gatgagctga | ccaagaacca | ggtcagcctg | acctgcctgg | tcaaaggctt | ctatcccagc | 1740 |

```
gacatcgccg tggagtggga gagcaatggg cagccggaga acaactacaa gaccacgcct    1800
cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggt                                 1953
```

```
<210> SEQ ID NO 82
<211> LENGTH: 468
<212> TYPE: PRT
<213> ORGANISM: Artificial Sequence
<220> FEATURE:
<223> OTHER INFORMATION: recombinant

<400> SEQUENCE: 82
```

| | | | | | | | | | | | | | | | |
|---|---|---|---|---|---|---|---|---|---|---|---|---|---|---|---|
| Met | Glu | Trp | Ser | Trp | Val | Phe | Leu | Phe | Phe | Leu | Ser | Val | Thr | Thr | Gly |
| 1 | | | | 5 | | | | | 10 | | | | | 15 | |
| Val | His | Ser | Glu | Val | Gln | Leu | Val | Gln | Ser | Gly | Ala | Glu | Val | Lys | Lys |
| | | | 20 | | | | | 25 | | | | | 30 | | |
| Pro | Gly | Ser | Ser | Val | Lys | Val | Ser | Cys | Lys | Ala | Ser | Gly | Tyr | Thr | Phe |
| | | 35 | | | | | 40 | | | | | 45 | | | |
| Thr | Thr | Tyr | Pro | Ile | Glu | Trp | Val | Arg | Gln | Ala | Pro | Gly | Gln | Gly | Leu |
| | 50 | | | | | 55 | | | | | 60 | | | | |
| Glu | Trp | Met | Gly | Asn | Phe | His | Pro | Tyr | Asn | Asp | Asp | Thr | Lys | Tyr | Asn |
| 65 | | | | | 70 | | | | | 75 | | | | | 80 |
| Glu | Lys | Phe | Lys | Gly | Arg | Val | Thr | Ile | Thr | Ala | Asp | Lys | Ser | Thr | Ser |
| | | | | 85 | | | | | 90 | | | | | 95 | |
| Thr | Ala | Tyr | Met | Glu | Leu | Ser | Ser | Leu | Arg | Ser | Glu | Asp | Thr | Ala | Val |
| | | | 100 | | | | | 105 | | | | | 110 | | |
| Tyr | Tyr | Cys | Ala | Arg | Glu | Asn | Tyr | Gly | Ser | His | Gly | Gly | Phe | Val | Tyr |
| | | 115 | | | | | 120 | | | | | 125 | | | |
| Trp | Gly | Gln | Gly | Thr | Leu | Val | Thr | Val | Ser | Ser | Ala | Ser | Thr | Lys | Gly |
| | 130 | | | | | 135 | | | | | 140 | | | | |
| Pro | Ser | Val | Phe | Pro | Leu | Ala | Pro | Ser | Ser | Lys | Ser | Thr | Ser | Gly | Gly |
| 145 | | | | | 150 | | | | | 155 | | | | | 160 |
| Thr | Ala | Ala | Leu | Gly | Cys | Leu | Val | Lys | Asp | Tyr | Phe | Pro | Glu | Pro | Val |
| | | | | 165 | | | | | 170 | | | | | 175 | |
| Thr | Val | Ser | Trp | Asn | Ser | Gly | Ala | Leu | Thr | Ser | Gly | Val | His | Thr | Phe |
| | | | 180 | | | | | 185 | | | | | 190 | | |
| Pro | Ala | Val | Leu | Gln | Ser | Ser | Gly | Leu | Tyr | Ser | Leu | Ser | Ser | Val | Val |
| | | 195 | | | | | 200 | | | | | 205 | | | |
| Thr | Val | Pro | Ser | Ser | Ser | Leu | Gly | Thr | Gln | Thr | Tyr | Ile | Cys | Asn | Val |
| | 210 | | | | | 215 | | | | | 220 | | | | |
| Asn | His | Lys | Pro | Ser | Asn | Thr | Lys | Val | Asp | Lys | Lys | Val | Glu | Pro | Lys |
| 225 | | | | | 230 | | | | | 235 | | | | | 240 |
| Ser | Cys | Asp | Lys | Thr | His | Thr | Cys | Pro | Pro | Cys | Pro | Ala | Pro | Glu | Leu |
| | | | | 245 | | | | | 250 | | | | | 255 | |
| Leu | Gly | Gly | Pro | Ser | Val | Phe | Leu | Phe | Pro | Pro | Lys | Pro | Lys | Asp | Thr |
| | | | 260 | | | | | 265 | | | | | 270 | | |
| Leu | Met | Ile | Ser | Arg | Thr | Pro | Glu | Val | Thr | Cys | Val | Val | Val | Asp | Val |
| | | 275 | | | | | 280 | | | | | 285 | | | |
| Ser | His | Glu | Asp | Pro | Glu | Val | Lys | Phe | Asn | Trp | Tyr | Val | Asp | Gly | Val |
| | 290 | | | | | 295 | | | | | 300 | | | | |
| Glu | Val | His | Asn | Ala | Lys | Thr | Lys | Pro | Arg | Glu | Glu | Gln | Tyr | Asn | Ser |
| 305 | | | | | 310 | | | | | 315 | | | | | 320 |

```
Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 83
<211> LENGTH: 2010
<212> TYPE: DNA
<213> ORGANISM: Artificial Sequence
<220> FEATURE:
<223> OTHER INFORMATION: recombinant

<400> SEQUENCE: 83
atggagtggt cctgggtgtt tctcttcttt ctctccgtca caacgggtgt tcatagcgaa      60
gtgcagcttg tgcaaagcgg cgctgaggtc aaaaagcccg atcaagcgt gaaagtctca     120 tgcaaagcca gcggctacac cttcacaacg taccctatcg agtgggtgag gcaggctccc     180
ggccaaggac tggaatggat ggggaacttc cacccataca cgacgacac caagtacaac     240 gagaagttca gggggcgcgt tactataacc gccgacaaga gcactagcac cgcctacatg     300
gagctgagca gtctgagaag cgaggataca gccgtgtact attgtgcacg ggagaattat     360
ggctctcacg gcggatttgt gtactggggc caaggaacac tggttactgt ctcgagcgct     420
tctacaaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tggtgagagg     720
ccagcacagg gagggagggt gtctgctgga agccaggctc agcgctcctg cctggacgca     780
tcccggctat gcagccccag tccagggcag caaggcaggc cccgtctgcc tcttcacccg     840
gaggcctctg cccgccccac tcatgctcag ggagagggtc ttctggcttt ttccccaggc     900
tctgggcagg cacaggctag gtgcccctaa cccaggccct gcacacaaag ggcaggtgc      960 tgggctcaga cctgccaaga gccatatccg gaggaccct gcccctgacc taagcccacc     1020
ccaaaggcca aactctccac tccctcagct cggacacctt ctctcctccc agatctgagt     1080
aactcccaat cttctctctg cagagcccaa atcttgtgac aaaactcaca catgcccacc     1140
gtgcccaggt aagccagccc aggcctcgcc ctccagctca aggcgggaca ggtgccctag    1200
```

```
agtagcctgc atccagggac aggccccagc cgggtgctga cacgtccacc tccatctctt    1260
cctcagcacc tgaactcctg gggggaccgt cagtcttcct cttcccccca aaacccaagg    1320
acaccctcat gatctcccgg accoctgagg tcacatgcgt ggtggtggac gtgagccacg    1380
aagaccctga ggtcaagttc aactggtacg tggacggcgt ggaggtgcat aatgccaaga    1440
caaagccgcg ggaggagcag tacaacagca cgtaccgtgt ggtcagcgtc ctcaccgtcc    1500
tgcaccagga ctggctgaat ggcaaggagt acaagtgcaa ggtctccaac aaagccctcc    1560
cagcccccat cgagaaaacc atctccaaag ccaaaggtgg gacccgtggg gtgcgagggc    1620
cacatggaca gaggccggct cggcccaccc tctgccctga gagtgaccgc tgtaccaacc    1680
tctgtcccta cagggcagcc ccgagaacca caggtgtaca ccctgccccc atcccgggat    1740
gagctgacca agaaccaggt cagcctgacc tgcctggtca aaggcttcta tcccagcgac    1800
atcgccgtgg agtgggagag caatgggcag ccggagaaca actacaagac cacgcctccc    1860
gtgctggact ccgacggctc cttcttcctc tacagcaagc tcaccgtgga caagagcagg    1920
tggcagcagg ggaacgtctt ctcatgctcc gtgatgcatg aggctctgca caaccactac    1980
acgcagaaga gcctctccct gtctccgggt                                     2010
```